(12) United States Patent
van Duzer et al.

(10) Patent No.: US 9,790,180 B2
(45) Date of Patent: Oct. 17, 2017

(54) PIPERIDINE DERIVATIVES AS HDAC1/2 INHIBITORS

(71) Applicant: Acetylon Pharmaceuticals, Inc., Boston, MA (US)

(72) Inventors: John H. van Duzer, Georgetown, MA (US); Ralph Mazitschek, Belmont, MA (US)

(73) Assignee: REGENACY PHARMACEUTICALS, LLC, Boston, MA (US)

( * ) Notice: Subject to any disclaimer, the term of this patent is extended or adjusted under 35 U.S.C. 154(b) by 0 days.

(21) Appl. No.: 14/966,556

(22) Filed: Dec. 11, 2015

(65) Prior Publication Data

US 2016/0168093 A1    Jun. 16, 2016

Related U.S. Application Data

(60) Provisional application No. 62/238,931, filed on Oct. 8, 2015, provisional application No. 62/091,221, filed on Dec. 12, 2014.

(51) Int. Cl.

| | | |
|---|---|---|
| *C07D 211/00* | (2006.01) |
| *C07D 401/00* | (2006.01) |
| *C07D 405/00* | (2006.01) |
| *C07D 409/00* | (2006.01) |
| *C07D 411/00* | (2006.01) |
| *C07D 413/00* | (2006.01) |
| *C07D 417/00* | (2006.01) |
| *C07D 419/00* | (2006.01) |
| *C07D 421/00* | (2006.01) |
| *C07D 211/56* | (2006.01) |
| *C07D 211/92* | (2006.01) |
| *C07D 211/06* | (2006.01) |
| *C07D 211/58* | (2006.01) |
| *C07D 409/12* | (2006.01) |
| *C07D 409/14* | (2006.01) |

(52) U.S. Cl.
CPC .......... *C07D 211/58* (2013.01); *C07D 409/12* (2013.01); *C07D 409/14* (2013.01)

(58) Field of Classification Search
USPC ........ 546/189, 192, 196, 223, 226; 514/315, 514/317, 320, 329, 330
See application file for complete search history.

(56) References Cited

U.S. PATENT DOCUMENTS

| | | |
|---|---|---|
| 7,868,205 B2 | 1/2011 | Moradei et al. |
| 8,119,685 B2 | 2/2012 | Heidebrecht et al. |
| 8,148,526 B1 | 4/2012 | van Duzer et al. |
| 8,394,810 B2 | 3/2013 | van Duzer et al. |
| 8,598,168 B2 | 12/2013 | Moradei et al. |
| 8,609,678 B2 | 12/2013 | van Duzer et al. |
| 8,614,223 B2 | 12/2013 | van Duzer et al. |
| 9,096,549 B2 | 8/2015 | van Duzer et al. |
| 9,139,583 B2 | 9/2015 | van Duzer et al. |
| 9,145,412 B2 | 9/2015 | van Duzer |
| 9,249,087 B2 | 2/2016 | Kozikowski et al. |
| 9,278,963 B2 * | 3/2016 | van Duzer ........... C07D 417/12 |
| 9,421,212 B2 | 8/2016 | van Duzer |
| 2009/0124631 A1 | 5/2009 | Li et al. |
| 2009/0285772 A1 | 11/2009 | Phiasivongsa et al. |
| 2013/0225543 A1 | 8/2013 | Jones et al. |
| 2014/0011767 A1 | 1/2014 | Yang et al. |
| 2014/0128391 A1 | 5/2014 | van Duzer et al. |
| 2014/0142104 A1 | 5/2014 | van Duzer et al. |
| 2014/0142117 A1 | 5/2014 | van Duzer et al. |
| 2014/0357512 A1 | 12/2014 | Jones et al. |
| 2015/0045380 A1 | 2/2015 | van Duzer et al. |
| 2015/0099744 A1 | 4/2015 | Yang et al. |
| 2015/0105358 A1 | 4/2015 | Quayle et al. |
| 2015/0105383 A1 | 4/2015 | Quayle et al. |
| 2015/0105384 A1 * | 4/2015 | Jones ................... C07D 417/12 514/235.2 |
| 2015/0105409 A1 | 4/2015 | Quayle et al. |
| 2015/0150871 A1 | 6/2015 | Quayle et al. |
| 2015/0176076 A1 | 6/2015 | Yang et al. |
| 2015/0239869 A1 | 8/2015 | Mazitschek et al. |
| 2015/0299130 A1 | 10/2015 | van Duzer et al. |
| 2016/0030458 A1 | 2/2016 | Jones et al. |
| 2016/0137630 A1 | 5/2016 | Shearstone |
| 2016/0168093 A1 | 6/2016 | van Duzer |

FOREIGN PATENT DOCUMENTS

| | | | | |
|---|---|---|---|---|
| CA | WO 2005030704 A1 * | 4/2005 | ........... | C07C 233/25 |
| KR | WO 2013100672 A1 * | 7/2013 | ........... | C07D 401/12 |
| WO | 2005/030704 A1 | 4/2005 | | |
| WO | 2005/030705 A1 | 4/2005 | | |
| WO | WO 2005030704 A1 * | 4/2005 | | |
| WO | 2008/046085 A2 | 4/2008 | | |
| WO | 2008/111299 A1 | 9/2008 | | |
| WO | 2009/049132 A1 | 4/2009 | | |
| WO | 2015/054474 A1 | 4/2015 | | |

OTHER PUBLICATIONS

Clinical Trial NCT01245179: Study of Panobinostat in Patients with Sickle Cell Disease. Published 2010.*
Wagner and coworkers (Histone Deacetylase (HDAC) inhibitors in recent clinical trials for cancer therapy, Clin. Epigenet. vol. 1 pp. 117-136, published 2010).*
International Search Report with Written Opinion corresponding to International Patent Application No. PCT/US2015/054666, dated Apr. 21, 2016.
International Search Report with Written Opinion corresponding to International Patent Application No. PCT/US2015/065289, dated May 12, 2016.
Selective HDAC1 and HDAC2 Inhibitor.
U.S. Appl. No. 15/214,061, filed Jul. 19, 2016, John H. van Duzer. Induction of GATA2 by HDAC1 and HDAC2 Inhibitors.
Piperidine Derivatives as HDAC1/2 Inhibitors.

* cited by examiner

*Primary Examiner* — Timothy Thomas
*Assistant Examiner* — George W Kosturko
(74) *Attorney, Agent, or Firm* — Lathrop & Gage LLP; Brian C. Trinque

(57) ABSTRACT

Provided herein are compounds, pharmaceutical compositions comprising such compounds, and methods of using such compounds to treat diseases or disorders associated with HDAC1 and/or HDAC2 activity.

7 Claims, 7 Drawing Sheets

PIPERIDINE DERIVATIVES AS HDAC1/2 INHIBITORS

RELATED APPLICATIONS

This application claims priority to U.S. Provisional Application Ser. No. 62/091,221, filed Dec. 12, 2014, and to U.S. Provisional Application Ser. No. 62/238,931, filed Oct. 8, 2015, which are incorporated herein by reference in their entireties.

BACKGROUND

A biological target of current interest is histone deacetylase (HDAC) (see, for example, a discussion of the use of inhibitors of histone deacetylases for the treatment of cancer: Marks et al. *Nature Reviews Cancer* 2001, 7, 194; Johnstone et al. *Nature Reviews Drug Discovery* 2002, 287). Post-translational modification of proteins through acetylation and deacetylation of lysine residues plays a critical role in regulating their cellular functions. HDACs are zinc hydrolases that modulate gene expression through deacetylation of the N-acetyl-lysine residues of histone proteins and other transcriptional regulators (Hassig et al. *Curr. Opin. Chem. Biol.* 1997, 1, 300-308). HDACs participate in cellular pathways that control cell shape and differentiation, and an HDAC inhibitor has been shown to be effective in treating an otherwise recalcitrant cancer (Warrell et al. *J. Natl. Cancer Inst.* 1998, 90, 1621-1625).

Eleven human HDACs, which use Zn as a cofactor, have been identified (Taunton et al. *Science* 1996, 272, 408-411; Yang et al. *J. Biol. Chem.* 1997, 272, 28001-28007. Grozinger et al. *Proc. Natl. Acad. Sci. U.S.A.* 1999, 96, 4868-4873; Kao et al. *Genes Dev.* 2000, 14, 55-66. Hu et al. *J. Biol. Chem.* 2000, 275, 15254-15264; Zhou et al. *Proc. Natl. Acad. Sci U.S.A.* 2001, 98, 10572-10577; Venter et al. *Science* 2001, 291, 1304-1351) and these members fall into three classes (class I, II, and IV) based on sequence homology to their yeast orthologues (O. Witt et al. *Cancer Letters*, 2009, 277, 8-21). Class I HDACs include HDAC1, HDAC2, HDAC3, and HDAC8, and are referred to as "classical" HDACs, which implies a catalytic pocket with a $Zn^{2+}$ ion at its base.

There remains a need for preparing structurally diverse HDAC inhibitors, particularly ones that are potent and/or selective inhibitors of particular classes of HDACs and individual HDACs.

SUMMARY OF THE INVENTION

Provided herein are compounds, pharmaceutical compositions comprising such compounds, and methods of using such compounds to treat diseases or disorders associated with HDAC activity, particularly diseases or disorders that involve HDAC1 and/or HDAC2 expression. Diseases that involve HDAC1 and/or HDAC2 expression include, but are not limited to, various types of cancer and hemoglobinopathies, such as sickle-cell anemia and beta-thalassemia.

Thus, in one aspect, provided herein is a compound of Formula I:

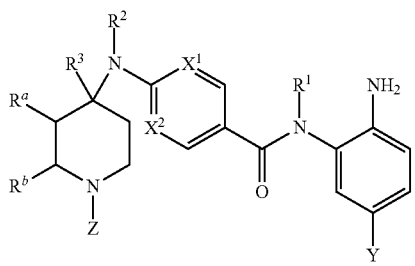

or a pharmaceutically acceptable salt thereof.

In an embodiment, provided herein is a compound of Formula II:

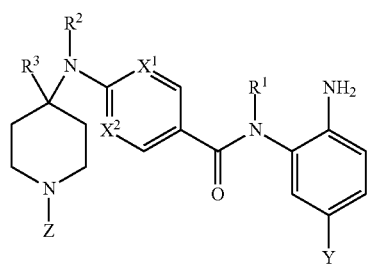

or a pharmaceutically acceptable salt thereof.

In a particular embodiment, provided herein is a compound of Formula III:

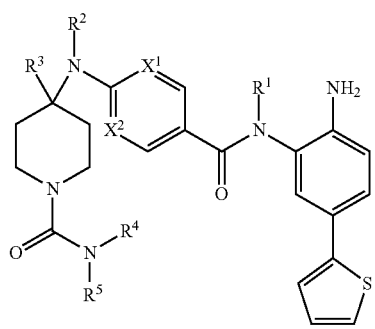

or a pharmaceutically acceptable salt thereof.

In another embodiment, provided herein are the compounds of Table 1, or pharmaceutically acceptable salts thereof.

In another aspect, provided herein is a pharmaceutical composition comprising a compound of Formula I, Formula II, Formula IIa, Formula III, or Formula IIIa, a compound presented in Table 1, a compound presented in Table 1a, or pharmaceutically acceptable salts thereof, together with a pharmaceutically acceptable carrier.

In another aspect, provided herein is a method of inhibiting the activity of HDAC1 and/or HDAC2 in a subject comprising administering to the subject a compound of Formula I, Formula II, Formula IIa, Formula III, or Formula IIIa, a compound presented in Table 1, a compound presented in Table 1a, or pharmaceutically acceptable salts thereof.

In another aspect, provided herein is a method of selectively inhibiting the activity of each of HDAC1 and/or HDAC2 over other HDACs in a subject comprising administering to the subject a compound of Formula I, Formula II, Formula IIa, Formula III, or Formula IIIa, a compound presented in Table 1, a compound presented in Table 1a, or pharmaceutically acceptable salts thereof. In some embodiments, the compound has a selectivity for each of HDAC1 and/or HDAC2 that is 5 to 1000 fold greater than for other HDACs. In other embodiments, the compound has a selectivity for each of HDAC1 and/or HDAC2 when tested in a HDAC enzyme assay, of about 5 to about 1000 fold greater than for other HDACs.

In another aspect, provided herein is a method for treating a disease mediated by one or more HDACs in a subject comprising administering to the subject in need thereof a compound of Formula I, Formula II, Formula IIa, Formula III, or Formula IIIa, a compound presented in Table 1, a compound presented in Table 1a, or pharmaceutically acceptable salts thereof. In some embodiments, the disease is mediated by HDAC1 and HDAC2. In another embodiment, the disease is mediated by HDAC1. In yet another embodiment, the disease is mediated by HDAC2.

In another aspect, provided herein is a method for treating a disease in a subject comprising administering to the subject a compound of Formula I, Formula II, Formula IIa, Formula III, or Formula IIIa, a compound presented in Table 1, a compound presented in Table 1a, or pharmaceutically acceptable salts thereof. In an embodiment, the disease is myelodysplastic syndrome. In an embodiment, the disease is a hemoglobinopathy. In another embodiment, the disease is sickle-cell disease. In yet another embodiment, the disease is beta-thalassemia.

In a further embodiment, the disease is a cancer. The cancer can be selected from lung cancer, colon cancer, breast cancer, neuroblastoma, leukemia, or lymphoma. In yet a further embodiment, the cancer is neuroblastoma. The leukemia can be acute myelogenous leukemia or acute megakaryocytic leukemia.

In another aspect, provided herein is a method for treating sickle cell disease, beta thalassemia, myelodysplastic syndrome, acute myelogenous leukemia, neuroblastoma, or acute megakaryocytic leukemia in a subject in need thereof comprising administering to the subject a therapeutically effective amount of a compound of Formula I, Formula II, Formula IIa, Formula III, or Formula IIIa, a compound presented in Table 1, a compound presented in Table 1a, or pharmaceutically acceptable salts thereof.

In a further embodiment of the methods of treatment described herein, the subject to be treated is a human.

In yet another aspect, provided herein is a method for treating a disease or disorder associated with GATA binding protein 2 (Gata2) deficiency comprising administering to a subject in need thereof a therapeutically effective amount of a compound of Formula I, Formula II, Formula IIa, Formula III, or Formula IIIa, a compound presented in Table 1, a compound presented in Table 1a, or pharmaceutically acceptable salts thereof.

In still another aspect, provided herein is a method for increasing GATA binding protein 2 (Gata2) expression in a cell comprising contacting the cell with a compound of Formula I, Formula II, Formula IIa, Formula III, or Formula IIIa, a compound presented in Table 1, a compound presented in Table 1a, or pharmaceutically acceptable salts thereof.

In a further aspect, provided herein is a method for inducing HbG (gamma globin) expression in a subject, comprising administering to the subject a compound of Formula I, Formula II, Formula IIa, Formula III, or Formula IIIa, a compound presented in Table 1, a compound presented in Table 1a, or pharmaceutically acceptable salts thereof.

DETAILED DESCRIPTION

Figure 1:
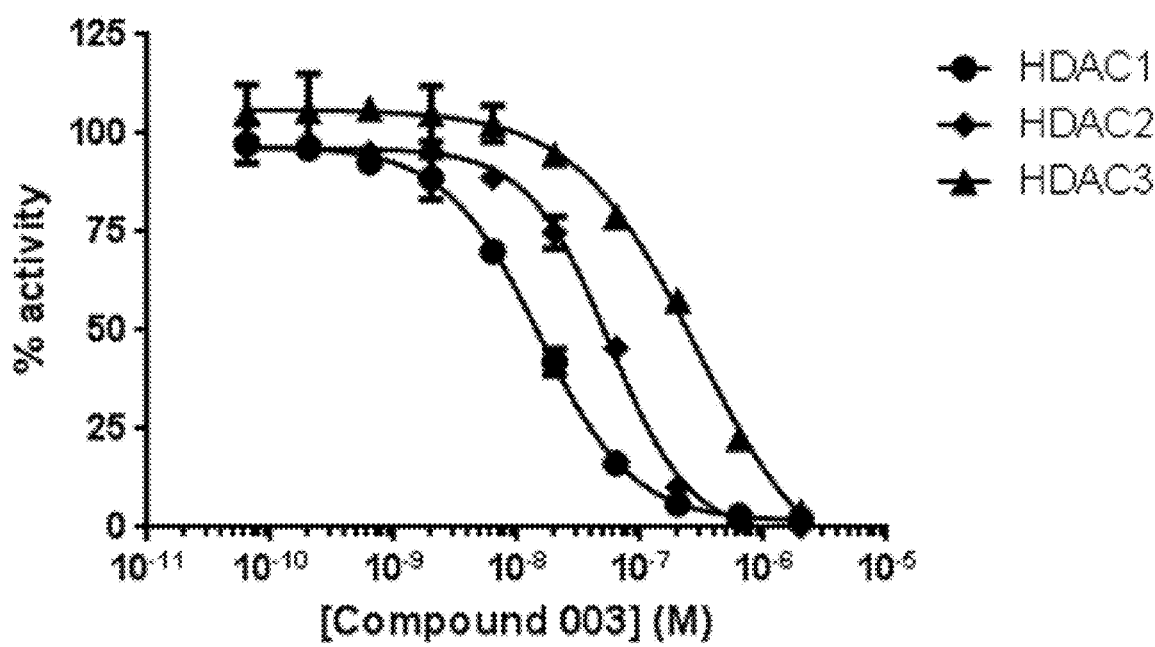
FIG. 1 is a graph showing the HDAC inhibition profile of Compound 003 with respect to HDAC1, HDAC2, and HDAC3 (See, Example 43).

The instant application is directed, generally, to compounds, pharmaceutical compositions comprising such compounds, and methods of using such compounds to treat diseases or disorders associated with HDAC activity, particularly diseases or disorders that involve any type of HDAC1 and/or HDAC2 expression.

Definitions

Listed below are definitions of various terms used to describe this invention. These definitions apply to the terms as they are used throughout this specification and claims, unless otherwise limited in specific instances, either individually or as part of a larger group.

The term "about" generally indicates a possible variation of no more than 10%, 5%, or 1% of a value. For example, "about 25 mg/kg" will generally indicate, in its broadest sense, a value of 22.5-27.5 mg/kg, i.e., 25±2.5 mg/kg.

The term "alkyl" refers to saturated, straight- or branched-chain hydrocarbon moieties containing, in certain embodiments, between one and six, or one and eight carbon atoms, respectively. The number of carbon atoms in an alkyl substituent can be indicated by the prefix "$C_x$-$C_y$," where x is the minimum and y is the maximum number of carbon atoms in the substituent. Likewise, a $C_x$ chain description indicates a group containing x carbon atoms (i.e., not including the number of heteroatoms). Examples of $C_1$-$C_6$-alkyl moieties include, but are not limited to, methyl, ethyl, propyl, isopropyl, n-butyl, tent-butyl, neopentyl, n-hexyl moieties; and examples of $C_1$-$C_8$-alkyl moieties include, but are not limited to, methyl, ethyl, propyl, isopropyl, n-butyl, tert-butyl, neopentyl, n-hexyl, heptyl, and octyl moieties.

The term "alkoxy" refers to an —O-alkyl moiety. Non-limiting examples of $C_1$-$C_6$-alkoxy include methoxy, ethoxy, 1-propoxy, 2-propoxy, n-butoxy, t-butoxy, pentoxy, hexoxy, etc. The alkyl portion of alkoxy can be straight- or branched-chain.

The term "aryl" refers to a mono- or poly-cyclic carbocyclic ring system having one or more aromatic rings, fused or non-fused, including, but not limited to, phenyl (i.e., $C_6$-aryl), naphthyl, tetrahydronaphthyl, indanyl, idenyl, and the like. In some embodiments, aryl groups have 6 carbon atoms (e.g., $C_6$-aryl). In some embodiments, aryl groups have from six to ten carbon atoms (e.g., $C_6$-$C_{10}$-aryl). In some embodiments, aryl groups have from six to sixteen carbon atoms.

The term "cycloalkyl" denotes a monovalent group derived from a monocyclic or polycyclic saturated or partially unsaturated carbocyclic ring compound. Examples of $C_3$-$C_6$-cycloalkyl include, but are not limited to, cyclopropyl, cyclobutyl, cyclopentyl, and cyclohexyl; examples of $C_3$-$C_8$-cycloalkyl include, but are not limited to, cyclopropyl, cyclobutyl, cyclopentyl, cyclohexyl, cyclopentyl and cyclooctyl; and examples of $C_3$-$C_{12}$-cycloalkyl include, but are not limited to, cyclopropyl, cyclobutyl, cyclopentyl, cyclohexyl, bicyclo [2.2.1]heptyl, and bicyclo[2.2.2]octyl. Also contemplated are monovalent groups derived from a monocyclic or polycyclic carbocyclic ring compound having a carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl" refers to a mono- or poly-cyclic (e.g., bi-, or tri-cyclic or more) fused or non-fused moiety or ring system having at least one aromatic ring, where one or more of the ring-forming atoms is a heteroatom such as oxygen, sulfur, or nitrogen. In some embodiments, the heteroaryl group has one to eight carbon atoms, one to six carbon atoms, two to 6 carbon atoms (e.g., $C_1$-$C_8$-heteroaryl, $C_1$-$C_6$-heteroaryl, or $C_2$-$C_6$-heteroaryl). In further embodiment the heteroaryl group has one to fifteen carbon atoms. In some embodiments, the heteroaryl group contains five to sixteen ring atoms of which one ring atom is selected from oxygen, sulfur, and nitrogen; zero, one, two, or three ring atoms are additional heteroatoms independently selected from oxygen, sulfur, and nitrogen; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiazolyl, thiadiazolyl, oxadiazolyl, thiophenyl, furanyl, indolyl, quinolinyl, isoquinolinyl, benzimidazolyl, benzooxazolyl, quinoxalinyl, acridinyl, and the like.

The term "heterocyclyl" refers to a non-aromatic 3-, 4-, 5-, 6- or 7-membered ring or a bi- or tri-cyclic group fused of non-fused system, where (i) each ring contains between one and three heteroatoms independently selected from oxygen, sulfur, and nitrogen and the remaining atoms are carbon (e.g., $C_2$-$C_6$-heterocyclyl, $C_3$-$C_6$-heterocyclyl, or $C_3$-$C_5$-heterocyclyl), (ii) each 5-membered ring has 0 to 1 double bonds and each 6-membered ring has 0 to 2 double bonds, (iii) the nitrogen and sulfur heteroatoms can optionally be oxidized, (iv) the nitrogen heteroatom can optionally be quaternized, and (iv) any of the above rings can be fused to a benzene ring. The term "heterocyclyl" includes, but is not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The terms "halo" and "halogen" refer to an atom selected from fluorine, chlorine, bromine and iodine.

The term "haloalkyl" refers to alkl radicals wherein any one or more of the alkyl carbon atoms is substituted with halo as defined above. Haloalkyl embraces monohaloalkyl, dihaloalkyl, and polyhaloalkyl radicals. The term "haloalkyl" includes, but is not limited to, fluoromethyl, difluoromethyl, trifluoromethyl, chloromethyl, dichloromethyl, trichloromethyl, and pentafluoroethyl.

The term "hydroxy" refers to an —OH radical.

The term "HDAC" refers to histone deacetylases, which are enzymes that remove the acetyl groups from the lysine residues in core histones, thus leading to the formation of a condensed and transcriptionally silenced chromatin. There are currently 18 known histone deacetylases, which are classified into four groups. Class I HDACs, which include HDAC1, HDAC2, HDAC3, and HDAC8, are related to the yeast RPD3 gene. Class II HDACs, which include HDAC4, HDAC5, HDAC6, HDAC7, HDAC9, and HDAC10, are related to the yeast Hda1 gene. Class III HDACs, which are also known as the sirtuins are related to the Sir2 gene and include SIRT1-7. Class IV HDACs, which contains only HDAC11, has features of both Class I and II HDACs. The term "HDAC" refers to any one or more of the 18 known histone deacetylases, unless otherwise specified.

The term "inhibitor" is synonymous with the term antagonist.

The term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Additionally, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound, which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17$^{th}$ ed., Mack Publishing Company, Easton, Pa., 1985, p. 1418 and Journal of Pharmaceutical Science, 66, 2 (1977), each of which is incorporated herein by reference in its entirety.

Combinations of substituents and variables envisioned by this invention are only those that result in the formation of stable compounds. The term "stable" refers to compounds which possess stability sufficient to allow manufacture and which maintains the integrity of the compound for a sufficient period of time to be useful for the purposes detailed herein (e.g., therapeutic or prophylactic administration to a subject).

The term "subject" refers to a mammal. A subject therefore refers to, for example, dogs, cats, horses, cows, pigs, guinea pigs, and the like. Preferably the subject is a human. When the subject is a human, the subject can be referred to herein as a patient.

Compounds of the Invention

In one aspect, provided herein is a compound of Formula I:

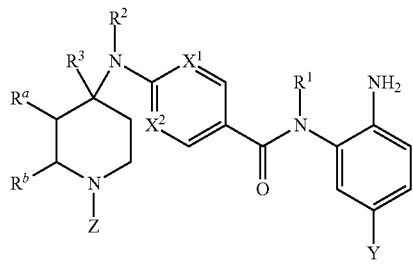

I or a pharmaceutically acceptable salt thereof,
wherein,
$X^1$ is $CR^7$ or N;
$X^2$ is CH or N;
Y is selected from the group consisting of:

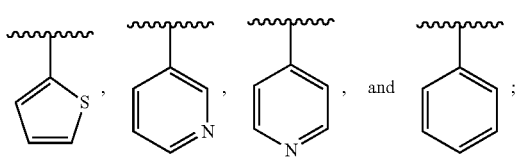

Z is selected from the group consisting of H, $C_1$-$C_6$-alkyl, $C_6$-aryl, $C(O)NR^4R^5$, $C(O)OR^6$, $C(O)C_1$-$C_6$-alkyl, $C(O)C_0$-$C_6$-alkyl-$C_6$-aryl, $C(O)$—$C_3$-$C_6$-cycloalkyl, $C(O)$—$C_2$-$C_6$-heterocyclyl, and $C(O)C_0$-$C_6$-alkyl-heteroaryl, wherein the aryl, heteroaryl, cycloalkyl, and heterocyclyl groups are optionally substituted by 1 or 2 of $C_1$-$C_6$-alkyl, halo, $C_1$-$C_6$-haloalkyl, hydroxy, or $C_1$-$C_6$-alkoxy;
$R^a$ and $R^b$ are H, or $R^a$ and $R^b$ together form a fused $C_6$-aryl;
$R^1$ is selected from the group consisting of H and $C_1$-$C_6$-alkyl;
$R^2$ is selected from the group consisting of H, $C_1$-$C_6$-alkyl, and $C_6$-aryl;
$R^3$ is selected from the group consisting of H, $C_1$-$C_6$-alkyl, and $C_6$-aryl;
or $R^2$ and $R^3$ together form a $C_3$-$C_6$-heterocyclyl;
$R^4$ is selected from the group consisting of H, $C_1$-$C_6$-alkyl, $C_1$-$C_6$-alkyl-OH, and $C_1$-$C_6$—$NH_2$;
$R^5$ is $C_1$-$C_6$-alkyl;
or $R^4$ and $R^5$ together form a $C_2$-$C_6$-heterocyclyl, wherein heterocyclyl is optionally substituted by 1 or 2 of $C_1$-$C_6$-alkyl, halo, $C_1$-$C_6$-haloalkyl, hydroxy, or $C_1$-$C_6$-alkoxy;
$R^6$ is selected from the group consisting of $C_1$-$C_6$-alkyl and $C_0$-$C_6$-alkyl-$C_6$-aryl, wherein aryl is optionally substituted by 1 or 2 of $C_1$-$C_6$-alkyl, halo, or hydroxy; and
$R^7$ is selected from the group consisting of H, $C_1$-$C_6$-alkyl, and $C_3$-$C_6$-cycloalkyl.

In an embodiment of the compound of Formula I, $R^a$ and $R^b$ are H and $R^3$ is selected from the group consisting of H and $C_6$-aryl.

In an embodiment of the compound of Formula I, Y is selected from the group consisting of:

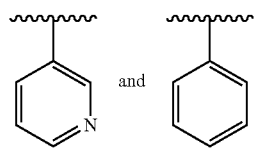 [SMILES: *c1cccnc1 ; *c1ccccc1]

In another embodiment of the compound of Formula I, Z is selected from the group consisting of H, $C_1$-$C_6$-alkyl, $C_6$-aryl, $C(O)OR^6$, $C(O)C_1$-$C_6$-alkyl, $C(O)C_0$-$C_6$-alkyl-$C_6$-aryl, $C(O)$—$C_3$-$C_6$-cycloalkyl, and $C(O)C_0$-$C_6$-alkyl-heteroaryl, wherein the aryl, heteroaryl, and cycloalkyl groups are optionally substituted by 1 or 2 of $C_1$-$C_6$-alkyl, halo, $C_1$-$C_6$-haloalkyl, hydroxy, or $C_1$-$C_6$-alkoxy.

In an embodiment, the compound of Formula I is a compound of Formula II:

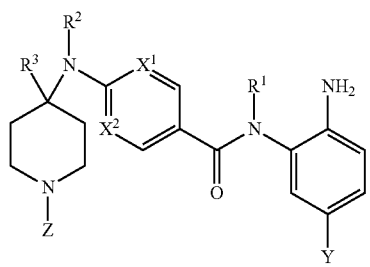

II or a pharmaceutically acceptable salt thereof.

In an embodiment of the compound of Formula I or Formula II, $X^1$ and $X^2$ are each N, or $X^1$ and $X^2$ are each CH.

In another embodiment of the compound of Formula I or Formula II, Y is:

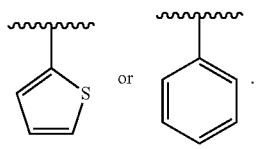 [SMILES: *c1cccs1 ; *c1ccccc1]

In another embodiment of the compound of Formula I or Formula II, Z is selected from the group consisting of $C(O)NR^4R^5$, $C(O)OR^6$, $C(O)$—$C_3$-$C_6$-cycloalkyl, $C(O)$—$C_2$-$C_6$-heterocyclyl, and $C(O)C_0$-$C_6$-alkyl-heteroaryl, wherein heteroaryl, cycloalkyl, or heterocyclyl are optionally substituted by 1 or 2 of $C_1$-$C_6$-alkyl, halo, or hydroxy; and
$R^6$ is $C_6$-aryl.

In yet another embodiment of the compound of Formula I or Formula II, Z is selected from the group consisting of H, $C_1$-$C_6$-alkyl, and $C_6$-aryl.

In an embodiment of the compound of Formula I or Formula II, $R^1$ is H.

In another embodiment of the compound of Formula I or Formula II, $R^2$ is H.

In another embodiment of the compound of Formula I or Formula II, $R^3$ is H, methyl, ethyl, isopropyl, or phenyl. In another embodiment of the compound of Formula I or Formula II, $R^3$ is selected from the group consisting of H or $C_6$-aryl. In yet a further embodiment of the compound of Formula I or Formula II, $R^3$ is H.

In an embodiment, the compound of Formula I is a compound of Formula IIa:

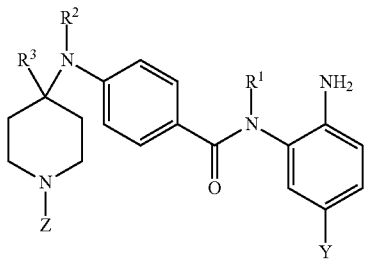

or a pharmaceutically acceptable salt thereof.

In an embodiment of the compound of Formula IIa, Y is:

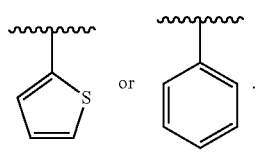 [SMILES: *c1cccs1 ; *c1ccccc1]

In another embodiment of the compound of Formula IIa, Z is selected from the group consisting of $C(O)NR^4R^5$, $C(O)OR^6$, $C(O)$—$C_3$-$C_6$-cycloalkyl, $C(O)$—$C_2$-$C_6$-heterocyclyl, and $C(O)C_0$-$C_6$-alkyl-heteroaryl, wherein heteroaryl, cycloalkyl, or heterocyclyl are optionally substituted by 1 or 2 of $C_1$-$C_6$-alkyl, halo, or hydroxy; and $R^6$ is $C_6$-aryl.

In yet another embodiment of the compound of Formula IIa, Z is selected from the group consisting of H, $C_1$-$C_6$-alkyl, and $C_6$-aryl.

In an embodiment of the compound of Formula IIa, $R^1$ is H.

In another embodiment of the compound of Formula IIa, $R^2$ is H.

In another embodiment of the compound of Formula IIa, $R^3$ is H, methyl, ethyl, isopropyl, or phenyl. In yet a further embodiment of the compound of Formula IIa, $R^3$ is H.

In a specific embodiment, $R^1$ is H; $R^2$ is H; and $R^3$ is H.

In a further embodiment, the compound of Formula I is a compound of Formula III:

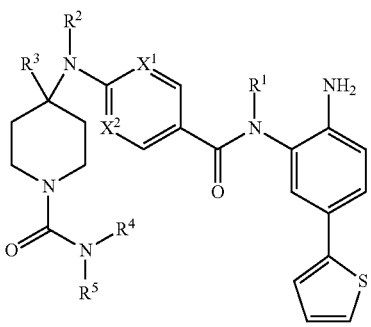

or a pharmaceutically acceptable salt thereof.

In an embodiment of the compound of Formula III, $X^1$ and $X^2$ are each N, or $X^1$ and $X^2$ are each CH.

In an embodiment of the compound of Formula III, $R^2$ is H.

In an embodiment of the compound of Formula III, $R^3$ is H, methyl, or isopropyl.

In an embodiment of the compound of Formula III, $R^4$ is H and $R^5$ is $C_1$-$C_6$-alkyl.

In another embodiment of the compound of Formula III, $R^4$ and $R^5$ together form a heterocyclyl selected from the group consisting of morpholinyl, piperidinyl, piperazinyl, and pyrrolidinyl, wherein the morpholinyl, piperidinyl, piperazinyl, and pyrrolidinyl are optionally substituted by 1 or 2 of $C_1$-$C_6$-alkyl, halo, or hydroxy.

In another embodiment of the compound of Formula III, $X^1$ and $X^2$ are N;
$R^1$ is H;
$R^2$ is H;
$R^3$ is H or $C_1$-$C_4$-alkyl; and
$R^4$ and $R^5$ together form a heterocyclyl selected from the group consisting of morpholinyl, piperidinyl, piperazinyl, and pyrrolidinyl, wherein the morpholinyl, piperidinyl, piperazinyl, and pyrrolidinyl are optionally substituted by 1 or 2 of $C_1$-$C_6$-alkyl, halo, or hydroxy.

In another embodiment of the compound of Formula III, $X^1$ and $X^2$ are N;
$R^1$ is H;
$R^2$ is H;
$R^3$ is H; and
$R^4$ and $R^5$ together form a heterocyclyl selected from the group consisting of morpholinyl, piperidinyl, piperazinyl, and pyrrolidinyl, wherein the morpholinyl, piperidinyl, piperazinyl, and pyrrolidinyl are optionally substituted by 1 or 2 of $C_1$-$C_6$-alkyl, halo, or hydroxy.

In a further embodiment, the compound of Formula I is a compound of Formula IIIa:

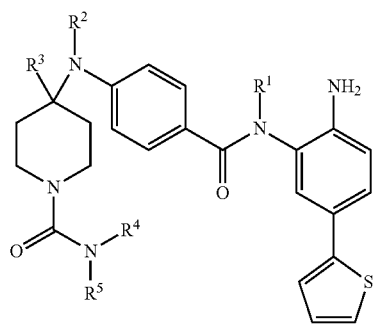

or a pharmaceutically acceptable salt thereof.

In an embodiment of the compound of Formula IIIa, $R^2$ is H.

In an embodiment of the compound of Formula IIIa, $R^3$ is H, methyl, or isopropyl. In a further embodiment of the compound of Formula IIIa, $R^3$ is H.

In an embodiment of the compound of Formula III, $R^4$ is H and $R^5$ is $C_1$-$C_6$-alkyl.

In an embodiment of the compound of Formula IIIa, $R^4$ and $R^5$ together form a heterocyclyl selected from the group consisting of morpholinyl, piperidinyl, piperazinyl, and pyrrolidinyl, wherein the morpholinyl, piperidinyl, piperazinyl, and pyrrolidinyl are optionally substituted by 1 or 2 of $C_1$-$C_6$-alkyl, halo, or hydroxy.

In another embodiment of the compound of Formula IIIa,
R¹ is H;
R² is H; and
R³ is H.
In another embodiment of the compound of Formula IIIa,
R¹ is H;
R² is H;
R³ is H; and
R⁴ and R⁵ together form a heterocyclyl selected from the group consisting of morpholinyl, piperidinyl, piperazinyl, and pyrrolidinyl, wherein the morpholinyl, piperidinyl, piperazinyl, and pyrrolidinyl are optionally substituted by 1 or 2 of $C_1$-$C_6$-alkyl, halo, or hydroxy.

In another aspect, provided herein is a compound selected from any of the compounds presented in Table 1:

TABLE 1

| ID | Structure | IC50 (nM) | | |
|---|---|---|---|---|
| | | HDAC1 | HDAC2 | HDAC3 |
| 001 | 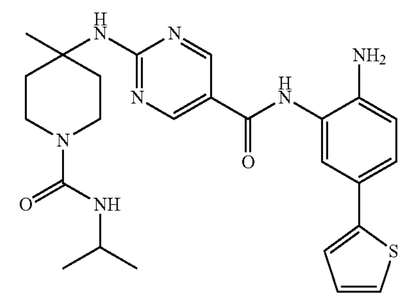 [SMILES: CC(C)NC(=O)N1CCC(C)(Nc2ncc(C(=O)Nc3cc(-c4cccs4)ccc3N)cn2)CC1] | 6.5 | 38 | 427 |
| 002 | 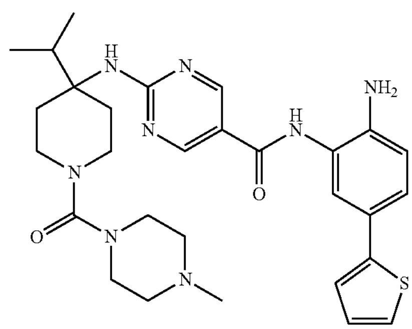 [SMILES: CC(C)C1(Nc2ncc(C(=O)Nc3cc(-c4cccs4)ccc3N)cn2)CCN(C(=O)N2CCN(C)CC2)CC1] | 7 | 28 | 203 |
| 003 | 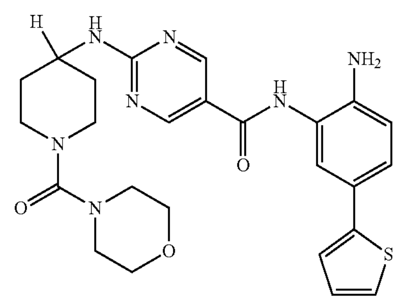 [SMILES: Nc1ccc(-c2cccs2)cc1NC(=O)c1cnc(NC2CCN(C(=O)N3CCOCC3)CC2)nc1] | 15 | 56 | 204 |
| 004 | 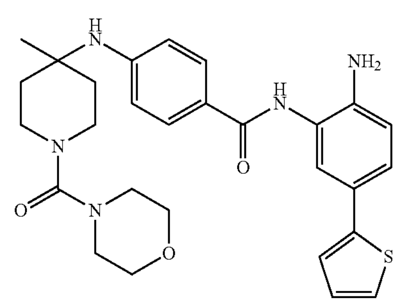 [SMILES: CC1(Nc2ccc(C(=O)Nc3cc(-c4cccs4)ccc3N)cc2)CCN(C(=O)N2CCOCC2)CC1] | 2.0 | 21 | 286 |

TABLE 1-continued

| ID | Structure | IC50 (nM) | | |
|---|---|---|---|---|
| | | HDAC1 | HDAC2 | HDAC3 |
| 005 | 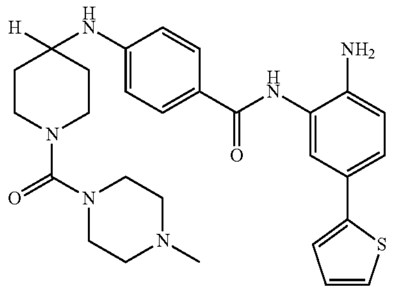 [SMILES: CN1CCN(C(=O)N2CCC(Nc3ccc(C(=O)Nc4cc(-c5cccs5)ccc4N)cc3)CC2)CC1] | 1.2 | 4.9 | 82 |
| 006 | 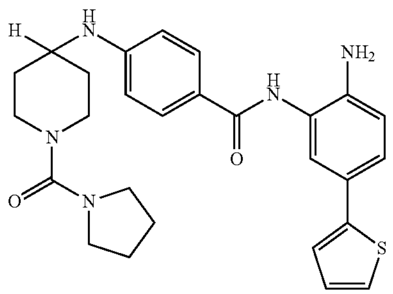 | 4.7 | 22 | 274 |
| 007 | 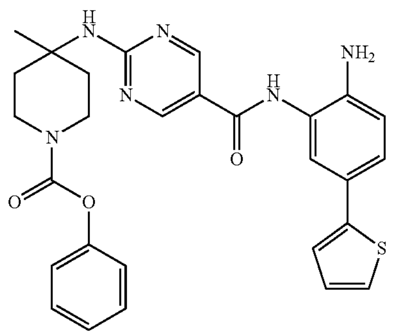 [SMILES: CC1(Nc2ncc(C(=O)Nc3cc(-c4cccs4)ccc3N)cn2)CCN(C(=O)Oc2ccccc2)CC1] | 118 | 703 | 929 |
| 008 | 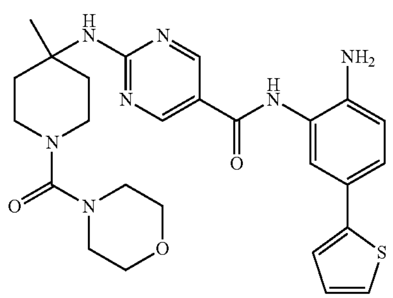 [SMILES: CC1(Nc2ncc(C(=O)Nc3cc(-c4cccs4)ccc3N)cn2)CCN(C(=O)N2CCOCC2)CC1] | 9 | 37 | 124 |
| 009 | 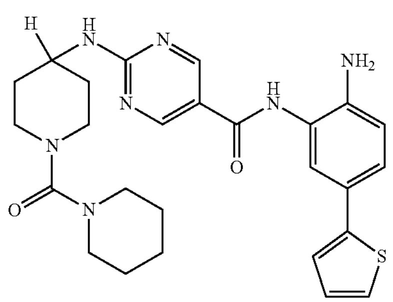 [SMILES: Nc1ccc(-c2cccs2)cc1NC(=O)c1cnc(NC2CCN(C(=O)N3CCCCC3)CC2)nc1] | 32 | 145 | 250 |

TABLE 1-continued
| ID | Structure | IC50 (nM) | | |
|---|---|---|---|---|
| | | HDAC1 | HDAC2 | HDAC3 |
| 010 | 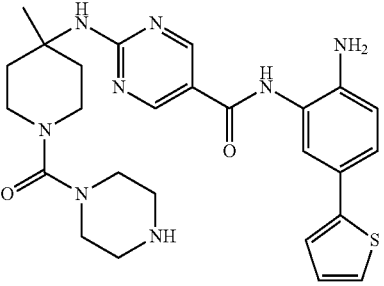 [SMILES: CC1(Nc2ncc(C(=O)Nc3cc(-c4cccs4)ccc3N)cn2)CCN(C(=O)N2CCNCC2)CC1] | 7.3 | 26 | 195 |
| 011 | 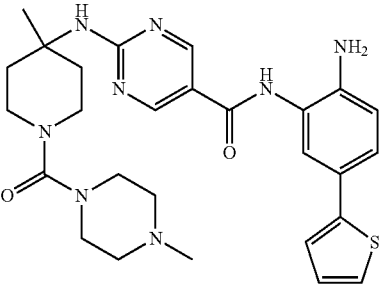 [SMILES: CN1CCN(C(=O)N2CCC(C)(Nc3ncc(C(=O)Nc4cc(-c5cccs5)ccc4N)cn3)CC2)CC1] | 8.5 | 32 | 201 |
| 012 | 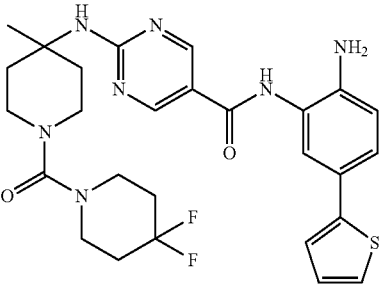 [SMILES: CC1(Nc2ncc(C(=O)Nc3cc(-c4cccs4)ccc3N)cn2)CCN(C(=O)N2CCC(F)(F)CC2)CC1] | 19 | 177 | 1269 |
| 013 | 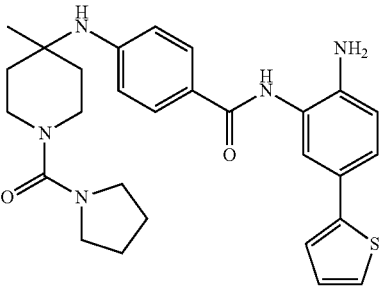 [SMILES: CC1(Nc2ccc(C(=O)Nc3cc(-c4cccs4)ccc3N)cc2)CCN(C(=O)N2CCCC2)CC1] | 4 | 14 | 412 |
| 014 | 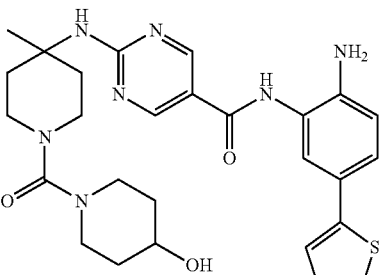 | 63 | 299 | >2000 |

TABLE 1-continued

| ID | Structure | IC50 (nM) | | |
|---|---|---|---|---|
| | | HDAC1 | HDAC2 | HDAC3 |
| 015 | 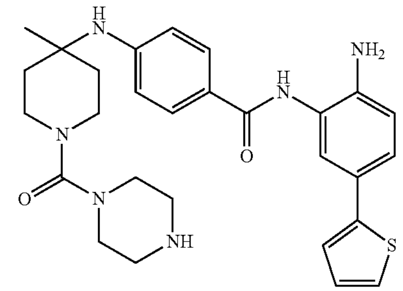 [SMILES: CC1(Nc2ccc(C(=O)Nc3cc(-c4cccs4)ccc3N)cc2)CCN(C(=O)N2CCNCC2)CC1] | 3.2 | 12 | 149 |
| 016 | 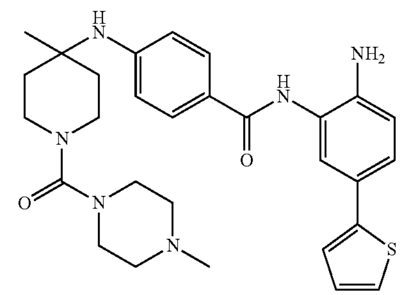 [SMILES: CN1CCN(C(=O)N2CCC(C)(Nc3ccc(C(=O)Nc4cc(-c5cccs5)ccc4N)cc3)CC2)CC1] | 3.2 | 13 | 145 |
| 017 | 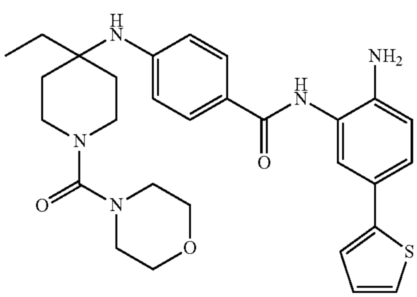 | 18 | 99 | 1739 |
| 018 | 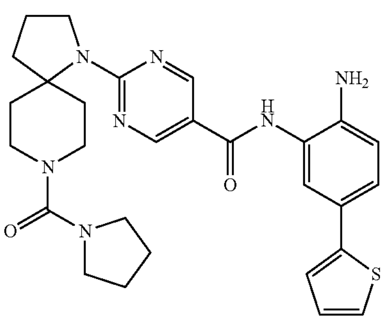 [SMILES: Nc1ccc(-c2cccs2)cc1NC(=O)c1cnc(N2CCCC23CCN(C(=O)N2CCCC2)CC3)nc1] | 12 | 78 | 516 |
| 019 | 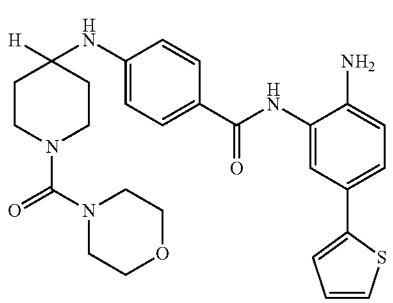 | 0.9 | 4.2 | 43 |

TABLE 1-continued

| ID | Structure | IC50 (nM) | | |
|---|---|---|---|---|
| | | HDAC1 | HDAC2 | HDAC3 |
| 020 | 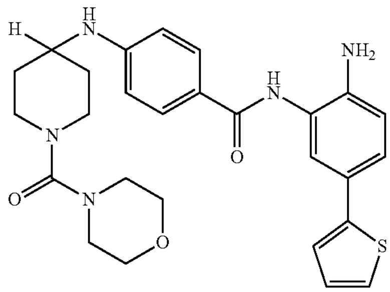 | 3.7 | 17 | 304 |
| 021 | 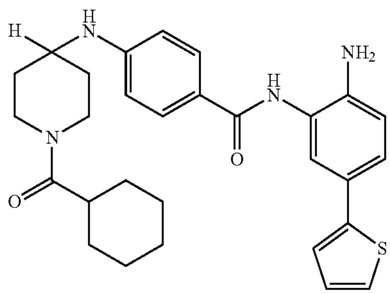 | 15 | 72 | 555 |
| 022 | 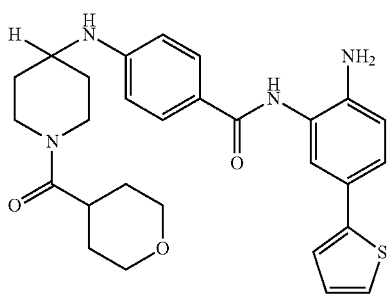 [SMILES: Nc1ccc(-c2cccs2)cc1NC(=O)c1ccc(NC2CCN(C(=O)C3CCOCC3)CC2)cc1] | 5 | 18 | 203 |
| 023 | 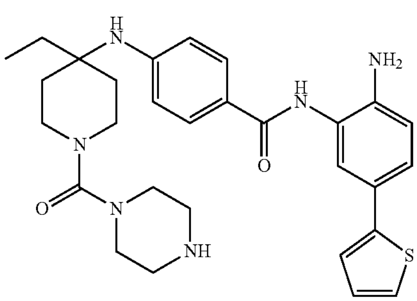 [SMILES: CCC1(Nc2ccc(C(=O)Nc3cc(-c4cccs4)ccc3N)cc2)CCN(C(=O)N2CCNCC2)CC1] | 3.9 | 20 | 267 |
| 024 | 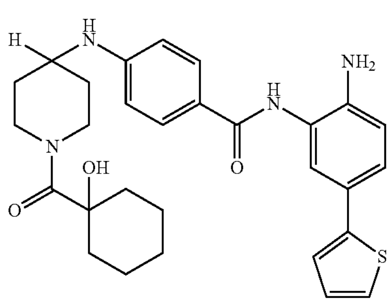 [SMILES: Nc1ccc(-c2cccs2)cc1NC(=O)c1ccc(NC2CCN(C(=O)C3(O)CCCCC3)CC2)cc1] | 6 | 26 | 287 |

TABLE 1-continued
| ID | Structure | IC50 (nM) | | |
|---|---|---|---|---|
| | | HDAC1 | HDAC2 | HDAC3 |
| 025 | 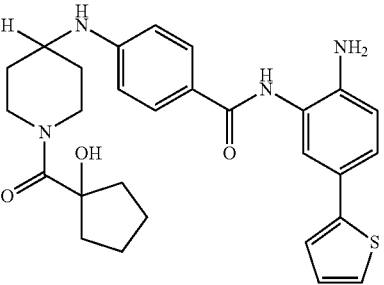 [SMILES: Nc1ccc(-c2cccs2)cc1NC(=O)c1ccc(NC2CCN(C(=O)C3(O)CCCC3)CC2)cc1] | 7 | 26 | 355 |
| 026 | 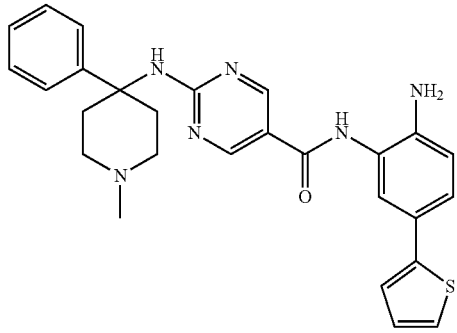 [SMILES: CN1CCC(Nc2ncc(C(=O)Nc3cc(-c4cccs4)ccc3N)cn2)(c2ccccc2)CC1] | 10 | 72 | 315 |
| 027 | 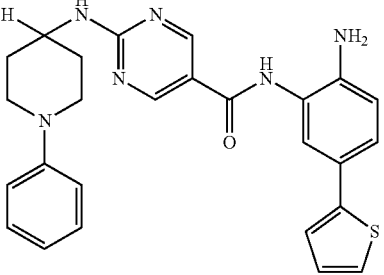 | 121 | 690 | >2000 |
| 028 | 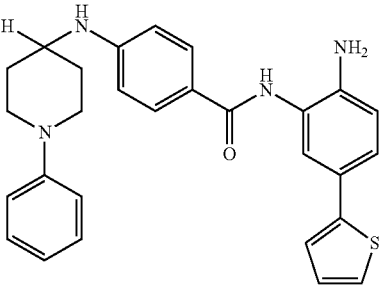 [SMILES: Nc1ccc(-c2cccs2)cc1NC(=O)c1ccc(NC2CCN(c3ccccc3)CC2)cc1] | 74 | 443 | >2000 |
| 029 | 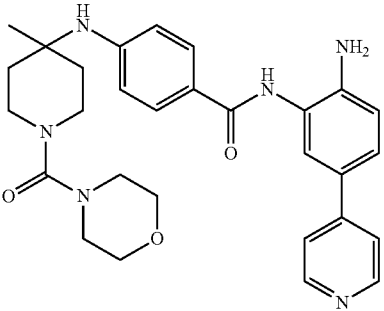 [SMILES: CC1(Nc2ccc(C(=O)Nc3cc(-c4ccncc4)ccc3N)cc2)CCN(C(=O)N2CCOCC2)CC1] | 12 | 17 | 541 |

TABLE 1-continued
| ID | Structure | IC50 (nM) | | |
|---|---|---|---|---|
| | | HDAC1 | HDAC2 | HDAC3 |
| 030 | 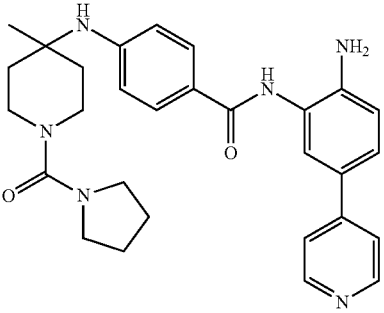 [SMILES: CC1(Nc2ccc(C(=O)Nc3cc(-c4ccncc4)ccc3N)cc2)CCN(C(=O)N2CCCC2)CC1] | 7.1 | 9.4 | 466 |
| 031 | 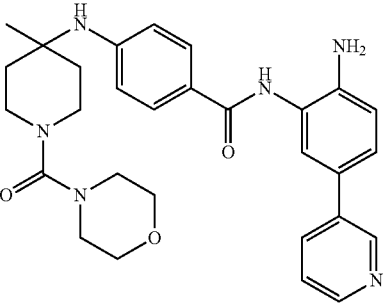 [SMILES: CC1(Nc2ccc(C(=O)Nc3cc(-c4cccnc4)ccc3N)cc2)CCN(C(=O)N2CCOCC2)CC1] | 91 | 71 | 264 |
| 032 | 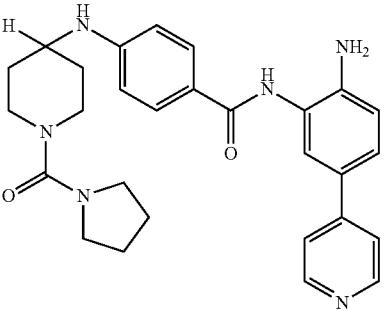 | 17 | 20 | 397 |
| 033 | 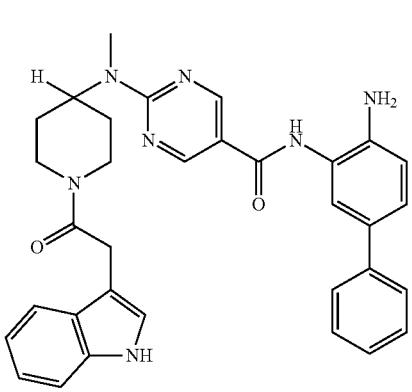 [SMILES: CN(c1ncc(C(=O)Nc2cc(-c3ccccc3)ccc2N)cn1)C1CCN(C(=O)Cc2c[nH]c3ccccc23)CC1] | 48 | 211 | >2000 |

TABLE 1-continued
| ID | Structure | IC50 (nM) | | |
|---|---|---|---|---|
| | | HDAC1 | HDAC2 | HDAC3 |
| 034 | 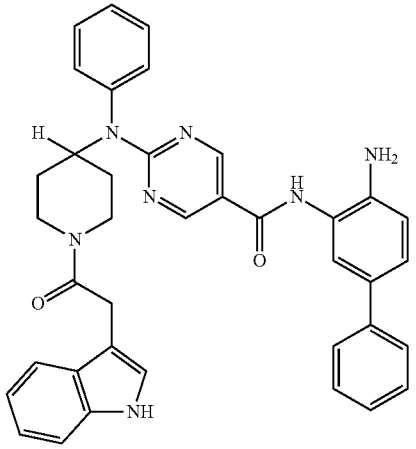 [SMILES: Nc1ccc(-c2ccccc2)cc1NC(=O)c1cnc(N(c2ccccc2)C2CCN(C(=O)Cc3c[nH]c4ccccc34)CC2)nc1] | 93 | 346 | >2000 |
| 035 | 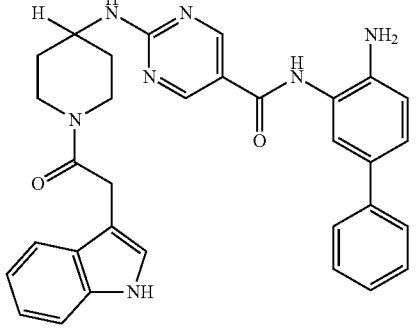 | 22 | 196 | 1398 |
| 036 | 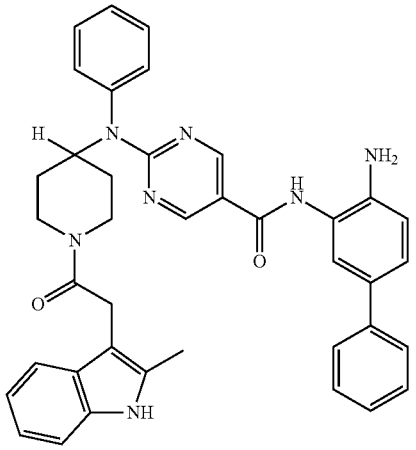 [SMILES: Cc1[nH]c2ccccc2c1CC(=O)N1CCC(N(c2ccccc2)c2ncc(C(=O)Nc3cc(-c4ccccc4)ccc3N)cn2)CC1] | 74 | 996 | >2000 |

TABLE 1-continued

| ID | Structure | IC50 (nM) | | |
|----|-----------|-----------|---|---|
| | | HDAC1 | HDAC2 | HDAC3 |
| 037 | 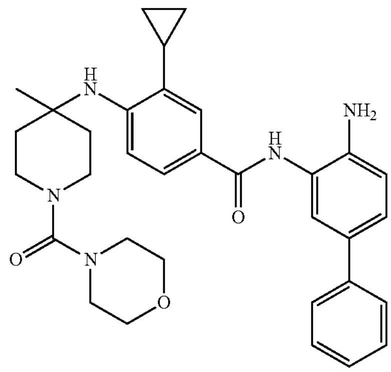 [SMILES: CC1(Nc2ccc(C(=O)Nc3cc(-c4ccccc4)ccc3N)cc2C2CC2)CCN(C(=O)N2CCOCC2)CC1] | 432 | 377 | 1855 |
| 038 | 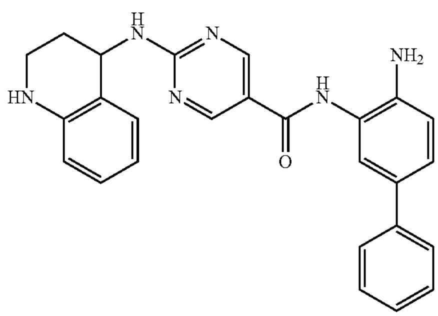 [SMILES: Nc1ccc(-c2ccccc2)cc1NC(=O)c1cnc(NC2CCNc3ccccc32)nc1] | 101 | 319 | >2000 |
| 039 | 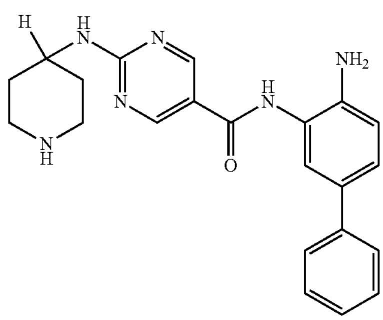 [SMILES: Nc1ccc(-c2ccccc2)cc1NC(=O)c1cnc(NC2CCNCC2)nc1] | 17 | 59 | 321 |
| 040 | 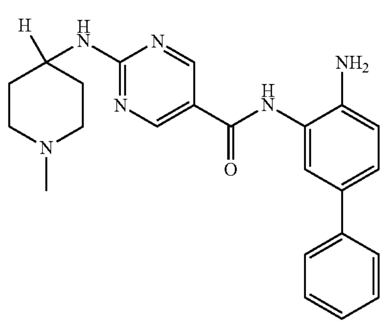 [SMILES: CN1CCC(Nc2ncc(C(=O)Nc3cc(-c4ccccc4)ccc3N)cn2)CC1] | 8 | 39 | 277 |

TABLE 1-continued

| ID | Structure | IC50 (nM) HDAC1 | HDAC2 | HDAC3 |
|---|---|---|---|---|
| 041 | 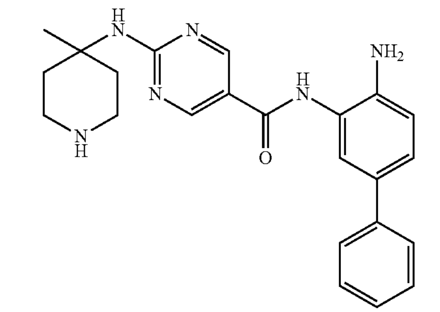 [SMILES: CC1(Nc2ncc(C(=O)Nc3cc(-c4ccccc4)ccc3N)cn2)CCNCC1] | 14 | 26 | 252 |
| 042 | | 210 | 714 | >2000 | and pharmaceutically acceptable salts thereof.

In another aspect, provided herein is a compound selected from any of the compounds presented in Table 1a:

TABLE 1a

| ID | Structure |
|---|---|
| 001 | 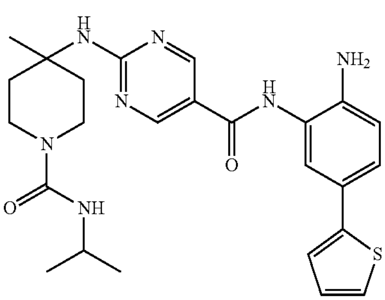 [SMILES: CC(C)NC(=O)N1CCC(C)(Nc2ncc(C(=O)Nc3cc(-c4cccs4)ccc3N)cn2)CC1] |
| 002 | 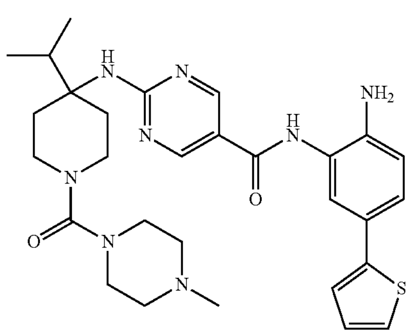 [SMILES: CC(C)C1(Nc2ncc(C(=O)Nc3cc(-c4cccs4)ccc3N)cn2)CCN(C(=O)N2CCN(C)CC2)CC1] |

TABLE 1a-continued

| ID | Structure |
|---|---|
| 004 | 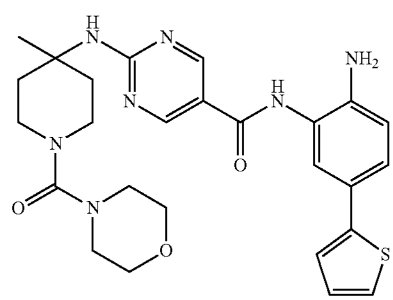 [SMILES: CC1(Nc2ncc(C(=O)Nc3cc(-c4cccs4)ccc3N)cn2)CCN(C(=O)N2CCOCC2)CC1] |
| 005 | 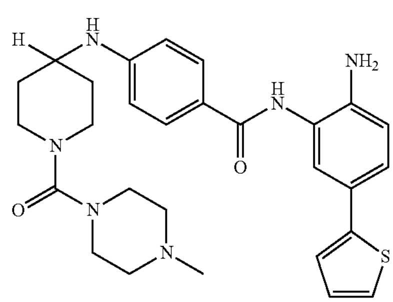 [SMILES: CN1CCN(C(=O)N2CCC(Nc3ccc(C(=O)Nc4cc(-c5cccs5)ccc4N)cc3)CC2)CC1] |

TABLE 1a-continued
| ID | Structure |
|---|---|
| 006 | 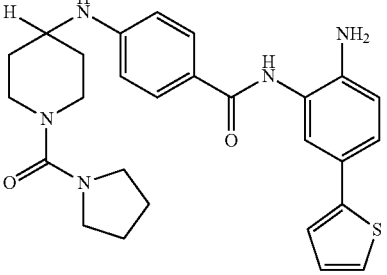 |
| 007 | 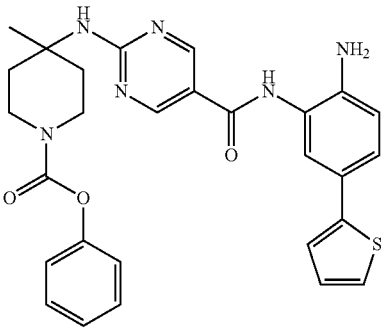 [SMILES: CC1(Nc2ncc(C(=O)Nc3cc(-c4cccs4)ccc3N)cn2)CCN(C(=O)Oc2ccccc2)CC1] |
| 008 | 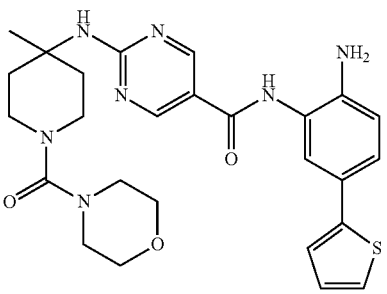 |
| 009 | 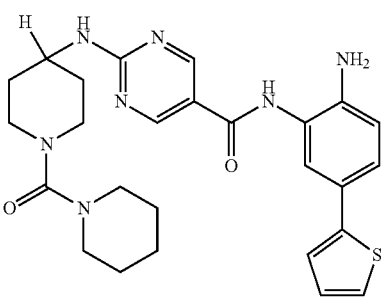 |
| 012 | 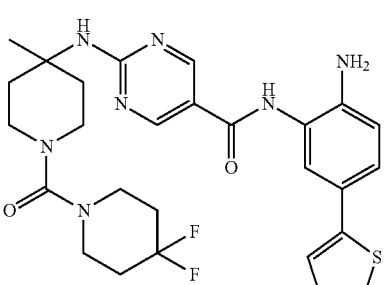 |
| 013 | 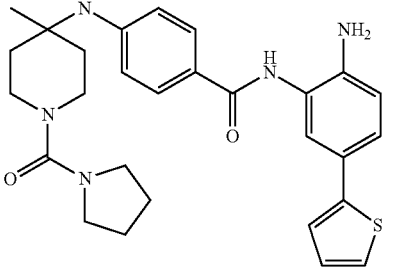 |
| 014 | 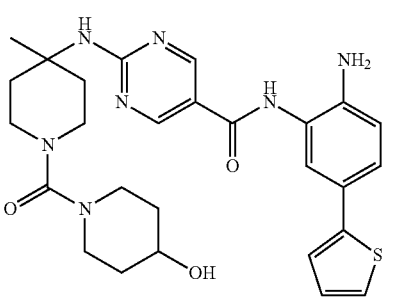 [SMILES: CC1(Nc2ncc(C(=O)Nc3cc(-c4cccs4)ccc3N)cn2)CCN(C(=O)N2CCC(O)CC2)CC1] |
| 015 | 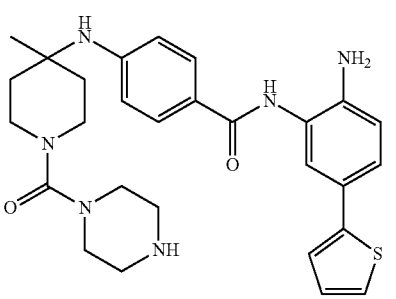 [SMILES: CC1(Nc2ccc(C(=O)Nc3cc(-c4cccs4)ccc3N)cc2)CCN(C(=O)N2CCNCC2)CC1] |
| 016 | 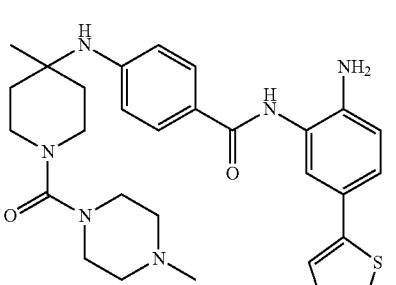 |
| 017 | 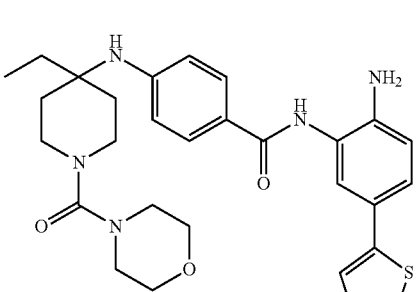 |

TABLE 1a-continued
| ID | Structure |
|----|-----------|
| 018 | 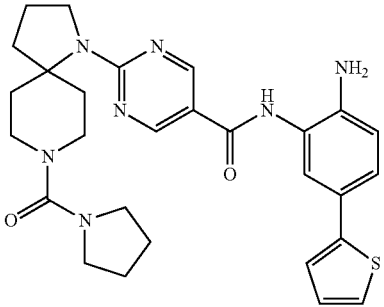 |
| 019 | 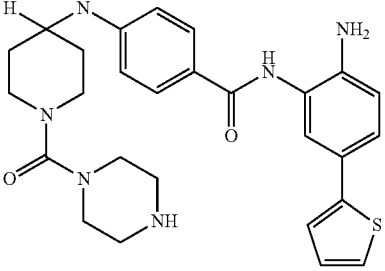 |
| 020 | 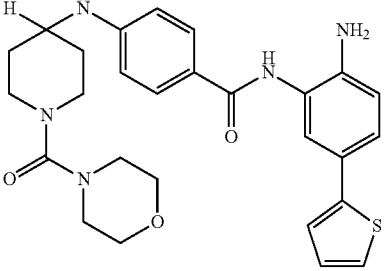 |
| 021 | 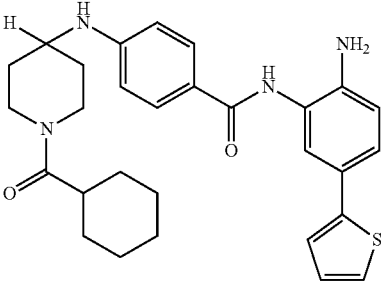 |
| 022 | 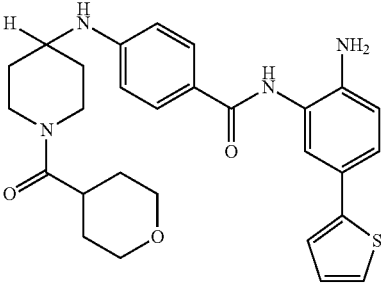 [SMILES: Nc1ccc(-c2cccs2)cc1NC(=O)c1ccc(NC2CCN(C(=O)C3CCOCC3)CC2)cc1] |
| 023 | 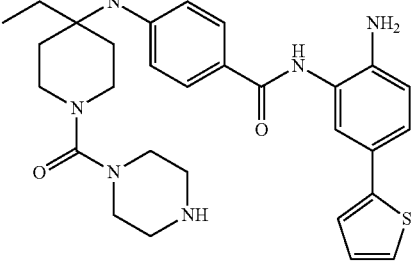 |
| 024 | 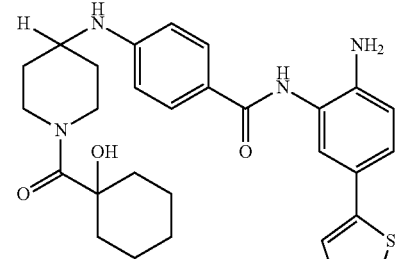 |
| 025 | 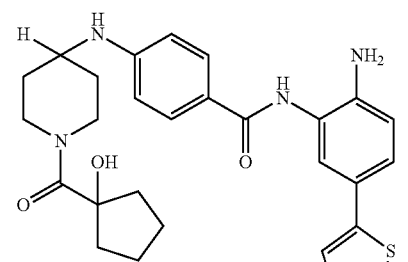 |
| 026 | 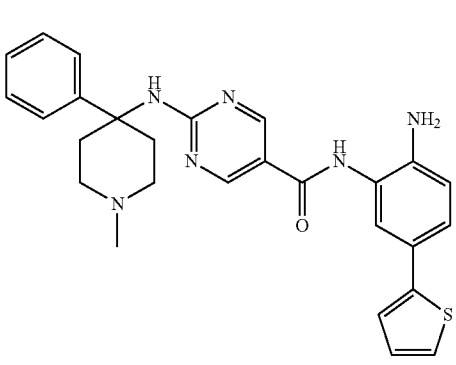 [SMILES: CN1CCC(Nc2ncc(C(=O)Nc3cc(-c4cccs4)ccc3N)cn2)(c2ccccc2)CC1] |
| 027 | 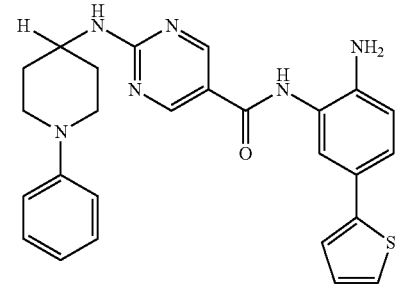 [SMILES: Nc1ccc(-c2cccs2)cc1NC(=O)c1cnc(NC2CCN(c3ccccc3)CC2)nc1] |

TABLE 1a-continued

| ID | Structure |
|---|---|
| 028 | (structure) |
| 030 | (structure) |
| 031 | (structure) |
| 032 | (structure) |
| 033 | (structure) |
| 034 | (structure) |
| 035 | (structure) |
| 036 | (structure) |

TABLE 1a-continued

| ID | Structure |
|---|---|
| 037 | 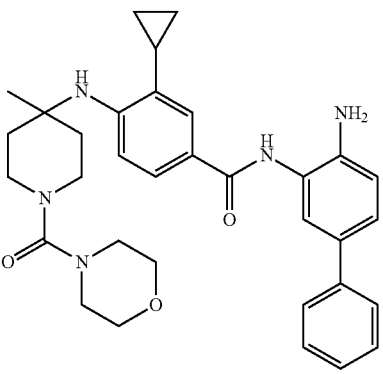 [SMILES: CC1(Nc2ccc(C(=O)Nc3cc(-c4ccccc4)ccc3N)cc2C2CC2)CCN(C(=O)N2CCOCC2)CC1] |
| 038 | 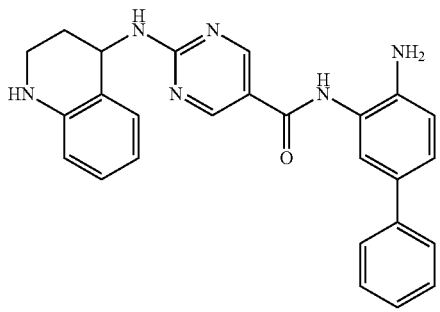 [SMILES: Nc1ccc(-c2ccccc2)cc1NC(=O)c1cnc(NC2CCNc3ccccc32)nc1] |
| 039 | 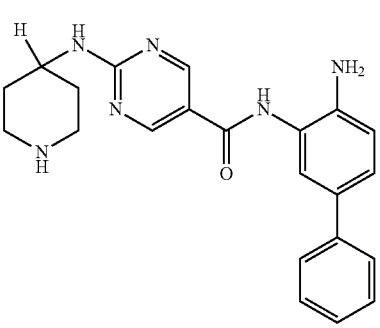 [SMILES: Nc1ccc(-c2ccccc2)cc1NC(=O)c1cnc(NC2CCNCC2)nc1] |
| 040 | 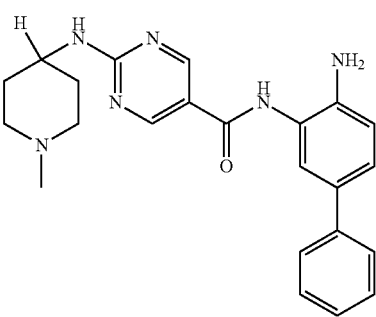 [SMILES: CN1CCC(Nc2ncc(C(=O)Nc3cc(-c4ccccc4)ccc3N)cn2)CC1] |
| 041 | 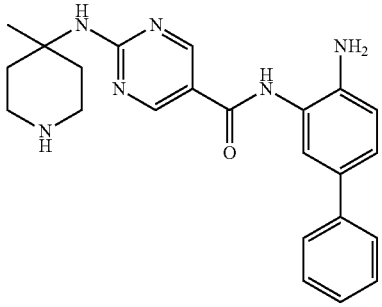 [SMILES: CC1(Nc2ncc(C(=O)Nc3cc(-c4ccccc4)ccc3N)cn2)CCNCC1] |
| 042 | 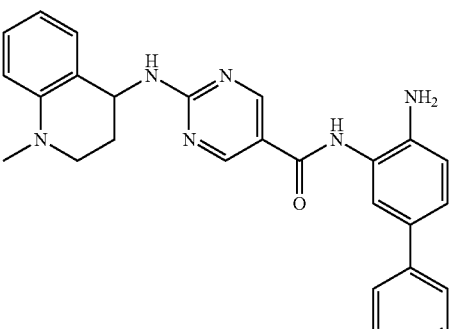 | and pharmaceutically acceptable salts thereof.

In preferred embodiments, the compounds of the instant invention have one or more of the following properties: the compound is capable of inhibiting at least one histone deacetylase (HDAC); the compound is capable of inhibiting HDAC1 and/or HDAC2; the compound selectively inhibits HDAC1 and/or HDAC2 over other HDACs.

Another object of the present invention is the use of a compound as described herein (e.g., of any formulae herein) in the manufacture of a medicament for use in the treatment of a disorder or disease herein. Another object of the present invention is the use of a compound as described herein (e.g., of any formulae herein) for use in the treatment of a disorder or disease herein.

In another aspect, provided herein is a method of synthesizing a compound of Formula I, Formula II, Formula IIa, Formula III, or Formula IIIa, a compound presented in Table 1, a compound presented in Table 1a, or pharmaceutically acceptable salts thereof. The synthesis of the compounds of the invention can be found in the Examples below. An embodiment is therefore a method of making a compound of any of the formulae herein using any one, or combination of, reactions delineated herein. The method can include the use of one or more intermediates or chemical reagents delineated herein.

In another aspect, provided herein is an isotopically labeled compound of any of the formulae delineated herein. Such compounds have one or more isotope atoms which can be radioactive (e.g., $^3$H, $^2$H, $^{14}$C, $^{13}$C, $^{35}$S, $^{32}$P, $^{125}$I, and $^{131}$I) introduced into the compound. Such compounds are useful for drug metabolism studies and diagnostics, as well as therapeutic applications.

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry," 3rd edition, John Wiley and Sons, Inc., 1999, and subsequent editions thereof.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxan, tetrahydrofuran or methanol.

In addition, compounds of this invention can have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that can be defined, in terms of absolute stereochemistry, as (R)- or (S)-, or as (D)- or (L)- for amino acids. All such isomeric forms of these compounds are expressly included in the present invention. Optical isomers can be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., "Enantiomers, Racemates, and Resolutions" (John Wiley & Sons, 1981). The compounds of this invention can also be represented in multiple tautomeric forms, in such instances, the invention expressly includes all tautomeric forms of the compounds described herein. When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans can be cis, trans, or a mixture of the two in any proportion. All such isomeric forms of such compounds are expressly included in the present invention.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps can be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired compounds of the present invention. Synthetic chemistry transformations and protecting group methodologies (protection and deprotection) useful in synthesizing the compounds described herein are known in the art.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Pharmaceutical Compositions

Also provided herein is a pharmaceutical composition comprising a compound of the instant invention, or a pharmaceutically acceptable salt thereof, together with a pharmaceutically acceptable carrier.

In an aspect, provided herein is a pharmaceutical composition comprising any of the compounds of the instant invention (i.e., compounds of Formula I, Formula II, Formula IIa, Formula III, or Formula IIIa, a compound presented in Table 1, a compound presented in Table 1a, or pharmaceutically acceptable salts thereof), together with a pharmaceutically acceptable carrier.

In an aspect, provided herein is a pharmaceutical composition comprising a compound of Formula I, or a pharmaceutically acceptable salt thereof, together with a pharmaceutically acceptable carrier.

In an aspect, provided herein is a pharmaceutical composition comprising a compound of Formula II, or a pharmaceutically acceptable salt thereof, together with a pharmaceutically acceptable carrier.

In an aspect, provided herein is a pharmaceutical composition comprising a compound of Formula IIa, or a pharmaceutically acceptable salt thereof, together with a pharmaceutically acceptable carrier.

In an aspect, provided herein is a pharmaceutical composition comprising a compound of Formula III, or a pharmaceutically acceptable salt thereof, together with a pharmaceutically acceptable carrier.

In an aspect, provided herein is a pharmaceutical composition comprising a compound of Formula IIIa, or a pharmaceutically acceptable salt thereof, together with a pharmaceutically acceptable carrier.

In an aspect, provided herein is a pharmaceutical composition comprising a compound of Table 1, or pharmaceutically acceptable salts thereof, together with a pharmaceutically acceptable carrier.

In an aspect, provided herein is a pharmaceutical composition comprising a compound of Table 1a, or pharmaceutically acceptable salts thereof, together with a pharmaceutically acceptable carrier.

In an aspect, provided herein is a pharmaceutical composition comprising Compound 005, or a pharmaceutically acceptable salt thereof, together with a pharmaceutically acceptable carrier.

These pharmaceutical compositions comprise a therapeutically effective amount of a compound of the present invention formulated together with one or more pharmaceutically acceptable carriers. The term "pharmaceutically acceptable carrier" means a non-toxic, inert solid, semi-solid or liquid filler, diluent, encapsulating material or formulation auxiliary of any type. The pharmaceutical compositions can be administered to humans and other animals orally, rectally, parenterally, intracisternally, intravaginally, intraperitoneally, topically (as by powders, ointments, or drops), buccally, or as an oral or nasal spray.

Compounds of the invention can be administered as pharmaceutical compositions by any conventional route, in particular enterally, for example, orally, e.g., in the form of tablets or capsules, or parenterally, e.g., in the form of injectable solutions or suspensions, topically, e.g., in the form of lotions, gels, ointments or creams, or in a nasal or suppository form.

Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions can be sterilized and/or contain adjuvants, such as preserving, stabilizing, wetting or emulsifying agents, solution promoters, salts for regulating the osmotic pressure and/or buffers. In addition, they can also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations can also be used. Suitable formulations for topical application, e.g., to the skin and eyes, are preferably aqueous solutions, ointments, creams or gels well-known in the art. Such can contain solubilizers, stabilizers, tonicity enhancing agents, buffers and preservatives.

The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose or starch. Such dosage forms can also comprise, as is normal practice, additional substances other than inert diluents, e.g., tableting lubricants and other tableting aids such a magnesium stearate and microcrystalline cellulose. In the case of capsules, tablets and pills, the dosage forms can also comprise buffering agents.

Methods for Treating

Provided herein are methods for treating or preventing disorders in a subject, such as a human or other animal, by administering to the subject a therapeutically effective amount of a compound of the invention, in such amounts and for such time as is necessary to achieve the desired result. The term "therapeutically effective amount" of a compound of the invention means a sufficient amount of the compound so as to decrease the symptoms of a disorder in a subject. As is well understood in the medical arts a therapeutically effective amount of a compound of this invention will be at a reasonable benefit/risk ratio applicable to any medical treatment.

The term "treating" or "treatment" as used herein comprises relieving, reducing or alleviating at least one symptom in a subject or effecting a delay of progression of a disease. For example, treatment can be the diminishment of one or several symptoms of a disorder or complete eradication of a disorder, such as cancer. Within the meaning of the present disclosure, the term "treat" also denotes to arrest, delay the onset (i.e., the period prior to clinical manifestation of a disease) and/or reduce the risk of developing or worsening a disease. The term "protect" is used herein to mean prevent, delay, or treat, or all, as appropriate, development, continuance or aggravation of a disease in a subject, e.g., a mammal or human. The term "prevent", "preventing" or "prevention" as used herein comprises the prevention of at least one symptom associated with or caused by the state, disease or disorder being prevented.

In general, compounds of the invention will be administered in therapeutically effective amounts via any of the usual and acceptable modes known in the art, either singly or in combination with one or more therapeutic agents. A therapeutically effective amount can vary widely depending on the severity of the disease, the age and relative health of the subject, the potency of the compound used and other factors.

In certain embodiments, a therapeutic amount or dose of the compounds of the present invention can range from about 0.1 mg/kg to about 500 mg/kg (about 0.18 mg/m$^2$ to about 900 mg/m$^2$), alternatively from about 1 to about 50 mg/kg (about 1.8 to about 90 mg/m$^2$). In general, treatment regimens according to the present invention comprise administration to a patient in need of such treatment from about 10 mg to about 1000 mg of the compound(s) of this invention per day in single or multiple doses. Therapeutic amounts or doses will also vary depending on route of administration, as well as the possibility of co-usage with other agents.

Upon improvement of a subject's condition, a maintenance dose of a compound, composition or combination of this invention can be administered, if necessary. Subsequently, the dosage or frequency of administration, or both, can be reduced, as a function of the symptoms, to a level at which the improved condition is retained when the symptoms have been alleviated to the desired level, treatment should cease. The subject can, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In one aspect, the invention provides a method of selectively inhibiting the activity of each of HDAC and/or HDAC2 over other HDACs in a subject, comprising administering a compound of Formula I, Formula II, Formula IIa, Formula III, or Formula IIIa, a compound presented in Table 1, a compound presented in Table 1a, or pharmaceutically acceptable salts thereof.

In an embodiment, the compound has a selectivity for each of HDAC1 and/or HDAC2 of about 2 to 1000 (including ranges such as, e.g., 5 to 1000, 10 to 1000, 5 to 100, etc.) fold greater than for other HDACs. In another embodiment, the compound has a selectivity for each of HDAC1 and/or HDAC2 when tested in a HDAC enzyme assay of about 2 to 1000 (including ranges such as, e.g., 5 to 1000, 10 to 1000, 5 to 100, etc.) fold greater than for other HDACs.

In another aspect, the invention provides a method for treating a disease mediated by an HDAC, specifically HDAC1 and/or HDAC2 in a subject comprising administering to the subject a compound of Formula I, Formula II, Formula IIa, Formula III, or Formula IIIa, a compound presented in Table 1, a compound presented in Table 1a, or pharmaceutically acceptable salts thereof. The selective HDAC1 and HDAC2 inhibitors of the present invention have favorable pharmacokinetic profiles (see, e.g., Example 44).

In an aspect, provided herein is a method for treating a disease mediated by HDAC1 and/or HDAC2 in a subject comprising administering to the subject a therapeutically effective amount of compound of Formula I, or a pharmaceutically acceptable salt thereof.

In an aspect, provided herein is a method for treating a disease mediated by HDAC1 and/or HDAC2 in a subject comprising administering to the subject a therapeutically effective amount of compound of Formula II, or a pharmaceutically acceptable salt thereof.

In an aspect, provided herein is a method for treating a disease mediated by HDAC1 and/or HDAC2 in a subject comprising administering to the subject a therapeutically effective amount of compound of Formula IIa, or a pharmaceutically acceptable salt thereof.

In an aspect, provided herein is a method for treating a disease mediated by HDAC1 and/or HDAC2 in a subject comprising administering to the subject a therapeutically effective amount of compound of Formula III, or a pharmaceutically acceptable salt thereof.

In an aspect, provided herein is a method for treating a disease mediated by HDAC1 and/or HDAC2 in a subject comprising administering to the subject a therapeutically effective amount of compound of Formula IIIa, or a pharmaceutically acceptable salt thereof.

In an aspect, provided herein is a method for treating a disease mediated by HDAC1 and/or HDAC2 in a subject comprising administering to the subject a therapeutically effective amount of compound of Table 1, or pharmaceutically acceptable salts thereof.

In an aspect, provided herein is a method for treating a disease mediated by HDAC1 and/or HDAC2 in a subject comprising administering to the subject a therapeutically effective amount of compound of Table 1a, or pharmaceutically acceptable salts thereof.

In an aspect, provided herein is a method for treating a disease mediated by HDAC1 and/or HDAC2 in a subject comprising administering to the subject a therapeutically effective amount of Compound 005, or a pharmaceutically acceptable salt thereof.

Inhibition of HDAC1 and HDAC2 is sufficient to derepress fetal globin. In cultured human CD34+ bone marrow cells undergoing erythroid differentiation, these compounds can induce a dose dependent increase in fetal hemoglobin expression (see, e.g., Example 45).

Thus, the compounds are capable of derepressing fetal globin through HDAC inhibition. Accordingly, in an embodiment, the compounds are able to treat a subject suffering from or susceptible to a hemoglobinopathy. In a preferred embodiment, the compounds are able to treat sickle-cell disease or beta-thalassemia.

In another embodiment, the compounds of the invention are useful in the treatment of myelodysplastic syndromes.

In certain embodiments, the compounds of the present invention are useful as anti-cancer agents. The compounds of the invention are capable of inducing apoptosis in cancer cells thereby able to treat a disease such as a cancer or proliferation disease. In an embodiment, the compound of the invention can be useful in the treatment of cancer, by effecting tumor cell death or inhibiting the growth of tumor cells.

In certain embodiments, the cancer is lung cancer, colon and rectal cancer, breast cancer, prostate cancer, liver cancer, pancreatic cancer, brain cancer, kidney cancer, ovarian cancer, stomach cancer, skin cancer, bone cancer, gastric cancer, breast cancer, glioma, glioblastoma, neuroblastom, hepatocellular carcinoma, papillary renal carcinoma, head and neck squamous cell carcinoma, leukemia, lymphomas, myelomas, retinoblastoma, cervical cancer, melanoma and/or skin cancer, bladder cancer, uterine cancer, testicular cancer, esophageal cancer, and solid tumors. In some embodiments, the cancer is lung cancer, colon cancer, breast cancer, neuroblastoma, leukemia, or lymphomas. In other embodiments, the cancer is lung cancer, colon cancer, breast cancer, neuroblastoma, leukemia, or lymphoma. In a further embodiment, the cancer is non-small cell lung cancer (NSCLC) or small cell lung cancer. In another embodiment, the cancer is neuroblastoma.

In further embodiments, the cancer is a hematologic cancer, such as leukemia or lymphoma. In a certain embodiment, lymphoma is Hodgkins lymphoma or Non Hodgkin's lymphoma. In certain embodiments, leukemia is myeloid, lymphocytic, myelocytic, lymphoblastic, or megakaryotic leukemia. In a particular embodiment, the leukemia is acute myelogenous leukemia and megakaryocytic leukemia.

In another aspect, provided herein is a method for treating sickle cell disease, beta thalassemia, myelodysplastic syndrome, acute myelogenous leukemia, neuroblastoma, or megakaryocytic leukemia in a subject comprising administering to the subject in need thereof a therapeutically effective amount of a compound of Formula I, Formula II, Formula IIa, Formula III, or Formula IIIa, a compound presented in Table 1, a compound presented in Table 1a, or pharmaceutically acceptable salts thereof.

In an aspect, provided herein is a method for treating sickle cell disease, beta thalassemia, myelodysplastic syndrome, acute myelogenous leukemia, neuroblastoma, or megakaryocytic leukemia in a subject comprising administering to the subject a therapeutically effective amount of compound of Formula I, or a pharmaceutically acceptable salt thereof.

In an aspect, provided herein is a method for treating sickle cell disease, beta thalassemia, myelodysplastic syndrome, acute myelogenous leukemia, neuroblastoma, or megakaryocytic leukemia in a subject comprising administering to the subject a therapeutically effective amount of compound of Formula II, or a pharmaceutically acceptable salt thereof.

In an aspect, provided herein is a method for treating sickle cell disease, beta thalassemia, myelodysplastic syndrome, acute myelogenous leukemia, neuroblastoma, or megakaryocytic leukemia in a subject comprising administering to the subject a therapeutically effective amount of compound of Formula IIa, or a pharmaceutically acceptable salt thereof.

In an aspect, provided herein is a method for treating sickle cell disease, beta thalassemia, myelodysplastic syndrome, acute myelogenous leukemia, neuroblastoma, or megakaryocytic leukemia in a subject comprising administering to the subject a therapeutically effective amount of compound of Formula III, or a pharmaceutically acceptable salt thereof.

In an aspect, provided herein is a method for treating sickle cell disease, beta thalassemia, myelodysplastic syndrome, acute myelogenous leukemia, neuroblastoma, or megakaryocytic leukemia in a subject comprising administering to the subject a therapeutically effective amount of a compound of Formula IIIa, or a pharmaceutically acceptable salt thereof.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

Also, as discussed above, the compounds of the invention are selective inhibitors of HDAC1 and/or HDAC2 and, as such, are useful in the treatment of disorders modulated by these histone deacetylases (HDACs). For example, compounds of the invention can be useful in the treatment of cancer (e.g., lung cancer, colon cancer, breast cancer, neuroblastoma, leukemia, or lymphomas, etc.). Accordingly, in yet another aspect, according to the methods for treatment of the present invention, tumor cells are killed, or their growth is inhibited by contacting said tumor cells with an inventive compound or composition, as described herein.

Thus, in another aspect of the invention, methods for the treatment of cancer are provided comprising administering a therapeutically effective amount of an inventive compound (i.e., of any of the formulae herein), as described herein, to a subject in need thereof. In certain embodiments, the subject is identified as in need of such treatment. In certain embodiments, a method for the treatment of cancer is provided comprising administering a therapeutically effective amount of an inventive compound, or a pharmaceutical composition comprising an inventive compound to a subject in need thereof, in such amounts and for such time as is necessary to achieve the desired result. In certain embodiments of the present invention a "therapeutically effective amount" of the inventive compound or pharmaceutical composition is that amount effective for killing or inhibiting the growth of tumor cells. The compounds and compositions, according to the method of the present invention, can be administered using any amount and any route of administration effective for killing or inhibiting the growth of tumor cells. Thus, the expression "amount effective to kill or inhibit the growth of tumor cells," as used herein, refers to a sufficient amount of agent to kill or inhibit the growth of tumor cells. The exact amount required will vary from subject to subject, depending on the species, age, and general condition of the subject, the severity of the infection, the particular anticancer agent, its mode of administration, and the like.

In certain embodiments, the method involves the administration of a therapeutically effective amount of the compound or a pharmaceutically acceptable derivative thereof to a subject (including, but not limited to a human or animal) in need of it. In certain embodiments, the inventive compounds as useful for the treatment of cancer and other proliferative disorders including, but not limited to lung cancer (e.g. non-small cell lung cancer), colon and rectal cancer, breast cancer, prostate cancer, liver cancer, pancreatic cancer, brain cancer, kidney cancer, ovarian cancer, stomach cancer, skin cancer, bone cancer, gastric cancer, breast cancer, glioma, glioblastoma, neuroblastoma, hepatocellular carcinoma, papillary renal carcinoma, head and neck squamous cell carcinoma, leukemia (e.g., CML, AML, CLL, ALL), lymphomas (non-Hodgkin's and Hodgkin's), myelomas, retinoblastoma, cervical cancer, melanoma and/or skin cancer, bladder cancer, uterine cancer, testicular cancer, esophageal cancer, and solid tumors.

In certain embodiments, the invention provides a method for treating of any of the disorders described herein, wherein the subject is a human.

In accordance with the foregoing, the present invention further provides a method for preventing or treating any of the diseases or disorders described above in a subject in need of such treatment, which method comprises administering to said subject a therapeutically effective amount of a compound of the invention or a pharmaceutically acceptable salt thereof. For any of the above uses, the required dosage will vary depending on the mode of administration, the particular condition to be treated and the effect desired.

EXAMPLES

Examples have been set forth below for the purpose of illustration and to describe certain specific embodiments of the invention. However, the scope of the claims is not to be in any way limited by the examples set forth herein. Various changes and modifications to the disclosed embodiments will be apparent to those skilled in the art and such changes and modifications including, without limitation, those relating to the chemical structures, substituents, derivatives, formulations and/or methods of the invention can be made without departing from the spirit of the invention and the scope of the appended claims. Definitions of the variables in the structures in the schemes herein are commensurate with those of corresponding positions in the formulae presented herein.

Example 1

Synthesis of Compound 001

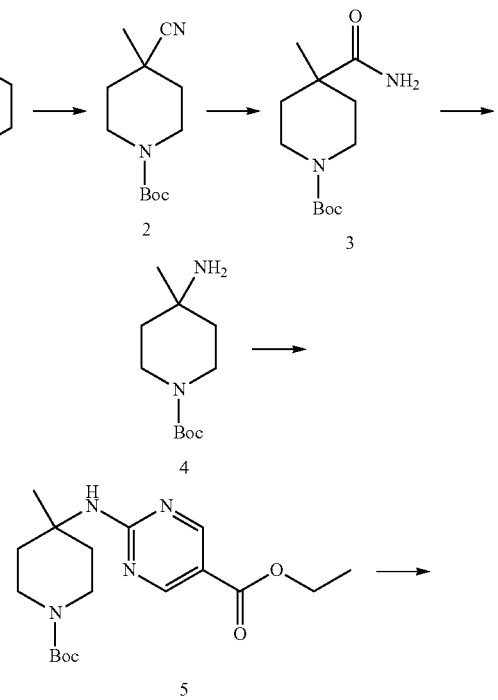

-continued

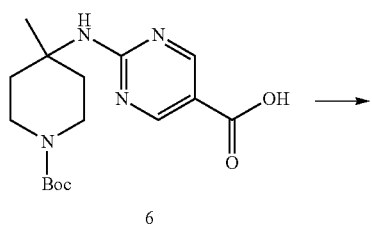

6

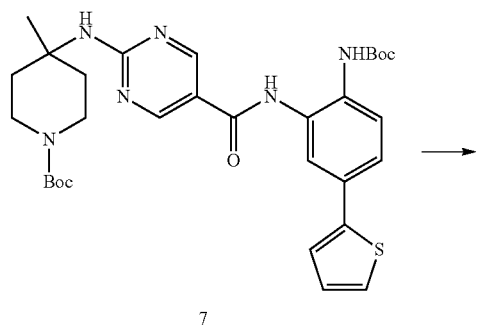

7

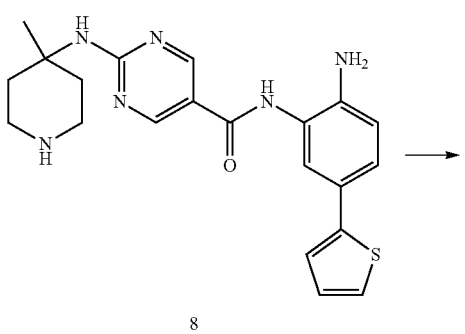

8

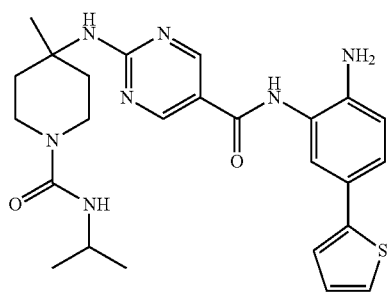

Step 1: Lithium bis(trimethylsilyl)amide (1.0 M solution in THF, 240 ml, 240 mmol) was slowly added into a round-bottomed flask with compound 1 (25 g, 120 mmol) at −76° C. under $N_2$. The reaction was stirred for 4 h at −76° C., and then iodomethane (15 ml, 240 mmol) was injected into the system. The reaction mixture was stirred at −76° C. for 30 min. and then warmed to room temperature and stirred overnight. The reaction mixture was quenched with 150 ml saturated aqueous $NH_4Cl$, diluted with water and extracted with EtOAc (ethyl acetate, or EA). The organic layers were washed with water and brine and dried over sodium sulfate, filtered and concentrated to yield target compound 2 (25 g, 93%) as a light yellow solid.

Step 2: $K_2CO_3$ (31 g, 224 mmol) was added into a solution of compound 2 (25 g, 111 mmol) in DMSO (120 ml). $H_2O_2$ (100 ml) was slowly added to the system at 60° C., and the reaction was stirred overnight at 60° C. The system was then introduced into cold water and extracted with EA. The organic layers were washed with water and brine and dried over sodium sulfate, filtered and concentrated to yield target compound 3 (26 g, 96%) as a white solid.

Step 3: Compound 3 (26 g, 107 mmol) was dissolved with ACN (acetonitrile) (200 ml) and 5N KOH (100 ml). 1,3-dibromo-5,5-dimethylimidazolidine-2,4-dione (15 g, 54 mmol) was then added into the system. The mixture was stirred overnight and concentrated to remove the ACN. The pH of the water phase was adjusted to about 5 with 2N HCl in an ice bath, extracted with EA and separated. The pH of water phase was then adjusted to 10. The precipitate was collected to yield compound 4 as a white solid (16 g, 69%).

Step 4: A solution of compound 4 (2 g, 9.34 mmol), 2-chloropyrimidine (2.6 g, 14.02 mmol) and DIPEA (5.3 g, 28.03 mmol) in 1,4-dioxane (25 ml) was heated at 95° C. overnight. The reaction mixture was then concentrated and purified by silica gel column with EA/PE=1/5 to obtain compound 5 (1.8 g, 53%) as a light yellow solid.

Step 5: A solution of compound 5 (465 mg, 1.28 mmol), 2N NaOH (10 ml, 20 mmol) in THF (10 ml), and EtOH (10 ml) was heated at 55° C. for 2 h. The reaction solution was concentrated and the pH of the water phase was adjusted to between about 5~6. The resulting solution was extracted with EA, the organic layers were washed with water and brine then dried over sodium sulfate, filtered and concentrated to get target compound 6 (400 mg, 93%) as a white solid.

Step 6: A mixture of compound 6 (400 mg, 1.19 mmol), amine (345 mg, 1.19 mmol), EDCI (307 mg, 2.38 mmol) and DMAP (290 mg, 2.38 mmol) in DMF (10 mL) was heated at 55° C. overnight. The mixture was mixed with water and extracted with EA. The organic layers were washed with water and brine then dried over sodium sulfate, filtered and concentrated. The resulting composition was purified by silica gel column with EA/PE=1/2 to yield compound 7 (400 mg, 55%) as a purple solid.

Step 7: A solution of compound 7 (400 mg, 0.65 mmol) with HCl/1,4-dioxane (5 ml, 20 mmol) in 1,4-dioxane (10 ml) was stirred at room temperature overnight. The reaction solution was concentrated and washed with PE to yield target compound 8 (350 mg, 100%) as a gray solid.

Step 8: Compound 8 (162 mg, 0.4 mmol) and Et3N (80 mg, 0.8 mmol) were dissolved in THF (5 ml). Isopropyl Isocyanate (CAS: 1795-48-8, 1.2 eq) was added into the system. The mixture was stirred at room temperature for 2 h. Then the mixture was concentrated and purified by Pre-HPLC to yield Compound 001 (35 mg, 16%). $^1$H NMR (500 MHz, DMSO) δ 9.51 (s, 1H), 8.84 (s, 2H), 7.50 (s, 1H), 7.44 (d, J=2.0 Hz, 1H), 7.35 (d, J=5.1 Hz, 1H), 7.29 (dd, J=8.3, 2.1 Hz, 1H), 7.23 (d, J=2.7 Hz, 1H), 7.05 (dd, J=5.0, 3.6 Hz, 1H), 6.79 (d, J=8.3 Hz, 1H), 6.09 (d, J=7.6 Hz, 1H), 5.20 (s, 2H), 3.53 (d, J=13.6 Hz, 2H), 3.05 (t, J=10.7 Hz, 2H), 2.25 (d, J=13.8 Hz, 2H), 1.53-1.44 (m, 2H), 1.42 (s, 3H), 1.08 (d, J=6.6 Hz, 1H), 1.04 (d, J=6.6 Hz, 6H). LCMS: m/z=494 (M+H).

Example 2

Synthesis of Compound 002

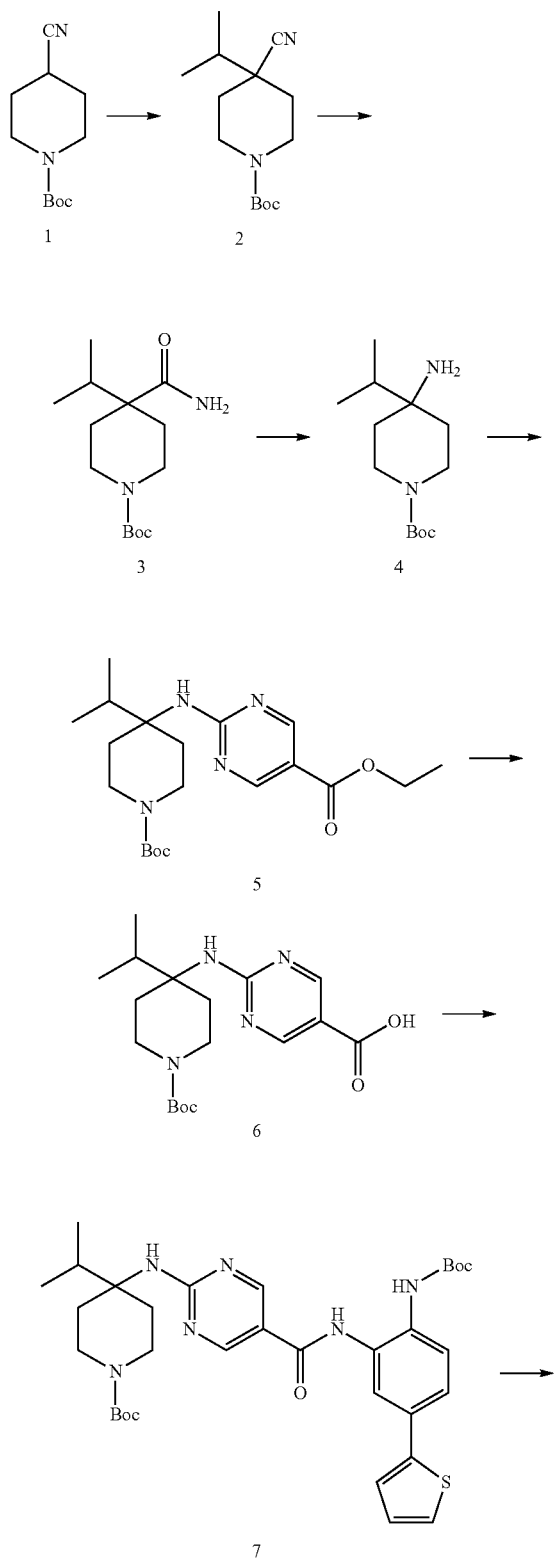

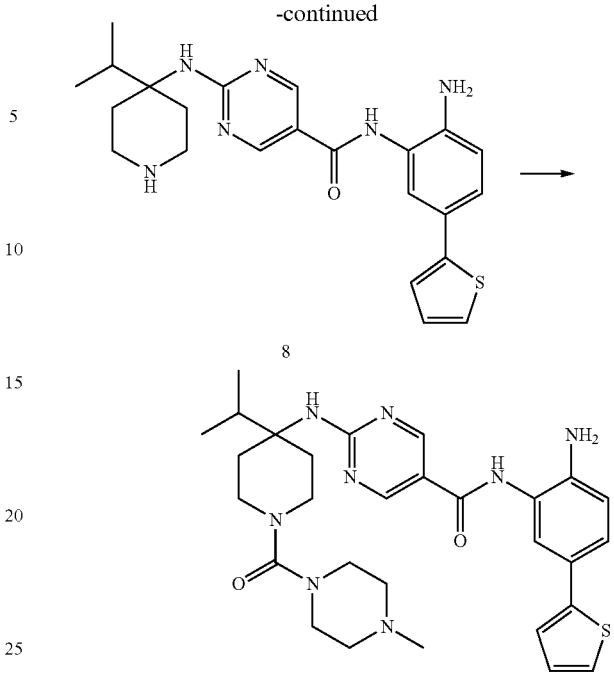

Step 1: To a solution of 1 (3 g, 14.28 mmol) in a boiling flask-3-neck flushed with $N_2$ was added LHDMS (1M, 21.4 ml) at −78° C. The reaction was stirred for 3 h and then 2-iodopropane (3.6 g, 21.43 mmol) was slowly added. The reaction solution was stirred at −78° C., and warmed to room temperature overnight. The mixture was quenched with $H_2O$ (2 ml) and concentrated, dissolved in EA (200 ml), and washed with water (100 ml*2) followed by saturated NaCl (aqueous, 100 ml). The organic layer was concentrated to obtain compound 2 as a brown solid (4 g, 100%).

Step 2: To a solution of 2 (1 g, 3.97 mmol) in DMSO (30 ml) was added $K_2CO_3$ (1.6 g, 11.9 mmol). The resulting reaction mixture was stirred at 60° C. $H_2O_2$ (30% aq, 5 ml) was then added dropwise and stirred for 2 h. EA (100 ml) was added to the mixture which was then washed with water (50 ml*2) and saturated NaCl (aq, 50 ml). Drying with anhydrous $Na_2SO_4$ and concentrating yielded compound 3 as a white solid (1 g, 90%).

Step 3: To a solution of compound 3 (2.7 g, 10 mmol) in ACN (50 ml) was added KOH (4 N, aq, 50 ml) and DBDMH (2.81 g, 5 mmol) at 0° C. The resulting reaction mixture was stirred at room temperature overnight. The mixture was concentrated and 1N HCl was added to adjust the pH to about 6. The mixture was then extracted with EA (50 ml), and the water phase was adjust to about pH 9 by adding KOH. The resulting water phase was extracted with EA (50 ml×3). The EA phase was dried with anhydrous $Na_2SO_4$ and concentrated to yield compound 4 as a colorless liquid (1 g, 40%).

Step 4: A solution of compound 4 (500 mg, 2.06 mmol) and ethyl 2-chloropyrimidine-5-carboxylate (384 mg, 2.06 mmol) in NMP (10 ml) was flushed with $N_2$ and stirred at 140° C. for 1 hour. EA (100 ml) was added to the mixture, which was then washed with water (50 ml×2) and saturated NaCl (aq, 50 ml). Concentration and purification by silica gel chromatography column (PE/EA=5/1) yielded compound 5 as a white solid (120 mg 15%).

Step 5: To a mixture of compound 5 (400 mg) in EtOH (aq, 95%, 5 ml) was added NaOH (2M, 5 ml) and the reaction was stirred at 55° C. for 2 hours. Water (50 ml) was added to the mixture and the pH was adjusted to about 7 with citric acid. The resulting aqueous mixture was extracted with EA (50 ml×3). The EA phase was dried with anhydrous Na₂SO₄ and concentrated to yield compound 6 as a white solid (340 mg, crude).

Step 6: A solution of 6 (100 mg, crude), amine (79.6 mg, 0.274 mmol), EDCI (71 mg, 0.549 mmol), HOAT (75 mg, 0.549 mmol), DMAP (3.4 mg, 0.027 mmol), DIPEA (142 mg, 1.1 mmol) in DMF (5 ml) was stirred at 55° C. overnight. EA (100 ml) was added to the mixture which was then washed with water (50 ml×3) and concentrated to yield compound 7 as a brown oil (200 mg, crude).

Step 7: To a solution of 7 (200 mg, crude) in DCM (2 ml) was added TFA (2 ml) and the resulting mixture as stirred at rt for 2 hours. The mixture was concentrated to yield compound 8 as a brown oil (200 mg, 20%).

Step 8: To a solution of compound 8 (100 mg, crude) in DCM (5 ml) was added DIPEA (88.8 mg, 0.688 mmol) and (44.6 mg, 0.275 mmol). The reaction was stirred at 0° C. for 1 hour. The mixture was concentrated and purified by Pre-HPLC to yield Compound 002 as a white solid (34 mg, 35%). ¹H NMR (400 MHz, DMSO) δ 9.75 (s, 1H), 9.64 (s, 1H), 8.84 (s, 2H), 7.58 (s, 1H), 7.47 (d, J=1.9 Hz, 1H), 7.39 (d, J=4.9 Hz, 1H), 7.35 (dd, J=8.3, 2.1 Hz, 1H), 7.28 (d, J=3.3 Hz, 1H), 7.09-7.04 (m, 1H), 6.88 (d, J=8.4 Hz, 1H), 3.64 (d, J=10.5 Hz, 2H), 3.50 (d, J=11.9 Hz, 2H), 3.37 (d, J=8.4 Hz, 2H), 2.98 (dd, J=30.8, 11.3 Hz, 6H), 2.81 (s, 3H), 2.61-2.55 (m, 1H), 2.38 (d, J=11.7 Hz, 2H), 1.51 (t, J=11.1 Hz, 2H), 0.86 (d, J=6.9 Hz, 6H). LCMS: m/z=563 (M+H).

Example 3

Synthesis of Compound 003

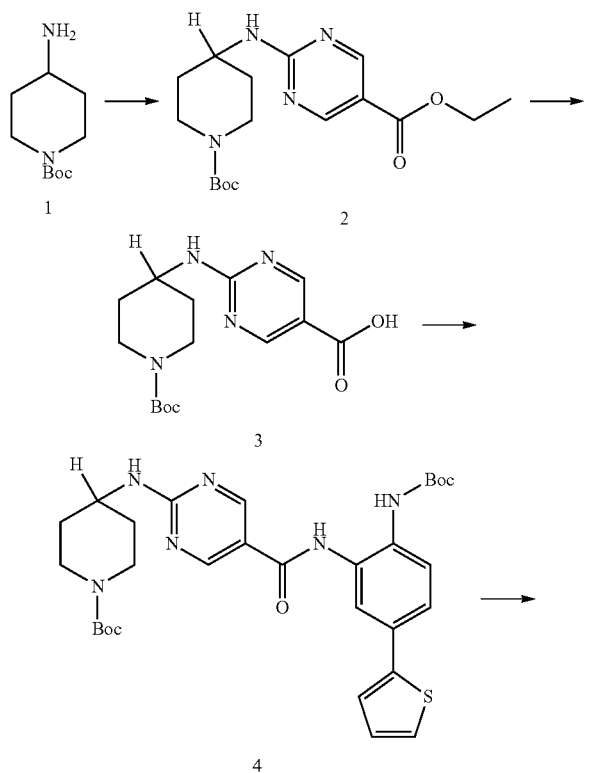

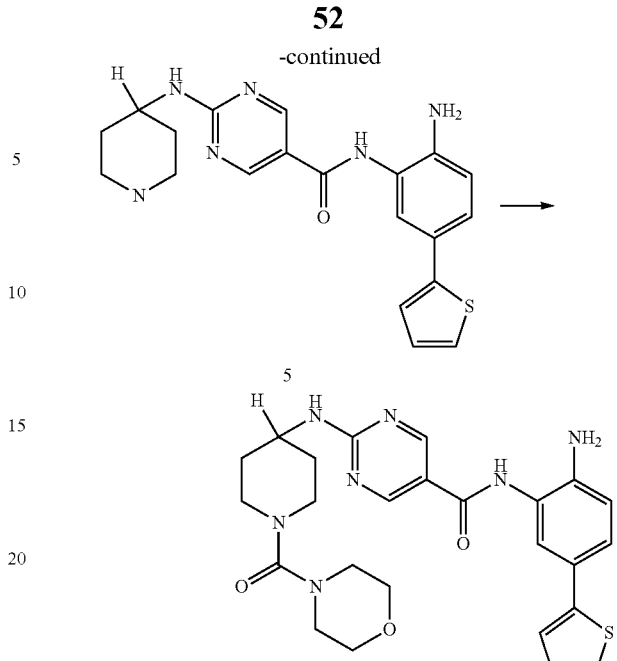

Step 1: A mixture of 2-Cl-pyrimidine (1.86 g, 10 mmol), an amine (3.00, 15 mmol), and NEt3 (3.0 g, 30 mmol) in 1,4-dioxane (20 ml) was stirred at 95° C. overnight. The mixture was concentrated, EA (60 ml) and aqueous citric acid (60 mL) were added, and the resulting mixture was stirred for 30 min. The organic layer was separated, dried, and concentrated to yield compound 2 (3.4 g, yield: 97%) as a light yellow solid.

Step 2: A mixture of compound 2 (3.5 g, 10 mmol) and NaOH (2M, 15 ml) in EtOH (15 ml) and THF (15 ml) was stirred at 60° C. for 2 hours. The mixture was concentrated, and aqueous citric acid was added until the pH<7. The resulting mixture was stirred for 30 min and filtered to yield compound 3 (2.8 g, yield: 90%) as a light yellow solid.

Step 3: A mixture of compound 3 (3.2 g, 10 mmol), compound amine (2.9 g, 10 mmol), HOAT (2.0 g, 15 mmol), EDCI (3.8 g, 20 mmol) in DMF (25 ml) was stirred at 60° C. overnight. EA (100 ml) and aqueous saturated NaCl (100 ml) were added to the mixture and the resulting mixture was stirred for 30 min. The organic layer was separated, washed by aqueous saturated NaCl (50 ml×2), dried and concentrated to produce a residue, which was washed by CH₃CN (10~20 ml) to yield compound 4 (2.9 g, 50%) as a gray solid.

Step 4: To a solution of compound 4 (2.9 g, 5 mmol) in DCM (30 ml) was added TFA (5 ml) at rt for 2 hours. The mixture was concentrated to yield compound 5 (2.9 g, 100%) without further purification.

Step 5: To a solution of compound 4 (197 mg, 0.5 mmol) and NEt3 (250 mg, 2.5 mmol) in DCM (5 ml) was added morpholine-4-carbonyl chloride (194 mg, 0.65 mmol) at 0° C. LCMS was used to monitor the reaction to completion. NH₃—H₂O (0.5 ml) was added to the reaction mixture which was then stirred for 30 min and concentrated to a residue. Purification by silica gel column yielded Compound 003 (114 mg, 45%) as a light yellow solid. ¹H NMR (500 MHz, DMSO) δ 9.54 (s, 1H), 8.85 (s, 2H), 7.88 (d, J=7.9 Hz, 1H), 7.44 (d, J=1.9 Hz, 1H), 7.35 (d, J=5.0 Hz, 1H), 7.29 (dd, J=8.3, 2.1 Hz, 1H), 7.24 (d, J=3.4 Hz, 1H), 7.05 (dd, J=4.9, 3.7 Hz, 1H), 6.79 (d, J=8.3 Hz, 1H), 5.21 (s, 2H), 4.01 (dd, J=7.2, 3.3 Hz, 1H), 3.68-3.51 (m, 7H), 3.18-3.04 (m, 5H), 2.88 (t, J=11.7 Hz, 2H), 1.86 (d, J=10.0 Hz, 2H), 1.45 (dd, J=20.5, 11.3 Hz, 2H). LCMS: m/z=508 (M+H)

Example 4

Synthesis of Compound 004

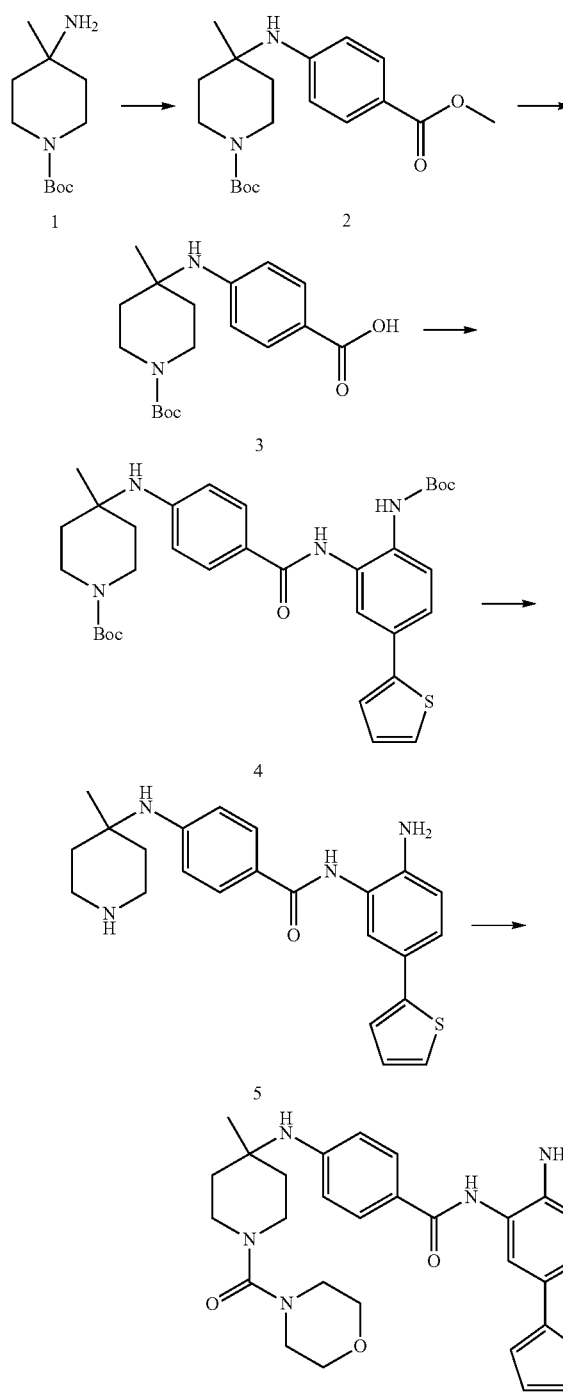

Step 1: A solution of amine 1 (1 g, 4.67 mmol), methyl 4-bromobenzoate (1 g, 4.67 mmol), $Pd_2(dba)_3$ (428 mg, 0.47 mmol), Ruphos (218 mg, 0.47 mmol), $Cs_2CO_3$ (4.5 g, 14.0 mmol) in Tol (50 ml) was flushed with $N_2$ and stirred at 98° C. overnight. The mixture was filtered, concentrated, and purified by silica gel chromatography (PE:EA=5:1-1:1) to yield compound 2 as a yellow solid (1.1 g, 65%)

Step 2: To a mixture of compound 2 (1.1 g) in EtOH (aqueous 95%, 5 ml) was added NaOH (2M, 5 ml) and the resulting solution was stirred at 55° C. for 2 hours. Water (50 ml) was added to the mixture and the pH was adjusted to 7 with citric acid. The resulting mixture was extracted with EA (50 ml×3). The EA phase was dried with anhydrous $Na_2SO_4$ and concentrated to yield compound 3 as a white solid (1 g, crude).

Step 3: A solution of compound 3 (800 mg, crude), amine (694 mg, 2.395 mmol), EDCI (618 mg, 4.790 mmol), HOAT (651 mg, 4.790 mmol), DMAP (29 mg, 0.239 mmol), and DIPEA (927 mg, 7.186 mmol) in DMF (20 ml) was stirred at 55° C. for 3 days. EA (100 ml) was added to the mixture and the resulting solution was washed with water (50 ml×3), concentrated, and purified by silica gel chromatography (PE:EA=6:1-1:1) to yield compound 4 as a brown solid (650 mg, 45%).

Step 4: To a solution of compound 4 (300 mg) in DCM (2 ml) was added TFA (2 ml) and the resulting solution was stirred at rt for 2 hours. The mixture was concentrated to yield compound 5 as a brown oil (400 mg, crude).

Step 5: To a solution of compound 5 (200 mg, crude) in DCM (20 ml) was added DIPEA (190 mg, 1.478 mmol) and morpholine-4-carbonyl chloride (110 mg, 0.739 mmol). The resulting reaction mixture was stirred at 0° C. for 1 hour. The mixture was concentrated and purified by Pre-HPLC to yield Compound 004 as a white solid (67.4 mg). $^1$H NMR (500 MHz, DMSO) δ 9.85 (s, 1H), 7.81 (t, J=21.9 Hz, 2H), 7.58 (d, J=1.7 Hz, 1H), 7.53-7.42 (m, 2H), 7.40 (d, J=3.1 Hz, 1H), 7.11 (dd, J=5.0, 3.6 Hz, 2H), 6.92 (s, 2H), 3.63-3.47 (m, 4H), 3.31-3.01 (m, 8H), 1.98 (d, J=14.0 Hz, 2H), 1.63 (d, J=12.9 Hz, 2H), 1.37 (s, 3H). LCMS: m/z=520 (M+H).

Example 5

Synthesis of Compound 005

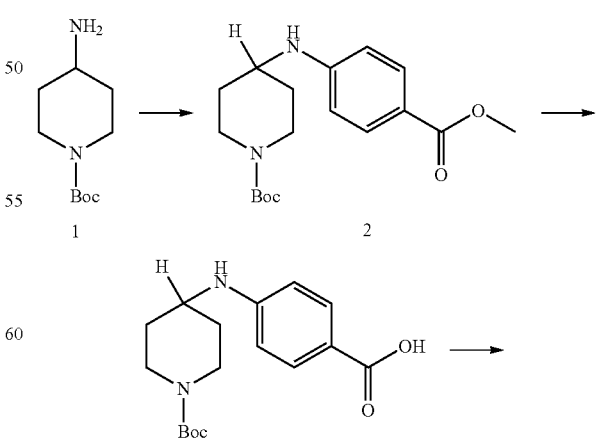

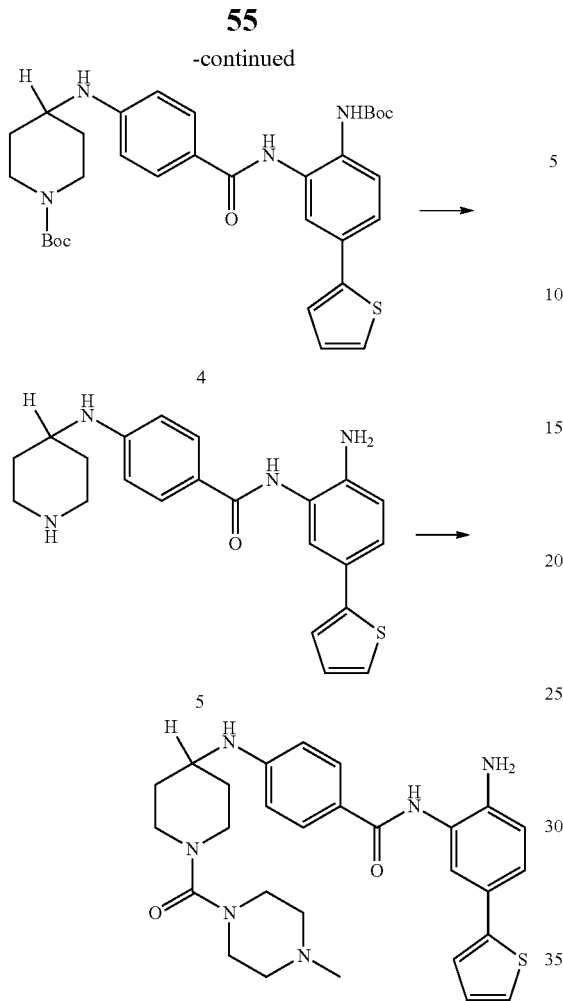

Step 1: To a solution of compound 1 (1 g, 5 mmol) and methyl 4-bromobenzoate (1.1 g, 5 mmol) in toluene (20 ml) was added Pd2(dba)3 (230 mg, 0.25 mmol), Ruphos (290 mg, 0.5 mmol) and Cs2CO3 (4.9 g, 15 mmol). The reaction was stirred at 95° C. overnight under a N₂ atmosphere. After the starting material was fully consumed, the heterogeneous mixture was filtered through diatomite and concentrated in vacuo to yield a viscous oil, which was purified by silica gel column to yield compound 2 (1 g, 60%).

Step 2: Compound 2 (1 g, 3 mmol) was dissolved with MeOH (10 ml) and THF (10 ml). 2N NaOH (15 ml) was then added into the solution. The reaction was stirred at 55° C. for 1 hour. The reaction mixture was concentrated to remove the solvent and the pH was adjusted to between about 4~5 and extracted with EA. The organic phase was washed with brine and dried over Na₂SO₄. Concentration of the organic phase yielded compound 3 (800 mg, 82%) as a white solid.

Step 3: To a solution of compound 3 (500 mg, 1.56 mmol) and amine (453 mg, 1.56 mmol) in DMF (10 ml) was added HOAT (421 mg, 3.1 mmol), EDCI (592 mg, 3.1 mmol) and DIPEA (400 mg, 3.1 mmol). The reaction was stirred at 55° C. overnight. The reaction was quenched with water and extracted with EA. The organic phase was washed with brine and dried over Na₂SO₄. Purification by silica gel column yielded compound 4 (800 mg, 80%) as a light yellow solid.

Step 4: To a solution of the compound 4 (800 mg, 1.35 mmol) in DCM (10 ml) was added TFA (5 ml). The solution was stirred at rt for 30 min. Concentration of the solution yielded compound 5 (600 mg, 100%) as a gray solid.

Step 5: To a solution of compound 5 (80 mg, 0.20 mmol) and 4-methylpiperazine-1-carbonyl chloride hydrochloride (40 mg, 0.20 mmol) was added triethylamine (100 mg, 1 mmol) at 0° C. The reaction was stirred at 0° C. for 2 h and then filtered through silica gel. Concentration and purification by Pre-HPLC yielded Compound 004 (15 mg, 15%) as a white solid. ¹H NMR (400 MHz, DMSO) δ 9.37 (s, 1H), 7.78 (d, J=8.7 Hz, 2H), 7.45 (d, J=2.1 Hz, 1H), 7.36 (dd, J=5.1, 1.0 Hz, 1H), 7.28 (d, J=2.1 Hz, 1H), 7.26 (d, J=2.2 Hz, 1H), 7.24 (dd, J=3.5, 1.1 Hz, 1H), 7.05 (dd, J=5.1, 3.6 Hz, 1H), 6.80 (d, J=8.3 Hz, 1H), 6.65 (d, J=8.8 Hz, 2H), 6.20 (d, J=8.1 Hz, 1H), 5.08 (s, 2H), 3.57 (d, J=13.0 Hz, 3H), 3.15 (s, 4H), 2.91 (t, J=11.3 Hz, 2H), 2.33 (s, 3H), 2.20 (s, 3H), 1.91 (d, J=10.2 Hz, 2H), 1.41-1.24 (m, 2H). LCMS: m/z=519 (M+H).

Example 6

Synthesis of Compound 006

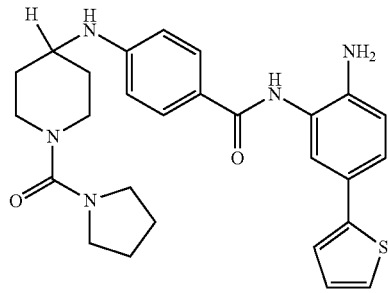 [SMILES: Nc1ccc(-c2cccs2)cc1NC(=O)c1ccc(NC2CCN(C(=O)N3CCCC3)CC2)cc1]

Steps 1-4: Refer to steps 1-4 of Example 5 to obtain compound 5.

Step 5: To a solution of compound 5 (100 mg, 0.25 mmol) and pyrrolidine-1-carbonyl chloride (34 mg, 0.25 mmol) was added triethylamine (100 mg, 1 mmol) at 0° C. The reaction was stirred at 0° C. for 2 h and then filtered through silica gel. Concentration and purification by Pre-HPLC yielded Compound 006 (10 mg, 8%) as a white solid. ¹H NMR (400 MHz, DMSO) δ 9.50 (s, 1H), 7.79 (d, J=8.8 Hz, 2H), 7.50 (d, J=2.1 Hz, 1H), 7.40 (d, J=4.2 Hz, 1H), 7.33 (dd, J=8.3, 2.1 Hz, 1H), 7.29 (d, J=2.7 Hz, 1H), 7.07 (dd, J=5.1, 3.6 Hz, 1H), 6.91 (d, J=8.3 Hz, 1H), 6.66 (d, J=8.8 Hz, 2H), 3.63 (d, J=13.2 Hz, 2H), 3.53 (s, 1H), 3.26 (t, J=6.5 Hz, 4H), 2.87 (t, J=11.2 Hz, 2H), 1.91 (d, J=10.8 Hz, 2H), 1.75 (t, J=6.5 Hz, 5H), 1.34 (dd, J=20.6, 10.1 Hz, 2H). LCMS: m/z=490 (M+H).

Example 7

Synthesis of Compound 007

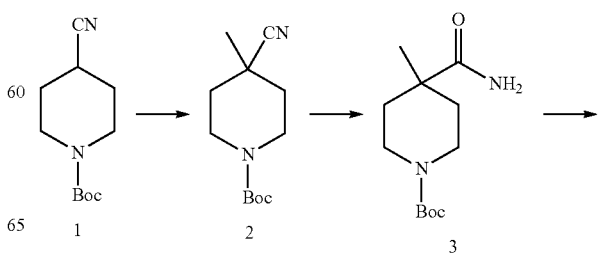

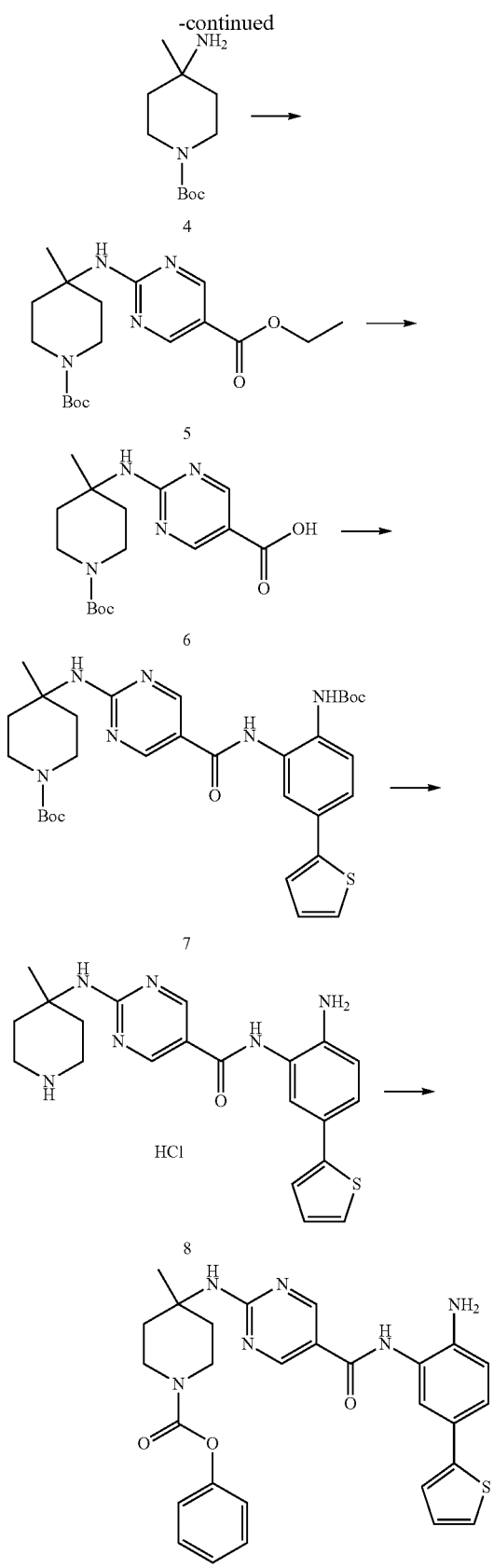

into a round-bottomed flask with compound 1 (25 g, 120 mmol) at −76° C. under nitrogen atmosphere. The mixture was stirred for 4 h at −76° C. Then iodomethane (15 ml, 240 mmol) was added into the system. The reaction mixture was stirred at −76° C. for 30 min, and then warmed to room temperature and stirred overnight. The reaction mixture was quenched with 150 ml saturated aqueous NH4Cl, diluted with water and extracted with EtOAc. The organic layers were washed with water and brine then dried over sodium sulfate, filtered and concentrated to afford target compound 2 (25 g, 93%) as a light yellow solid.

Step 2: Added K2CO3 (31 g, 224 mmol) into the solution of the compound 2 (25 g, 111 mmol) in DMSO (120 ml). H2O2 (100 ml) was added into the system at 60° C. slowly and the reaction was stirred overnight at 60° C. After completed, the system was quenched with cold water and extracted with EA. The organic layers were washed with water and brine then dried over sodium sulfate, filtered and concentrated to get target compound 3 (26 g, 96%) as a white solid.

Step 3: To a solution of compound 3 (26 g, 107 mmol) in 200 ml CH3CN was added 5N KOH (100 ml). Then 1,3-dibromo-5,5-dimethylimidazolidine-2,4-dione (15 g, 54 mmol) was added into the system. The reaction was stirred overnight. After completion, the mixture was concentrated to remove the CH3CN, and the pH of the water phase was adjusted to 5 with 2N HCl in an ice bath, extracted with EA and separated. Then the pH of water phase was adjusted to 10. The precipitate was collected to afford compound 4 (16.1 g, 69%) as a white solid.

Step 4: To a solution of compound 4 (2 g, 9.34 mmol) in 1,4-dioxane (25 ml) was added ethyl 2-chloropyrimidine-5-carboxylate (2.6 g, 14.02 mmol) and DIPEA (5.3 g, 28.03 mmol). The reaction was stirred at 95° C. overnight. Concentration and purification by silica gel column with EA/PE=1/5 afforded compound 5 (1.8 g, 53%) as a light yellow solid.

Step 5: A solution of the compound 5 (465 mg, 1.28 mmol) and 2N NaOH (10 nil, 20 mmol) in THF (10 ml) and EtOH (10 ml) was stirred at 55° C. for 2 h. Concentration and adjustment of the pH of the water phase to 5-6 was followed by extraction with EA (2*15 ml). The organic layers were washed with water and brine then dried over sodium sulfate, filtered and concentrated to afford the compound 6 (400 mg, 93%) as a white solid.

Step 6: A solution of the compound 6 (400 mg, 1.19 mmol), tert-butyl 2-amino-4-(thiophen-2-yl)phenylcarbamate (345 mg, 1.19 mmol), EDCI (307 mg, 2.38 mmol) and DMAP (290 mg, 2.38 mmol) in DMF (10 ml) was formed. The reaction was stirred at 55° C. overnight. After completion, the mixture with was added into water and extracted with EA (2*15 ml). The organic layers were washed with water and brine then dried over sodium sulfate, filtered and concentrated. Then purification by silica gel column with EA/PE=1/2 yielded compound 7 (400 mg, 55%) as a purple solid.

Step 7: To a solution of the compound 7 (400 mg, 0.65 mmol) in 1,4-dioxane (10 ml) was added HCl/1,4-dioxane (5 ml, 20 mmol) at room temperature overnight. Concentration and washing with PE yielded the compound 8 (350 mg, 100%) as a gray solid.

Step 1: A solution of lithium bis(trimethylsilyl)amide (1.0 M solution in THF, 240 ml, 240 mmol) was added slowly Step 8: To a solution of compound 8 (200 mg, 0.45 mmol) and Et3N (101 mg, 2.2 eq) in THF (10 ml) was added phenyl carbonochloridate (78 mg, 0.5 mmol). The mixture was stirred at room temperature for 2 h. After completion, the mixture was concentrated and purified by Prep-HPLC to afford Compound 007 (66 mg, 28%). $^1$H NMR (500 MHz, DMSO) δ 9.71 (s, 1H), 8.88 (s, 2H), 7.68 (s, 1H), 7.50 (s, 1H), 7.42-7.35 (m, 4H), 7.30 (d, J=2.9 Hz, 1H), 7.22 (t, J=7.3 Hz, 1H), 7.12 (d, J=7.9 Hz, 2H), 7.10-7.06 (m, 1H), 6.91 (d, J=8.2 Hz, 1H), 3.76 (d, J=60.0 Hz, 2H), 3.32 (d, J=79.9 Hz, 2H), 2.40 (s, 2H), 1.65 (s, 2H), 1.48 (s, 3H). LCMS: m/z=529 (M+H)$^+$.

Example 8

Synthesis of Compound 008

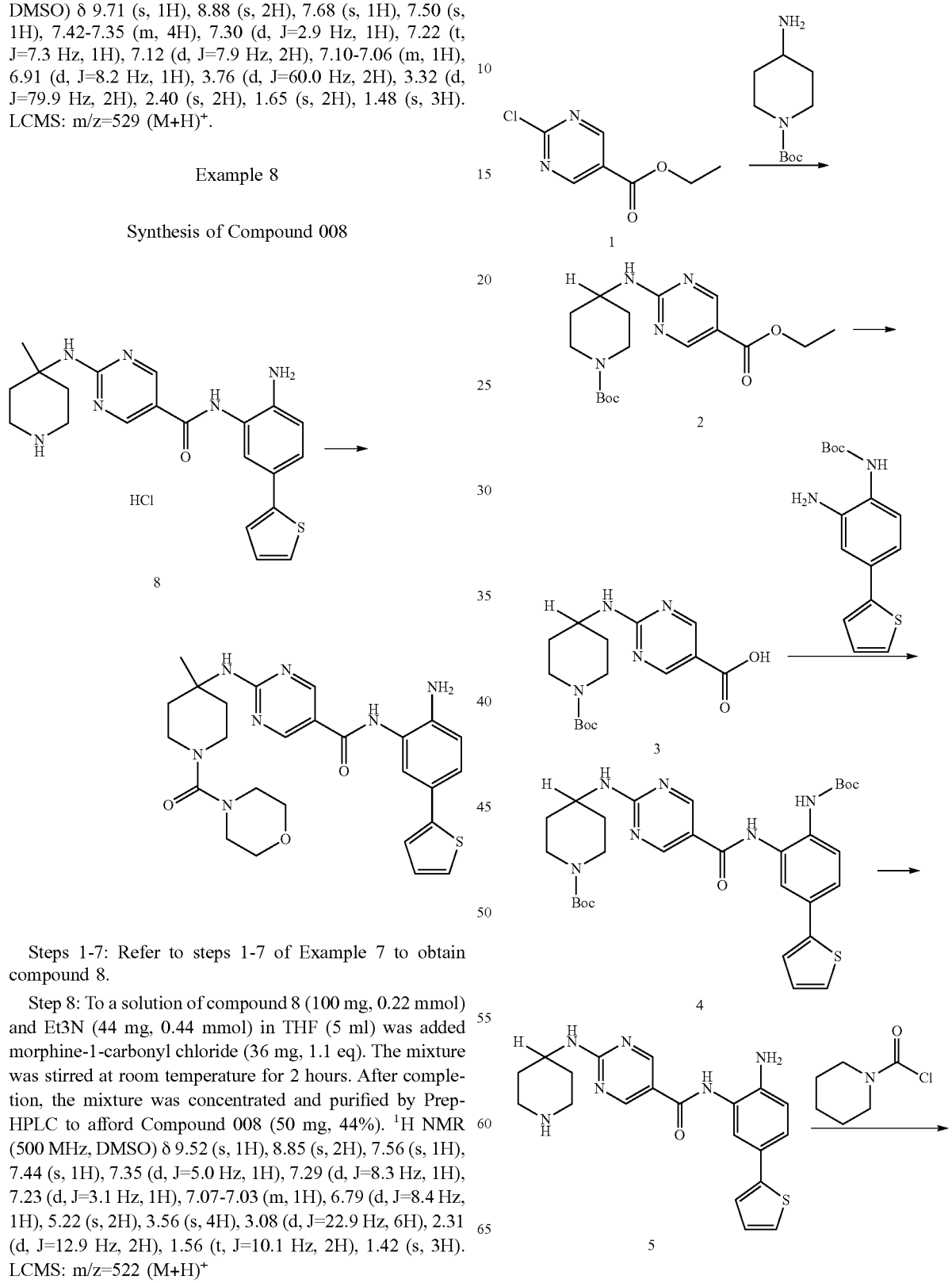

Steps 1-7: Refer to steps 1-7 of Example 7 to obtain compound 8.

Step 8: To a solution of compound 8 (100 mg, 0.22 mmol) and Et3N (44 mg, 0.44 mmol) in THF (5 ml) was added morphine-1-carbonyl chloride (36 mg, 1.1 eq). The mixture was stirred at room temperature for 2 hours. After completion, the mixture was concentrated and purified by Prep-HPLC to afford Compound 008 (50 mg, 44%). $^1$H NMR (500 MHz, DMSO) δ 9.52 (s, 1H), 8.85 (s, 2H), 7.56 (s, 1H), 7.44 (s, 1H), 7.35 (d, J=5.0 Hz, 1H), 7.29 (d, J=8.3 Hz, 1H), 7.23 (d, J=3.1 Hz, 1H), 7.07-7.03 (m, 1H), 6.79 (d, J=8.4 Hz, 1H), 5.22 (s, 2H), 3.56 (s, 4H), 3.08 (d, J=22.9 Hz, 6H), 2.31 (d, J=12.9 Hz, 2H), 1.56 (t, J=10.1 Hz, 2H), 1.42 (s, 3H). LCMS: m/z=522 (M+H)$^+$ Example 9

Synthesis of Compound 009

-continued

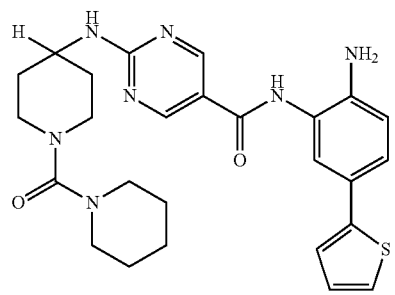

Step 1: A mixture of compound 1 (1.86 g, 10 mmol), compound Boc-amine (3.0 g, 15 mmol), and NEt3 (3.0 g, 30 mmol) in 1,4-dioxane (20 ml) was stirred at 95° C. overnight. The mixture was concentrated, and following the addition of EA (60 ml) and of aqueous citric acid (60 ml), the mixture was stirred for 30 min. The organic layer was separated, dried and concentrated to yield compound 2 (3.4 g, 97%) as a light yellow solid.

Step 2: A mixture of compound 2 (3.5 g, 10 mmol) and NaOH (2M, 15 ml) in EtOH (15 ml) and THF (15 ml) was stirred at 60° C. for 2 h. The mixture was concentrated, and following the addition of aqueous citric acid to adjust to pH<7, the mixture was stirred for 30 min, and filtered to afford compound 3 (2.8 g, 90%) as a light yellow solid.

Step 3: A mixture of compound 3 (3.2 g, 10 mmol), compound Boc-amine (2.9 g, 10 mmol), HOAT (2.0 g, 15 mmol), and EDCI (3.8 g, 20 mmol) in DMF (25 ml) was stirred at 60° C. overnight. To the mixture was added EA (100 ml) and aqueous saturated NaCl (100 ml), and the mixture was stirred for 30 min. The organic layer was separated, washed by aqueous saturated NaCl (50 ml*2), dried and concentrated to yield a residue, which was washed by CH3CN (10-20 ml) to afford compound 4 (2.9 g, 50%) as a gray solid.

Step 3: To a solution of compound 4 (2.9 g, 5 mmol) in DCM (30 ml) was added TFA (5 ml). The mixture was stirred at room temperature for 2 h. The mixture was concentrated to afford compound 5 (2.9 g, 100%) without any further purification.

Step 4: To a solution of compound 5 (197 mg, 0.5 mmol) and NEt3 (250 mg, 2.5 mmol) in DCM (5 ml) was added piperidine-1-carbonyl chloride (96 mg, 0.65 mmol) at 0° C. LCMS was monitored until reaction completion. To the mixture was added NH3H2O (0.5 ml), the mixture was stirred for 30 min and was concentrated to get a residue, which was purified by silica gel column to afford Compound 009 (114 mg, 45%) as light yellow solid. $^1$H NMR (500 MHz, DMSO) δ 9.69 (s, 1H), 8.86 (s, 2H), 7.89 (d, J=8.0 Hz, 1H), 7.49 (s, 1H), 7.40 (d, J=5.1 Hz, 1H), 7.36 (d, J=8.2 Hz, 1H), 7.30 (d, J=3.3 Hz, 1H), 7.07 (dd, J=5.0, 3.7 Hz, 1H), 6.90 (d, J=8.2 Hz, 1H), 3.99 (s, 1H), 3.56 (d, J=11.5 Hz, 2H), 3.10 (s, 4H), 2.84 (t, J=11.6 Hz, 2H), 1.85 (d, J=10.7 Hz, 2H), 1.52 (s, 2H), 1.46 (d, J=8.3 Hz, 6H). LCMS: m/z=506 (M+H)$^+$.

Example 10

Synthesis of Compound 010

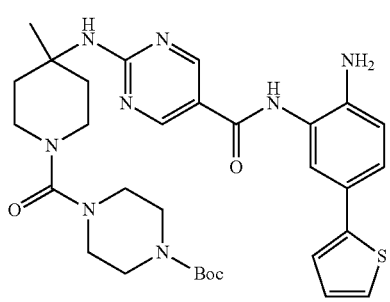

Steps 1-7: Refer to steps 1-7 of Example 7 to obtain compound 8.

Step 8: To a solution of compound 8 (100 mg, 0.22 mmol) and Et3N (44 mg, 0.45 mmol) in THF (5 ml) was added piperazine-1-carbonyl chloride (60 mg, 0.24 mmol). The mixture was stirred at room temperature for 2 hours. After completion, the mixture was concentrated to afford the crude compound 9 as an oil (110 mg, crude).

Step 9: To a solution of the compound 9 (100 mg) in DCM (5 ml) was added TFA (1 ml) at room temperature for 40 mins. After completion, the mixture was concentrated and purification on prep-HPLC to afford Compound 010 (35 mg, 30%, 2 steps) as a yellow solid. $^1$H NMR (500 MHz, DMSO) δ 9.70 (s, 1H), 8.86 (s, 2H), 8.79 (s, 2H), 7.63 (s, 1H), 7.49 (d, J=1.8 Hz, 1H), 7.40 (d, J=5.0 Hz, 1H), 7.36 (dd, J=8.3, 1.9 Hz, 1H), 7.29 (d, J=3.2 Hz, 1H), 7.10-7.04 (m, 1H), 6.90 (d, J=8.3 Hz, 1H), 3.37 (s, 1H), 3.29 (s, 4H), 3.09 (s, 6H), 2.32 (d, J=13.6 Hz, 2H), 1.56 (t, J=10.2 Hz, 2H), 1.43 (s, 3H). LCMS: m/z=521 (M+H)$^+$.

Example 11

Synthesis of Compound 011

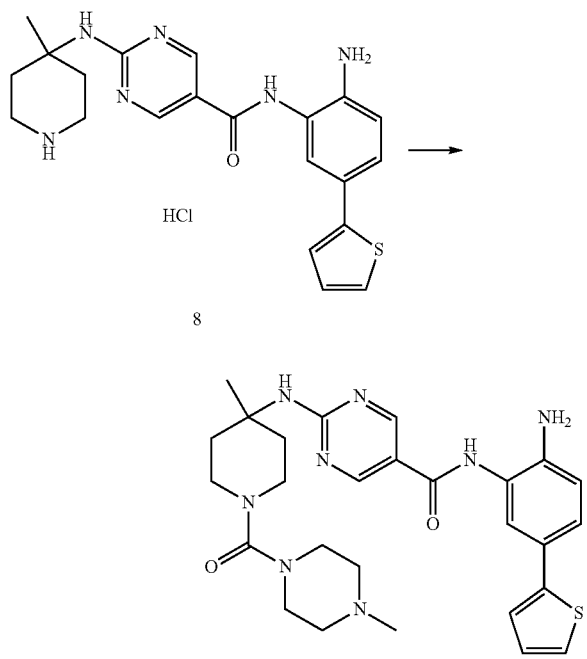 [SMILES: CC1(Nc2ncc(C(=O)Nc3cc(-c4cccs4)ccc3N)cn2)CCNCC1 ; Cl ; CN1CCN(C(=O)N2CCC(C)(Nc3ncc(C(=O)Nc4cc(-c5cccs5)ccc4N)cn3)CC2)CC1]

Steps 1-7: Refer to steps 1-7 of Example 7 to obtain compound 8.

Step 8: To a solution of compound 8 (100 mg, 0.22 mmol) and Et3N (45 mg, 0.45 mmol) in THF (5 ml) was added 4-methylpiperazine-1-carbonyl chloride (40 mg, 0.24 mmol). The mixture was stirred at room temperature for 2 h. The mixture was filtered through silica gel and washed with EA. Concentration and purification by Prep-HPLC yielded Compound 011 (42 mg, 36%). $^1$H NMR (500 MHz, DMSO) δ 9.88 (s, 1H), 9.72 (s, 1H), 8.86 (s, 2H), 7.64 (s, 1H), 7.49 (d, J=1.8 Hz, 1H), 7.41 (d, J=5.0 Hz, 1H), 7.37 (dd, J=8.3, 2.0 Hz, 1H), 7.30 (d, J=2.9 Hz, 1H), 7.08 (dd, J=4.9, 3.7 Hz, 1H), 6.92 (d, J=8.4 Hz, 1H), 3.63 (d, J=11.2 Hz, 2H), 3.38 (d, J=8.2 Hz, 3H), 3.15-2.97 (m, 6H), 2.81 (s, 3H), 2.33 (d, J=13.5 Hz, 2H), 1.57 (t, J=10.1 Hz, 2H), 1.43 (s, 3H). LCMS: m/z=535 (M+H)$^+$.

Example 12

Synthesis of Compound 012

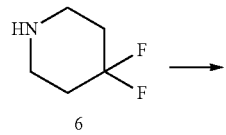

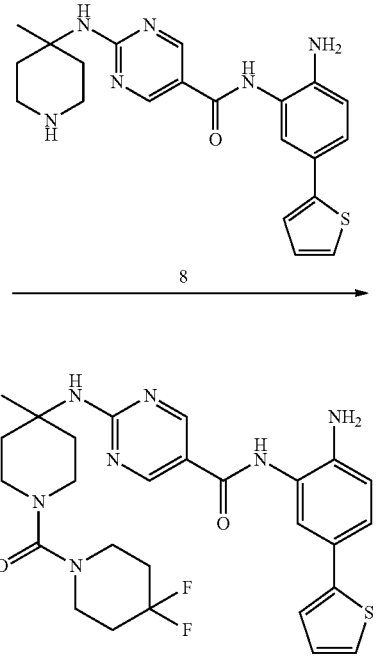

Step 1: To a solution of compound 6 (95 mg, 0.79 mmol) and Et3N (159 mg, 1.6 mmol) in THF (5 ml) was added bis(trichloromethyl)carbonate (119 mg, 0.4 mmol). The mixture was stirred at room temperature for 2 hours and was used directly in the next step (step 2).

Step 2: Refer to steps 1-7 of Example 7 to obtain compound 8. A solution of compound 8 (162 mg, 0.4 mmol) and Et3N (80 mg, 0.8 mmol) in THF (5 ml) was added to a solution of the reaction mixture of step 1 containing compound 7. The reaction was stirred at room temperature for 2 hours. Then the mixture was concentrated and purified by Pre-HPLC to yield Compound 012 (35 mg, 16%). $^1$H NMR (500 MHz, DMSO) δ 9.73 (s, 1H), 8.86 (s, 2H), 7.62 (s, 1H), 7.50 (s, 1H), 7.42 (d, J=5.0 Hz, 1H), 7.38 (d, J=8.4 Hz, 1H), 7.31 (d, J=3.1 Hz, 1H), 7.08 (dd, J=5.0, 3.7 Hz, 1H), 6.93 (d, J=8.1 Hz, 1H), 3.34 (s, 1H), 3.31 (s, 1H), 3.23 (d, J=5.6 Hz, 4H), 3.08 (t, J=10.8 Hz, 2H), 2.31 (d, J=13.7 Hz, 2H), 1.94 (d, J=13.9 Hz, 4H), 1.57 (t, J=10.0 Hz, 2H), 1.43 (s, 3H). LCMS: m/z=556 (M+H)$^+$.

Example 13

Synthesis of Compound 013

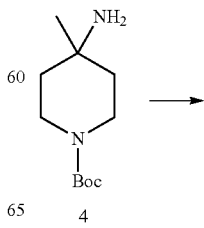

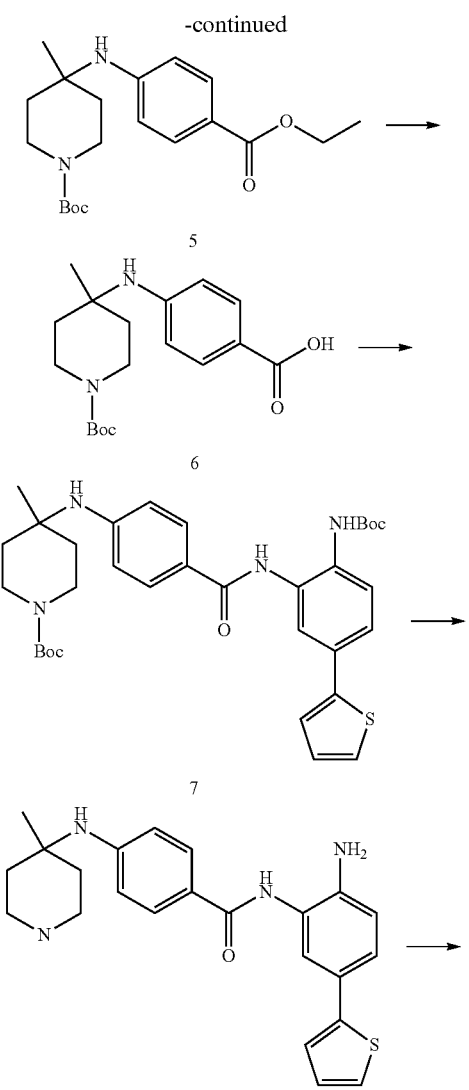

2 h. The mixture was concentrated to yield a residue, and water (100 ml) was added and then aqueous citric acid was added to adjust to pH<7 at 0° C., then filtration afforded compound 6 (369 mg, 80%) as a white solid.

Step 3: A mixture of compound 6 (150 mg, 0.45 mmol), compound Boc-amine (130 mg, 0.45 mmol), HOAT (103 mg, 0.76 mmol), EDCI (145 mg, 0.76 mmol) and NEt3 (154 mg, 1.52 mmol) in DMF (5 ml) was stirred at 60° C. overnight. To the mixture was added EA (100 ml) and aqueous saturated NaCl (100 ml), and the mixture was stirred for 30 min. The organic layer was separated, washed with aqueous saturated NaCl (50 ml*2), dried and concentrated to get a residue, which was purified by Prep-TLC to afford compound 7 (123 mg, 45%) as a yellow solid.

Step 4: To a solution of compound 7 (120 mg, 0.20 mmol) in DCM (5 ml) was added TFA (3 ml) at room temperature for 2 h. The mixture was concentrated to afford compound 8 (80 mg, 100%), which was used in the next step without further purification.

Step 5: To a solution of the compound 8 (80 mg, 0.20 mmol) and Et3N (106 mg, 1.05 mmol) in THF (5 ml) was added compound pyrrolidine-1-carbonyl chloride (74 mg, 0.30 mmol) at 0° C. and stirred for 2 h. To the mixture was added EA (50 ml) and aqueous saturated NaCl (50 ml), and the mixture was stirred for 30 min. The organic layer was separated, washed by aqueous saturated NaCl (50 ml*2), dried and concentrated to afford a residue which was purified by Prep-TLC to get Compound 013 (99 mg, 80%) as a yellow solid. $^1$H NMR (500 MHz, DMSO) δ 9.35 (s, 1H), 7.75 (d, J=8.7 Hz, 2H), 7.45 (d, J=2.0 Hz, 1H), 7.36 (d, J=5.1 Hz, 1H), 7.27 (dd, J=8.3, 2.1 Hz, 1H), 7.24 (d, J=3.5 Hz, 1H), 7.05 (dd, J=5.0, 3.6 Hz, 1H), 6.79 (dd, J=8.5, 3.5 Hz, 3H), 5.89 (s, 1H), 5.07 (d, J=12.4 Hz, 2H), 3.31 (d, J=7.8 Hz, 1H), 3.25 (t, J=6.4 Hz, 5H), 3.10 (t, J=10.5 Hz, 2H), 1.97 (d, J=13.9 Hz, 2H), 1.74 (s, 4H), 1.59 (t, J=9.9 Hz, 2H), 1.37 (s, 3H). LCMS: m/z=504 (M+H)$^+$.

Example 14

Synthesis of Compound 014

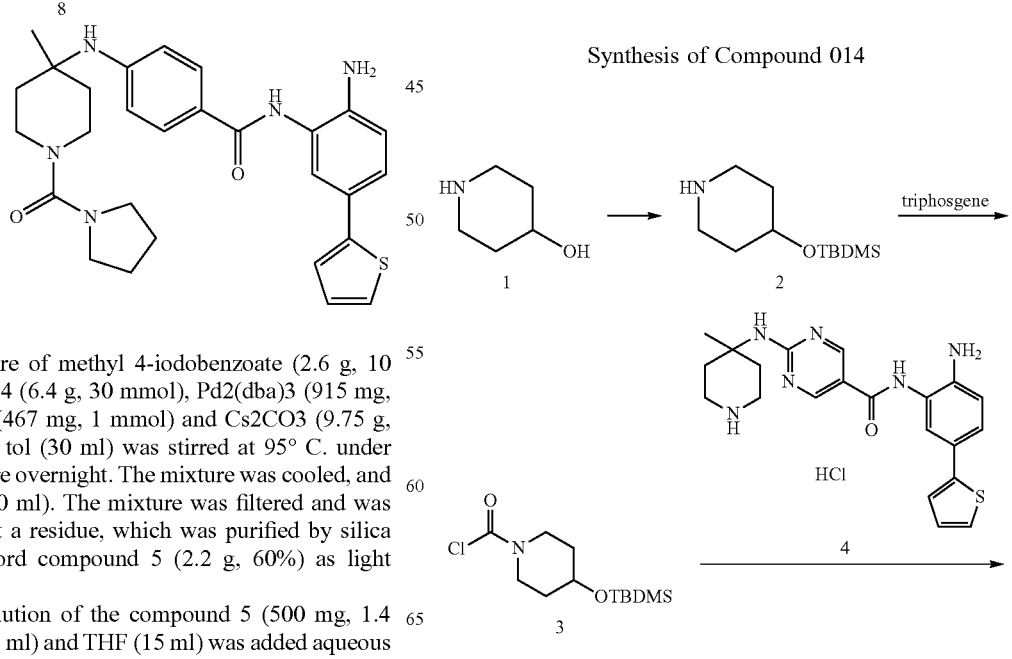

Step 1: A mixture of methyl 4-iodobenzoate (2.6 g, 10 mmol), compound 4 (6.4 g, 30 mmol), Pd2(dba)3 (915 mg, 1 mmol), Ruphos (467 mg, 1 mmol) and Cs2CO3 (9.75 g, 30 mmol, 3 eq) in tol (30 ml) was stirred at 95° C. under nitrogen atmosphere overnight. The mixture was cooled, and EA was added (100 ml). The mixture was filtered and was concentrated to get a residue, which was purified by silica gel column to afford compound 5 (2.2 g, 60%) as light yellow solid.

Step 2: To a solution of the compound 5 (500 mg, 1.4 mmol) in EtOH (15 ml) and THF (15 ml) was added aqueous NaOH (2M, 15 ml), and the mixture was stirred at 60° C. for -continued

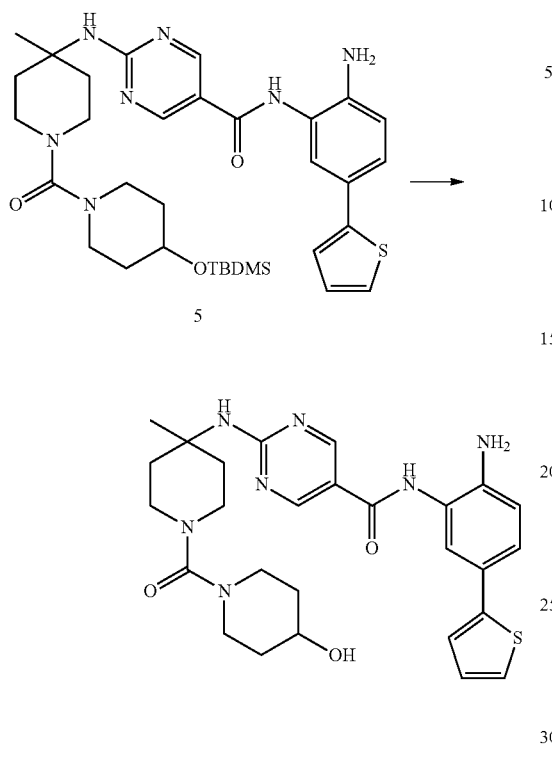

Step 1: A solution of the 4-hydroxypiperidine (compound 1, 0.8 g, 7.9 mmol), pyridine (1.3 g, 16 mmol) and tert-Butyldimethylsilyl chloride (1.4 g, 9.5 mmol) in CH2Cl2 (25 ml) was formed at 0° C. The mixture was stirred for 3 h. After completion, the mixture was concentrated and was purified by silica gel column with EA:PE=1:5 to afford compound 2 (1.5 g, 88%) as a light yellow solid.

Step 2: To a solution of compound 2 (95 mg, 0.44 mmol) and Et3N (89 mg, 0.9 mmol) in THF (5 ml) was added triphosgene (74 mg, 0.25 mmol). The mixture was stirred at room temperature for 2 hours and was used directly in the next step.

Step 3: To a solution of the compound 4 (162 mg, 0.4 mmol) and Et3N (80 mg, 0.8 mmol) in THF (5 ml) was added the above solution from step 2 containing compound 3. The mixture was stirred at room temperature for 2 hours and was used in the next step without any further purification.

Step 4: To the solution of the compound 5 (crude mixture) in THF (5 ml) was added TBAF (5 drops) at 0° C. The mixture was stirred at room temperature for 2 hours, then concentrated and purified by Prep-HPLC to afford Compound 014 (29 mg, 15%, 3 steps). $^1$H NMR (400 MHz, DMSO) δ 9.67 (s, 1H), 8.86 (s, 2H), 7.56 (s, 1H), 7.48 (s, 1H), 7.39 (d, J=4.9 Hz, 1H), 7.37-7.31 (m, 1H), 7.28 (d, J=3.3 Hz, 1H), 7.10-7.03 (m, 1H), 6.88 (d, J=8.3 Hz, 1H), 3.59 (s, 3H), 3.42 (s, 1H), 3.25 (d, J=13.6 Hz, 2H), 3.03 (t, J=11.0 Hz, 2H), 2.83 (t, J=10.6 Hz, 2H), 2.29 (d, J=13.5 Hz, 2H), 1.70 (d, J=9.9 Hz, 2H), 1.57 (t, J=10.3 Hz, 2H), 1.44 (d, J=10.4 Hz, 3H), 1.34-1.27 (m, 2H). LCMS: m/z=536 (M+H)$^+$.

Example 15

Synthesis of Compound 015

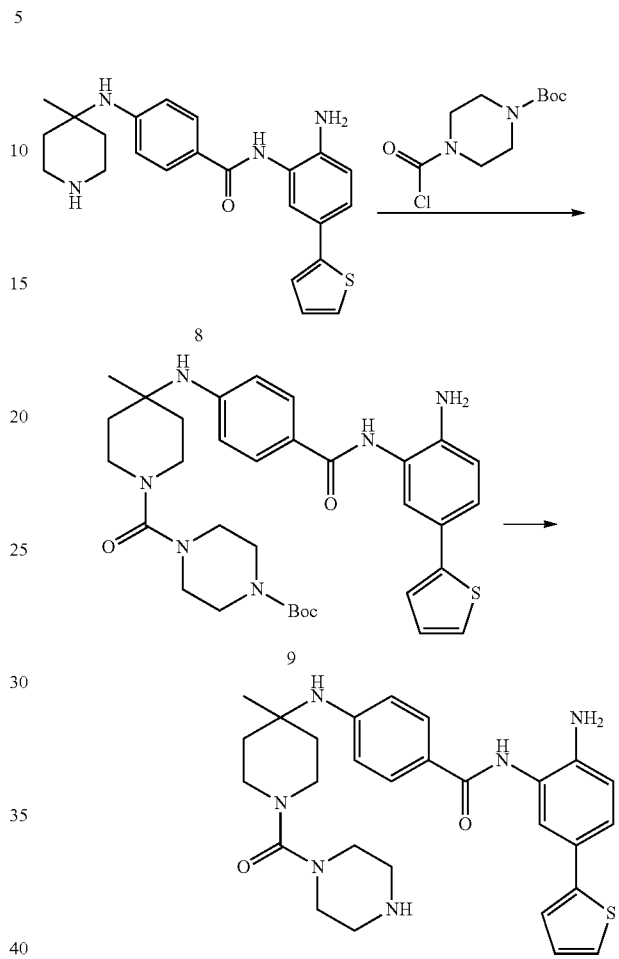

Steps 1-4: Refer to steps 1-4 of Example 13 to obtain compound 8.

Step 5: To a solution of the compound 8 (80 mg, 0.20 mmol) and Et3N (106 mg, 1.05 mmol) in THF (5 ml) was added tert-butyl 4-(chlorocarbonyl)piperazine-1-carboxylate (74 mg, 0.30 mmol) at 0° C., and the mixture was stirred for 2 h. To the mixture was added EA (20 ml) and aqueous saturated NaCl (20 ml), and the mixture was stirred for 30 min. The organic layer was separated, washed by aqueous saturated NaCl (50 ml*2), dried and concentrated to yield a residue, which was purified by Prep-TLC to afford compound 9 (99 mg, 80%) as a yellow solid.

Step 6: To a solution of compound 9 (90 mg, 0.15 mmol) in DCM (5 ml) was added TFA (3 ml) slowly. The mixture was stirred at room temperature for 2 h. Then the mixture was concentrated to get a residue, which was purified by Prep-HPLC to yield Compound 015 (45 mg, 60%) as a white solid. $^1$H NMR (400 MHz, DMSO) δ 9.58 (s, 1H), 8.78 (s, 2H), 7.78 (t, J=9.6 Hz, 2H), 7.52 (d, J=2.1 Hz, 1H), 7.42 (d, J=5.1 Hz, 1H), 7.36 (dd, J=8.3, 2.1 Hz, 1H), 7.31 (d, J=3.5 Hz, 1H), 7.08 (dd, J=5.0, 3.6 Hz, 1H), 6.96 (d, J=8.3 Hz, 1H), 6.84 (d, J=8.4 Hz, 2H), 5.97 (s, 6H), 3.18 (t, J=10.6 Hz, 2H), 3.10 (s, 4H), 2.02-1.93 (m, 2H), 1.60 (t, J=9.7 Hz, 2H), 1.37 (s, 3H). LCMS: m/z=519 (M+H)$^+$.

Example 16

Synthesis of Compound 016

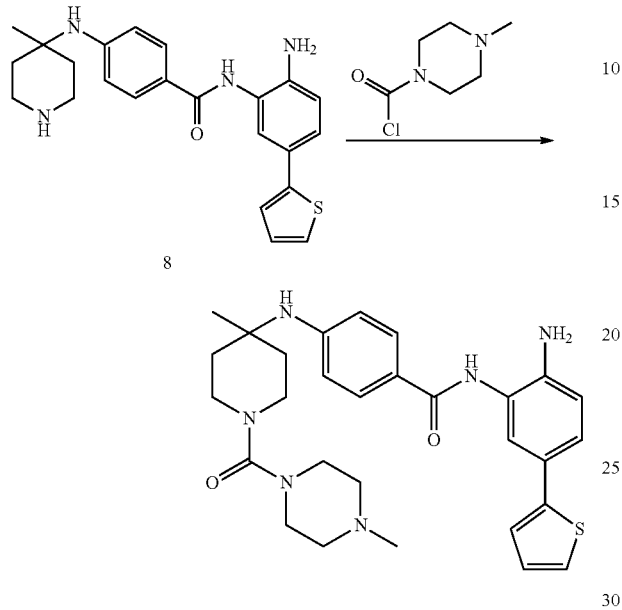

Steps 1-4: Refer to steps 1-4 of Example 13 to obtain compound 8.

Step 5: To a solution of the compound 8 (80 mg, 0.20 mmol) and Et3N (106 mg, 1.05 mmol) in THF (5 ml) was added 4-methylpiperazine-1-carbonyl chloride (49 mg, 0.30 mmol) at 0° C., and the mixture was stirred for 2 h. The mixture was purified by Prep-TLC to afford Compound 016 (49 mg, 46%) as a yellow solid. $^1$H NMR (400 MHz, DMSO) δ 9.79 (s, 1H), 9.58 (s, 1H), 7.79 (d, J=8.7 Hz, 2H), 7.51 (d, J=2.1 Hz, 1H), 7.42 (d, J=4.2 Hz, 1H), 7.36 (dd, J=8.3, 2.1 Hz, 1H), 7.31 (d, J=3.5 Hz, 1H), 7.08 (dd, J=5.0, 3.6 Hz, 1H), 6.95 (d, J=8.3 Hz, 1H), 6.84 (d, J=8.3 Hz, 2H), 3.64 (d, J=11.6 Hz, 2H), 3.43-3.28 (m, 4H), 3.18 (t, J=10.3 Hz, 2H), 3.10-2.96 (m, 4H), 2.81 (s, 3H), 1.99 (d, J=13.4 Hz, 2H), 1.60 (t, J=9.7 Hz, 2H), 1.37 (s, 3H). LCMS: m/z=533 (M+H)$^+$.

Example 17

Synthesis of Compound 017

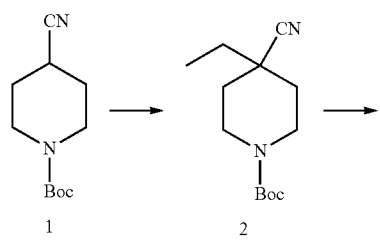

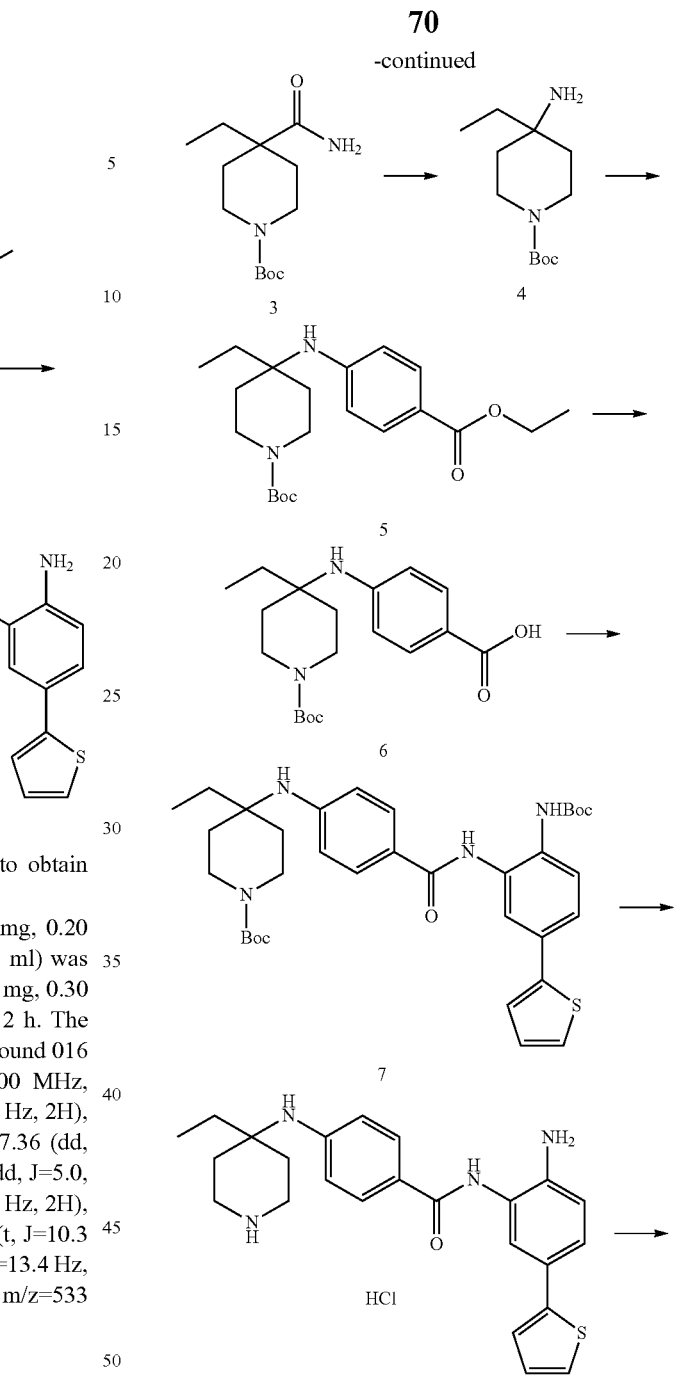

Step 1: To a solution of lithium bis(trimethylsilyl)amide (1.0 M in THF, 240 ml, 240 mmol) in a round-bottomed flask was added compound 1 (25 g, 120 mmol) slowly at −76° C. under nitrogen atmosphere. After the mixture was stirred for 4 hours at −76° C., iodoethane (17 ml, 240 mmol) was added dropwise into the system. The reaction mixture was stirred for further 30 minutes and then warmed to room temperature and stirred overnight. The residue was quenched with 150 ml saturated aqueous NH4Cl, diluted with water and extracted with EtOAc. The organic layers were washed with water and brine then dried over sodium sulfate, filtered and concentrated to afford target compound 2 (20 g, 70%) as a light yellow solid.

Step 2: To a solution of the compound 2 (20 g, 84 mmol) was added K2CO3 (23 g, 168 mmol) in DMSO (120 ml). H2O2 (100 ml) was added into the system at 60° C. very slowly and the reaction was stirred overnight at 60° C. Cold water was added, and the mixture was extracted with EA (3*100 ml). The organic layers were washed with water and brine then dried over sodium sulfate, filtered and concentrated to get target compound 3 (21 g, 99%) as a white solid.

Step 3: To a solution of the compound 3 (20.5 g, 80 mmol) in CH3CN (200 ml) and 5N KOH (100 ml) was added 1,3-dibromo-5,5-dimethylimidazolidine-2,4-dione (11.1 g, 40 mmol). The mixture was stirred overnight at room temperature. After completion, the mixture was concentrated to remove CH3CN. Adjustment of the pH of the water phase to 5 was with 2N HCl in ice bath, the mixture was extracted with EA and separated. Then adjustment of the pH of water phase to 10. The precipitate was collected to afford the compound 4 (10 g, 55%) as a white solid.

Step 4: A solution of the compound 4 (1.0 g, 4.4 mmol), ethyl 4-bromobenzoate (943 mg, 4.4 mmol), Pd2(dba)3 (202 mg, 0.22 mmol), Ruphos (103 mg, 0.22 mmol) and Cs2CO3 (2.9 g, 8.8 mmol) in toluene (25 ml) was stirred at 100° C. overnight. The mixture was concentrated and purified by silica gel column with EA:PE=1:5 to afford compound 5 (1.0 g, 59%) as a light yellow solid.

Step 5: A solution of the compound 5 (233 mg, 0.65 mmol) and 2N NaOH (10 ml, 20 mmol) in THF (10 ml) and EtOH (10 ml) was stirred at 55° C. for 2 hours. Concentration and adjustment of the pH of the water phase to 5-6, was followed by extraction with EA (3*15 ml). The organic layers were washed with water and brine then dried over sodium sulfate, filtered and concentrated to afford compound 6 (200 mg, 93%) as a white solid.

Step 6: A mixture of the compound 6 (200 mg, 0.6 mmol), tert-butyl 2-amino-4-(thiophen-2-yl)phenylcarbamate (173 mg, 0.6 mmol), EDCI (154 mg, 1.2 mmol) and DMAP (145 mg, 1.2 mmol) in DMF (10 ml) was stirred at 55° C. overnight. The mixture was diluted with water and extracted with EA. The organic layers were washed with water and brine then dried over sodium sulfate, filtered and concentrated. Then purification by silica gel column with EA:PE=1:2 yielded compound 7 (200 mg, 55%) as a purple solid.

Step 7: To a solution of compound 7 (200 mg, 0.32 mmol) in 1,4-dioxane (10 ml) was added HCl/1,4-dioxane (5 ml, 20 mmol), and the mixture was stirred at room temperature overnight. Concentration and washing with PE afforded compound 8 (175 mg, 100%) as a gray solid.

Step 8: To the solution compound 8 (95 mg, 0.21 mmol) and Et3N (106 mg, 1.05 mmol) in THF (5 ml) was added morpholine-4-carbonyl chloride (50 mg, 0.3 mmol), and the mixture was stirred at room temperature for 2 hours. The mixture was filtered through silica gel and was washed with EA. Concentration and purification by Prep-HPLC afforded Compound 017 (10 mg, 9%). $^1$H NMR (400 MHz, DMSO) δ 9.56 (s, 1H), 7.76 (d, J=8.7 Hz, 2H), 7.52 (s, 1H), 7.42 (d, J=4.8 Hz, 1H), 7.36 (d, J=8.2 Hz, 1H), 7.31 (d, J=3.0 Hz, 1H), 7.11-7.04 (m, 1H), 6.95 (d, J=8.2 Hz, 1H), 6.81 (d, J=8.5 Hz, 2H), 5.86 (s, 1H), 3.55 (s, 8H), 3.11 (s, 4H), 2.02 (d, J=13.3 Hz, 2H), 1.76 (d, J=6.6 Hz, 2H), 1.50 (t, J=10.9 Hz, 2H), 0.75 (t, J=7.3 Hz, 3H). LCMS: m/z=534 (M+H)$^+$.

Example 18

Synthesis of Compound 018

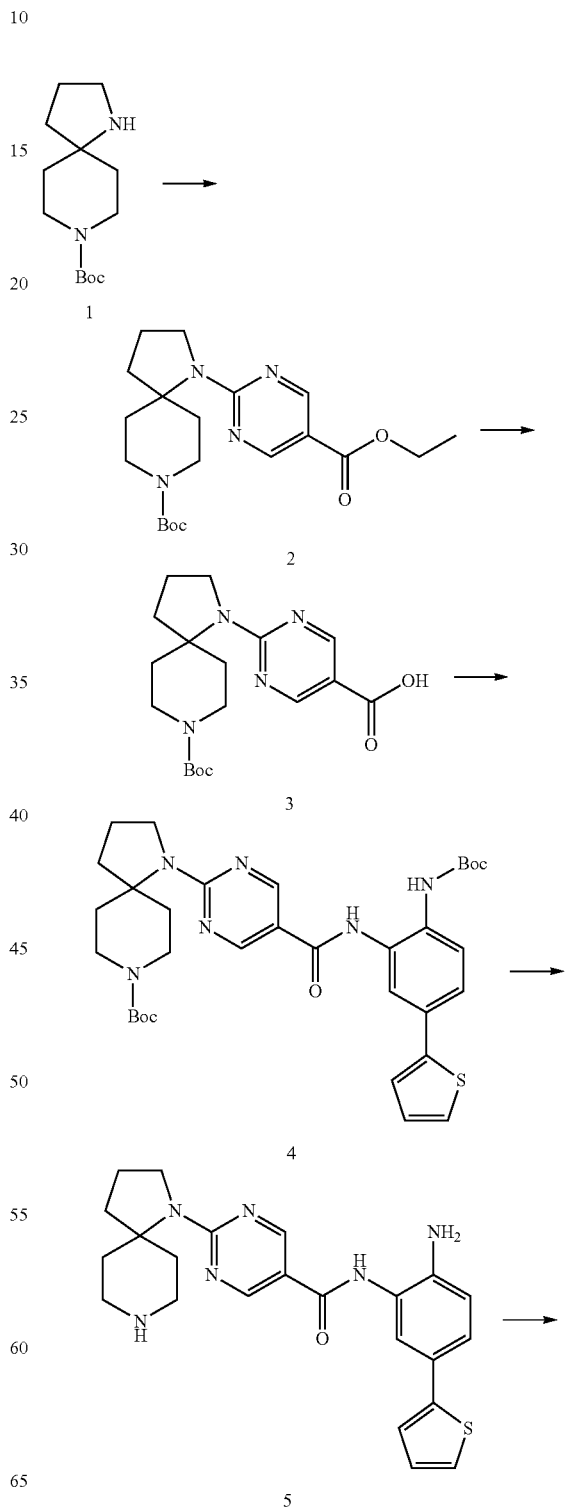

Example 19

Synthesis of Compound 019

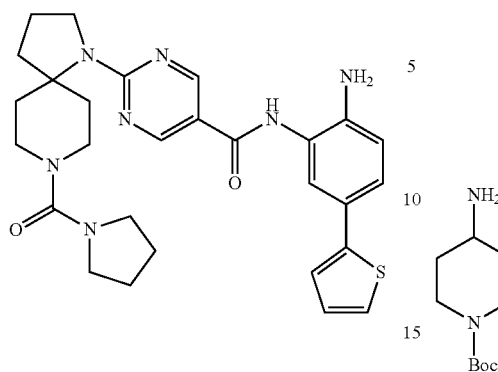

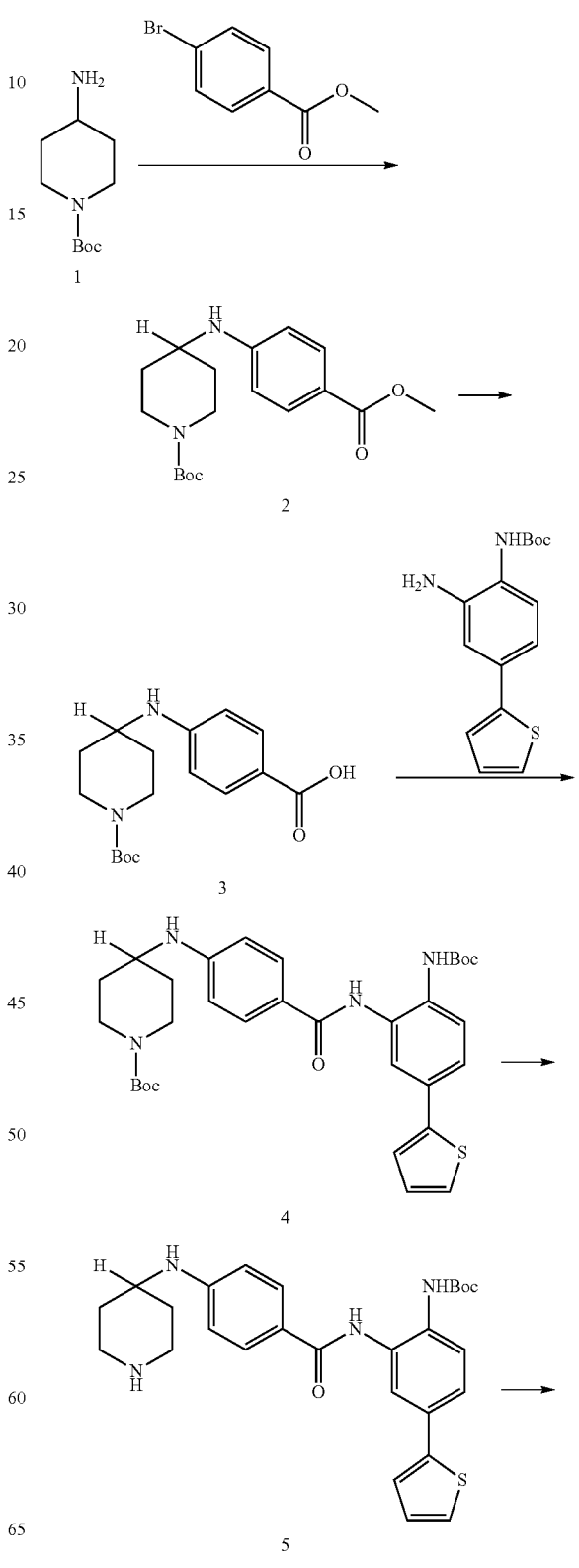

Step 1: To a solution of compound 1 (1.2 g, 5 mmol) in dioxane (20 ml) was added DIPEA (1.3 g, 10 mmol) and ethyl 2-chloropyrimidine-5-carboxylate (5.5 mmol, 1.0 g). The mixture was stirred at 100° C. overnight. After completion, concentration and direct purification by prep-TLC with PE:EA=2:1 afforded compound 2 (1.37 g, 70%) as a white solid.

Step 2: To a solution of compound 2 (220 mg, 0.56 mmol) in EtOH (5 ml) and THF (5 ml) was added aqueous NaOH (2M, 2 ml). The reaction was stirred at 60° C. for 2 h. The mixture was concentrated to get a residue. To the residue was added water (10 ml), and aqueous citric acid was added to adjust to pH<7 at 0° C., and the mixture was filtered to afford compound 3 (200 mg, crude) as a white solid.

Step 3: A mixture of the compound 3 (200 mg, crude), compound tert-butyl 2-amino-4-(thiophen-2-yl)phenylcarbamate (160 mg, 0.55 mmol), EDCI (154 mg, 1.2 mmol) and DMAP (145 mg, 1.2 mmol) in DMF (10 ml) was stirred at 67° C. overnight. The mixture was diluted with water and extracted with EA to afford compound 4 (200 mg, 55%) as a yellow oil.

Step 4: To the solution of compound 4 (200 mg, 0.32 mmol) in DCM (10 ml) was added TFA (2 ml), and the mixture was stirred at room temperature for 30 min. Concentration and washing with PE afforded compound 5 (250 mg, crude) as a brown oil.

Step 5: To the solution of compound 5 (250 mg, crude) and Et3N (106 mg, 1.05 mmol) in THF (5 ml) was added pyrrolidine-1-carbonyl chloride (70 mg, 0.5 mmol). The mixture was stirred at room temperature for 2 hours. The mixture was filtered through silica gel and washed with EA. Concentration and purification by Prep-HPLC afforded Compound 018 (61 mg, 60%). $^1$H NMR (400 MHz, DMSO) δ 9.72 (s, 1H), 8.91 (s, 2H), 7.53 (s, 1H), 7.42 (d, J=4.8 Hz, 1H), 7.39 (d, J=8.3 Hz, 1H), 7.32 (d, J=3.2 Hz, 1H), 7.12-7.04 (m, 1H), 6.95 (d, J=8.2 Hz, 1H), 6.85-6.13 (m, 1H), 3.70 (dd, J=13.5, 7.5 Hz, 4H), 3.29 (s, 4H), 3.07 (t, J=10.5 Hz, 2H), 2.81 (t, J=12.8 Hz, 2H), 2.11 (dd, J=14.5, 7.9 Hz, 2H), 1.93-1.84 (m, 2H), 1.76 (s, 4H), 1.32 (d, J=12.1 Hz, 2H). LCMS: m/z=532 (M+H)$^+$.

-continued

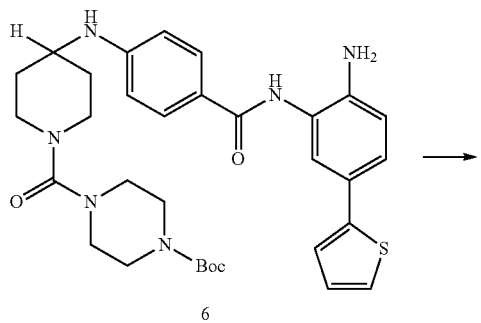
6

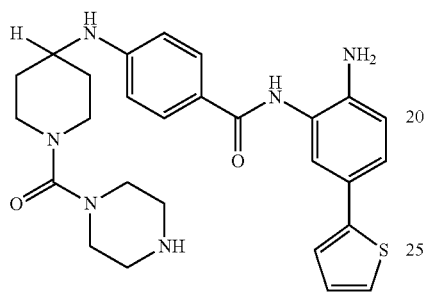

Step 1: A mixture of methyl 4-bromobenzoate (2.1 g, 10 mmol, 1 eq), compound 1 (6.0 g, 30 mmol, 3 eq), Pd2(dba)3 (915 mg, 1 mmol, 0.1 eq), Xantphos (478 mg, 1 mmol, 0.1 eq) and Cs2CO3 (9.75 g, 30 mmol, 3 eq) in toluene (30 ml) was stirred at 95° C. under nitrogen atmosphere overnight. The mixture was cooled, and addition of EA (100 ml), filtration and concentration yielded a residue, which was purified by silica gel column to afford compound 2 (1.97 g, 59%) as a light yellow solid.

Step 2: To a solution of compound 2 (3.34 g, 10 mmol) in EtOH (15 ml) and THF (15 ml) was added aqueous NaOH (2M, 15 ml) and stirred at 60° C. for 5 h. The mixture was concentrated to get a residue. The mixture was diluted with water (100 ml), and addition of aqueous citric acid to pH<7 at 0° C. and filtration afforded compound 3 (3.07 g, 96%) as a white solid.

Step 3: A mixture of compound 3 (3.2 g, 10 mmol, 1 eq), Boc-amine (2.6 g, 9 mmol, 0.9 eq), EDCI (5.7 g, 30 mmol, 3 eq) in Py (15 ml) was stirred at 25° C. overnight. To the mixture was added EA (100 ml) and aqueous citric acid (50 ml), and the mixture was stirred for 30 mins. The organic layer was separated, dried and concentrated to yield a residue, which was purified by silica gel column to afford compound 4 (3.7 g, 70%) as a light yellow solid.

Step 4: To a solution of compound 4 (2.96 g, 5 mmol) in DCM (20 ml) was added TFA (20 ml), and the mixture was stirred at room temperature for 1 h. The mixture was concentrated to yield a residue. To the mixture was added water (100 ml) and NaOH (2M solution) to adjust to pH>7, and the mixture was filtered to yield compound 5 (1.86 g, 95%) as a light yellow solid.

Step 5: To the solution of compound 5 (100 mg, 0.25 mmol) and Et3N (50 mg, 0.5 mmol) in THF (5 ml) was added tert-butyl 4-(chlorocarbonyl)piperazine-1-carboxylate (68 mg, 0.275 mmol), and the mixture was stirred at room temperature for 2 hours. After completion, the mixture was concentrated to afford the crude compound 6 (110 mg) for the next step.

Step 6: To a solution of compound 6 (110 mg, crude) in DCM (5 ml) was added TFA (2 ml) slowly. The mixture was stirred at room temperature for 2 h. Then the mixture was concentrated to get a residue, which was purified by Prep-HPLC to yield Compound 019 (40 mg, 32%, 2 steps) as a white solid. $^1$H NMR (400 MHz, DMSO) δ 9.37 (s, 1H), 8.71 (s, 2H), 7.79 (d, J=8.7 Hz, 2H), 7.45 (d, J=2.1 Hz, 1H), 7.36 (d, J=5.1 Hz, 1H), 7.30-7.20 (m, 3H), 7.05 (dd, J=5.1, 3.6 Hz, 1H), 6.81 (d, J=8.3 Hz, 1H), 6.66 (d, J=8.8 Hz, 2H), 3.63 (d, J=13.5 Hz, 2H), 3.48-3.42 (m, 1H), 3.30 (s, 4H), 3.11 (s, 4H), 2.96 (t, J=11.9 Hz, 2H), 1.92 (d, J=9.8 Hz, 2H), 1.34 (d, J=10.8 Hz, 2H), 1.05 (t, J=7.0 Hz, 1H). LCMS: m/z=505 (M+H)$^+$.

Example 20

Synthesis of Compound 020

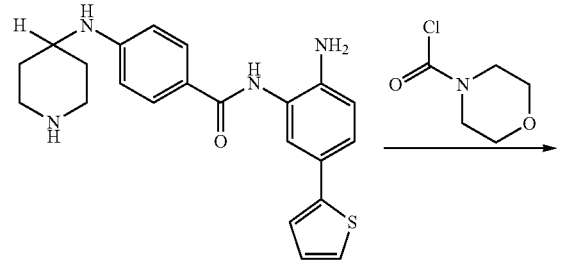

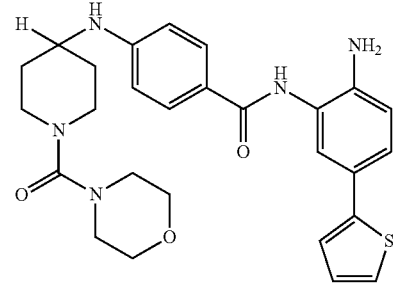

Steps 1-4: Refer to steps 1-4 of Example 19 to obtain compound 5.

Step 5: To the solution of compound 5 (100 mg, 0.25 mmol) and Et3N (50 mg, 0.5 mmol) in THF (5 ml) was added tert-butyl 4-(chlorocarbonyl)piperazine-1-carboxylate (41 mg, 0.275 mmol), and the mixture was stirred at room temperature for 2 hours. Then the mixture was concentrated to get a residue, which was purified by Prep-HPLC to afford Compound 020 (32 mg, 25%) as a white solid. $^1$H NMR (400 MHz, DMSO) δ 9.37 (s, 1H), 7.78 (d, J=8.6 Hz, 2H), 7.45 (d, J=2.0 Hz, 1H), 7.36 (d, J=4.4 Hz, 1H), 7.30-7.20 (m, 2H), 7.05 (dd, J=5.0, 3.7 Hz, 1H), 6.80 (d, J=8.3 Hz, 1H), 6.65 (d, J=8.8 Hz, 2H), 6.20 (d, J=7.9 Hz, 1H), 5.07 (s, 2H), 3.60-3.52 (m, 6H), 3.18-3.06 (m, 4H), 2.92 (t, J=11.6 Hz, 2H), 2.08 (s, 1H), 1.91 (d, J=10.2 Hz, 2H), 1.33 (dd, J=20.7, 9.8 Hz, 2H). LCMS: m/z=506 (M+H)$^+$.

Example 21

Synthesis of Compound 021

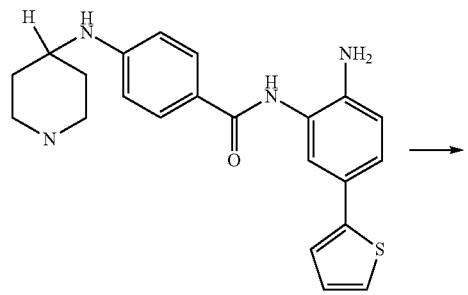

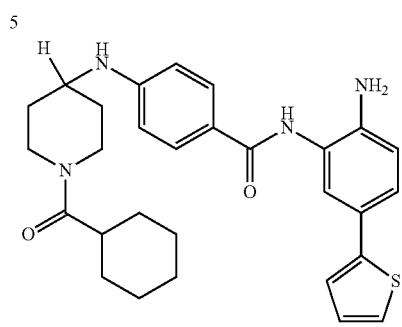

Steps 1-4: Refer to steps 1-4 of Example 19 to obtain compound 5.

Step 5: To the solution of compound 5 (100 mg, 0.25 mmol) and Et3N (50 mg, 0.5 mmol) in THF (5 ml) was added cyclohexanecarbonyl chloride (41 mg, 0.275 mmol), and the mixture was stirred at room temperature for 2 hours. Then the mixture was concentrated to get a residue, which was purified by Prep-HPLC to afford Compound 021 (30 mg, 24%) as a white solid. $^1$H NMR (400 MHz, DMSO) δ 9.61 (s, 1H), 7.81 (d, J=8.6 Hz, 2H), 7.53 (d, J=1.8 Hz, 1H), 7.43 (d, J=4.8 Hz, 1H), 7.38 (d, J=8.3 Hz, 1H), 7.33 (d, J=3.3 Hz, 1H), 7.13-7.05 (m, 1H), 6.98 (d, J=8.4 Hz, 1H), 6.68 (d, J=8.7 Hz, 2H), 4.29 (d, J=11.3 Hz, 1H), 3.92 (d, J=12.5 Hz, 1H), 3.66-3.57 (m, 1H), 3.27-3.13 (m, 1H), 2.85-2.73 (m, 1H), 2.67-2.56 (m, 1H), 2.03-1.88 (m, 2H), 1.75-1.58 (m, 5H), 1.37-1.12 (m, 7H). LCMS: m/z=503 (M+H)$^+$.

Example 22

Synthesis of Compound 022

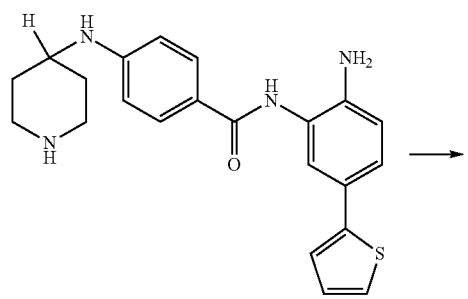

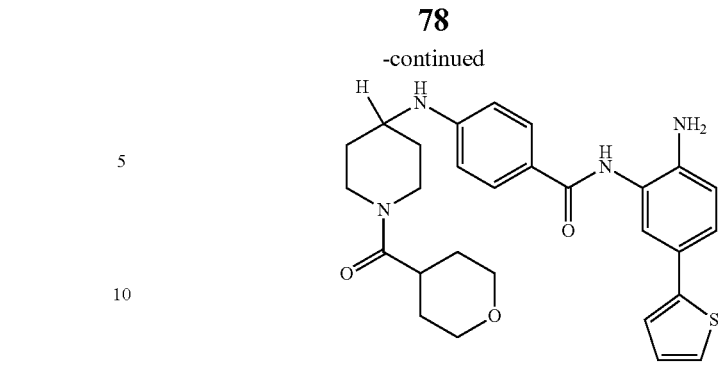

Steps 1-4: Refer to steps 1-4 of Example 19 to obtain compound 5.

Step 5: To the solution of compound 5 (100 mg, 0.25 mmol) and Et3N (50 mg, 0.5 mmol) in THF (5 ml) was added tetrahydro-2H-pyran-4-carbonyl chloride (41 mg, 0.275 mmol), and the mixture was stirred at room temperature for 2 hours. Then the mixture was concentrated to get a residue, which was purified by Prep-HPLC to afford Compound 022 (20 mg, 16%) as a white solid. $^1$H NMR (400 MHz, DMSO) δ 9.57 (s, 1H), 7.80 (d, J=8.6 Hz, 2H), 7.52 (s, 1H), 7.46-7.29 (m, 3H), 7.1-7.06 (m, 1H), 6.96 (s, 1H), 6.68 (d, J=8.6 Hz, 2H), 4.29 (d, J=14.4 Hz, 1H), 3.97 (d, J=13.9 Hz, 1H), 3.85 (d, J=9.7 Hz, 2H), 3.71-3.55 (m, 1H), 3.39 (t, J=11.5 Hz, 2H), 3.22 (t, J=11.6 Hz, 1H), 2.98-2.87 (m, 1H), 2.81 (t, J=12.1 Hz, 1H), 2.08-1.86 (m, 2H), 1.68-1.43 (m, 4H), 1.39-1.13 (m, 2H). LCMS: m/z=505 (M+H)$^+$.

Example 23

Synthesis of Compound 023

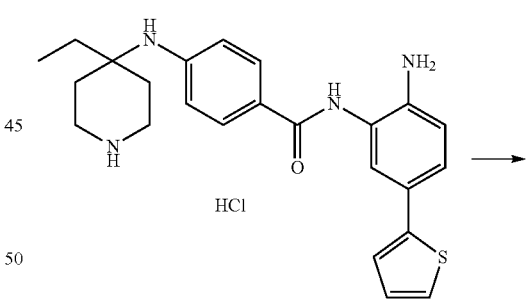

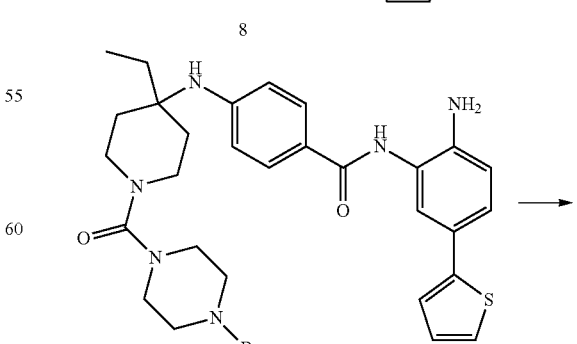

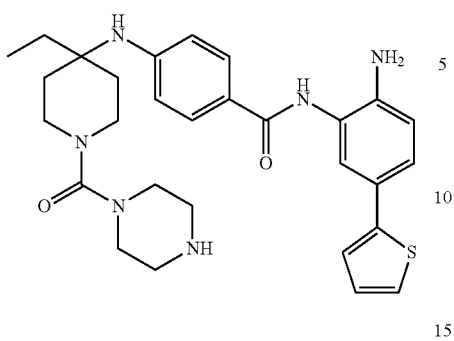

Steps 1-7: Refer to steps 1-7 of Example 17 to obtain compound 8.

Step 8: To a mixture of the compound 8 (175 mg, 0.4 mmol) and Et3N (106 mg, 1.05 mmol) in THF (5 ml) was added tert-butyl 4-(chlorocarbonyl) piperazine-1-carboxylate (125 mg, 0.5 mmol). The mixture was stirred at room temperature for 2 hours. Filtration through silica gel and washing with EA yielded compound 9 (175 mg, 67%) as a yellow oil.

Step 9: To the solution of the compound 9 (175 mg, 0.28 mmol) in 1,4-dioxane (10 ml) was added HCl/1,4-dioxane (5 ml, 20 mmol) at room temperature followed by stirring overnight. Concentration and washing with PE to afforded target Compound 023 (92 mg, 63%) as a yellow solid. $^1$H NMR (400 MHz, DMSO) δ 10.21 (s, 1H), 9.30 (s, 3H), 7.91 (d, J=8.1 Hz, 2H), 7.81 (s, 1H), 7.59 (d, J=5.9 Hz, 2H), 7.51 (d, J=3.3 Hz, 1H), 7.45 (d, J=8.4 Hz, 1H), 7.19-7.12 (m, 1H), 6.90 (s, 2H), 3.48-3.41 (m, 1H), 3.33 (s, 4H), 3.18-3.10 (m, 2H), 3.06 (s, 4H), 2.04 (d, J=13.0 Hz, 2H), 1.77 (d, J=7.0 Hz, 2H), 1.59-1.48 (m, 2H), 1.08-1.02 (m, 2H), 0.78 (t, J=7.0 Hz, 3H). LCMS: m/z=533 (M+H)$^+$.

Example 24

Synthesis of Compound 024

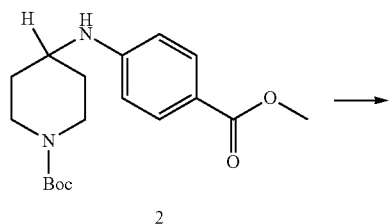

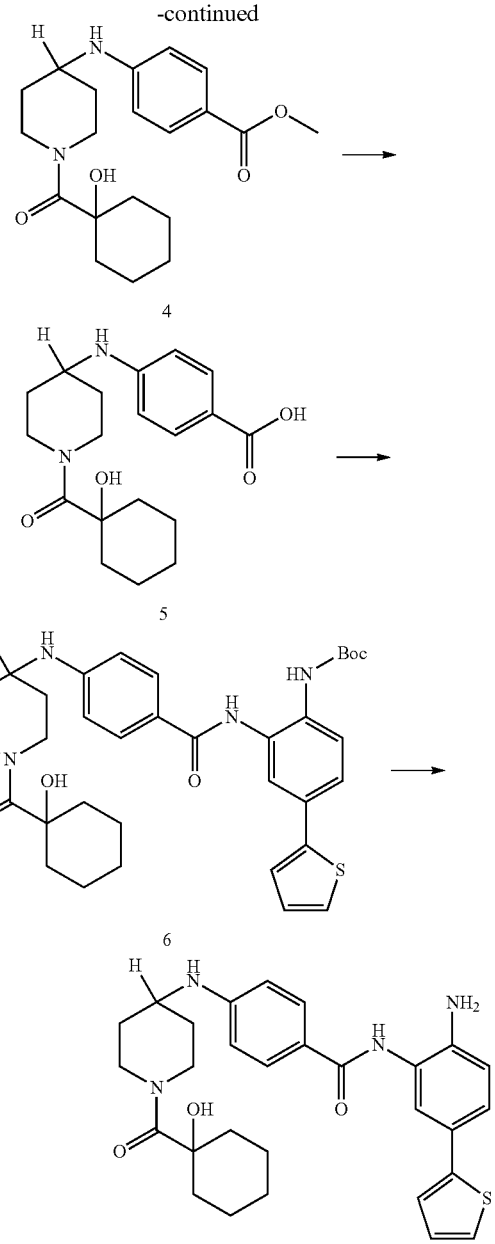

Step 1: A solution of the compound 2 (300 mg, 0.90 mmol) in TFA (5 ml) was stirred at room temperature overnight. Then concentration and washing with PE yielded target compound 3 (200 mg, 95%) as a gray solid.

Step 2: A mixture of the compound 3 (180 mg, 0.77 mmol), 1-hydroxycyclohexane-carboxylic acid (111 mg, 0.77 mmol), HATU (351 mg, 0.92 mmol) and DIPEA (199 mg, 1.5 mmol) in DMF (10 ml) was formed. The reaction was stirred at room temperature for 2 hours. The mixture was dissolved in water and extracted with EA. The organic layers were washed with water and brine then dried over sodium sulfate, filtered and concentrated. Then purification by silica gel column with EA:PE=1:2 yielded compound 4 (150 mg, 54%) as a purple solid.

Step 3: The solution of compound 4 (150 mg, 0.42 mmol) and 2N NaOH (10 ml, 20 mmol) in THF (10 ml) and EtOH (10 ml) was stirred at 60° C. for 6 hours. Then the mixture was concentrated, and the pH of the water phase was adjusted to 5-6 followed by extraction with EA. The organic layers were washed with water and brine then dried over sodium sulfate, filtered and concentrated to yield the target compound 5 (130 mg, 90%) as a white solid.

Step 4: A mixture of the compound 5 (70 mg, 0.2 mmol), tert-butyl 2-amino-4-(thiophen-2-yl)phenylcarbamate (59.0 mg, 0.2 mmol), EDCI (39.0 mg, 0.3 mmol), HOAT (41 mg, 0.3 mmol) and DIPEA (52 mg, 0.4 mmol) in DMF (10 ml) was formed. The mixture was stirred at 65° C. overnight. Then the mixture was dissolved in water and extracted with EA. The organic layers were washed with water and brine then dried over sodium sulfate, filtered and concentrated. Then purification by silica gel column with EA:PE=1:2 yielded compound 6 (20 mg, 16%) as a purple solid.

Step 5: To the solution of the compound 6 (20 mg, 0.03 mmol) in DCM (10 ml) was added HCl/1,4-dioxane (2 ml, 8.0 mmol) followed by stirring at room temperature overnight. Concentration and washing with PE afforded the target Compound 024 (12 mg, 71%) as a white solid. $^1$H NMR (400 MHz, DMSO) δ 9.41 (s, 1H), 7.80 (d, J=8.5 Hz, 2H), 7.46 (s, 1H), 7.36 (d, J=4.9 Hz, 1H), 7.30-7.22 (m, 2H), 7.09-7.03 (m, 1H), 6.80 (d, J=8.4 Hz, 1H), 6.66 (d, J=8.6 Hz, 2H), 6.26 (d, J=7.9 Hz, 1H), 5.24 (s, 1H), 5.09 (s, 2H), 2.04-1.87 (m, 3H), 1.76-1.39 (m, 10H), 1.35-1.14 (m, 6H). LCMS: m/z=519 (M+H)$^+$.

Example 25

Synthesis of Compound 025

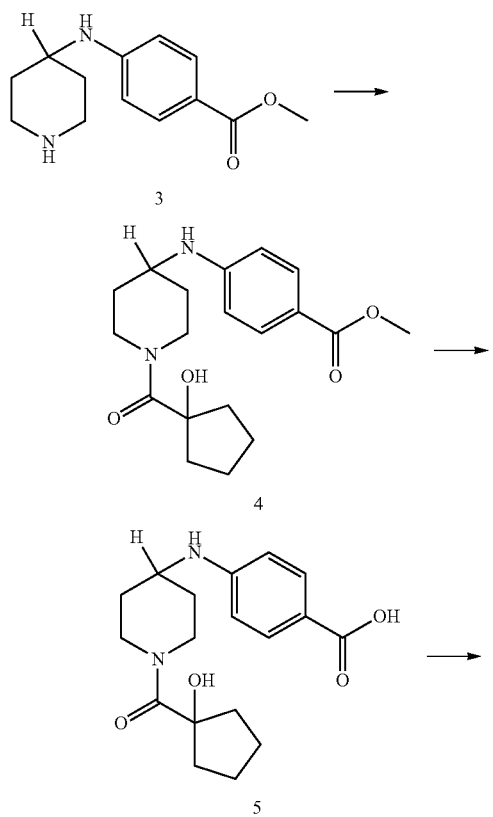

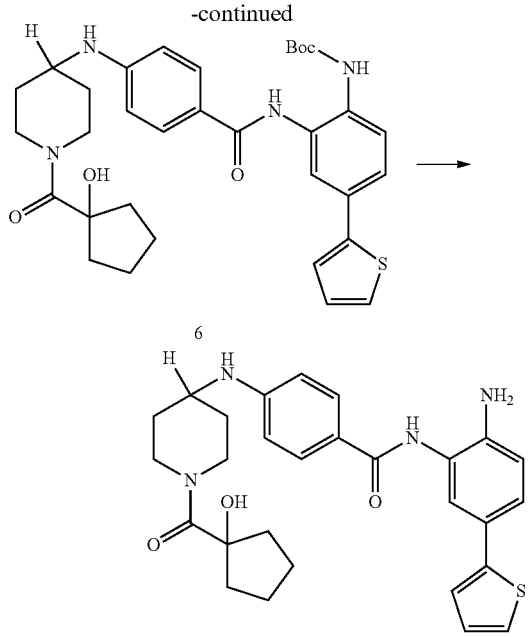

Step 1: Refer to step 1 of Example 24 to obtain compound 3.

Step 2: A mixture of the compound 3 (400 mg, 1.7 mmol), 1-hydroxycyclopentane-carboxylic acid (222 mg, 1.7 mmol), HATU (969 mg, 2.6 mmol) and DIPEA (439 mg, 3.4 mmol) in DMF (10 ml) was formed. The mixture was stirred at room temperature for 2 hours. The mixture was dissolved in water and extracted with EA. organic layers were washed with water and brine then dried over sodium sulfate, filtered and concentrated. Then purification by silica gel column with EA:PE=1:2 yielded compound 4 (300 mg, 51%) as a purple solid.

Step 3: To a solution of compound 4 (300 mg, 0.87 mmol) in THF (10 ml) and EtOH (10 ml) was added 2N NaOH (10 ml, 20 mmol) at 60° C., and the resulting reaction mixture was stirred for 6 hours. Concentration and adjustment of the pH of the water phase to 5-6 was followed by extraction with EA (2*15 ml). The organic layers were washed with water and brine then dried over sodium sulfate, filtered and concentrated to yield target compound 5 (250 mg, 87%) as a white solid.

Step 4: A mixture of the compound 5 (250 mg, 0.75 mmol), tert-butyl 2-amino-4-(thiophen-2-yl)phenylcarbamate (218 mg, 0.75 mmol), EDCI (143.0 mg, 1.1 mmol), HOAT (147 mg, 1.1 mmol) and DIPEA (194 mg, 1.5 mmol) in DMF (10 ml) was formed. The reaction was stirred at 65° C. overnight. Then the mixture was dissolved in water and extracted with EA. The organic layers were washed with water and brine then dried over sodium sulfate, filtered and concentrated. Then purification by silica gel column with EA:PE=1:2 yielded compound 6 (50 mg, 11%) as a purple solid.

Step 5: To a solution of the compound 6 (50 mg, 0.08 mmol) in DCM was added HCl/1,4-dioxane (2 ml, 8.0 mmol). The mixture was stirred at room temperature overnight. Concentration and washing with PE afforded the target Compound 025 (13 mg, 32%) as a white solid. $^1$H NMR (400 MHz, DMSO) δ 9.61 (s, 1H), 7.81 (d, J=8.6 Hz, 2H), 7.53 (s, 1H), 7.46-7.30 (m, 3H), 7.11-7.07 (m, 1H), 6.98 (d, J=8.0 Hz, 1H), 6.68 (d, J=8.7 Hz, 2H), 4.57-4.44 (m, 1H), 4.36-4.19 (m, 1H), 3.24-3.17 (m, 1H), 2.90-2.79 (m, 1H), 2.39-2.25 (m, 1H), 2.08-1.91 (m, 4H), 1.74-1.63 (m, 4H), 1.57-1.52 (m, 2H), 1.38-1.22 (m, 2H). LCMS: m/z=505 (M+H)+.

Example 26

Synthesis of Compound 026

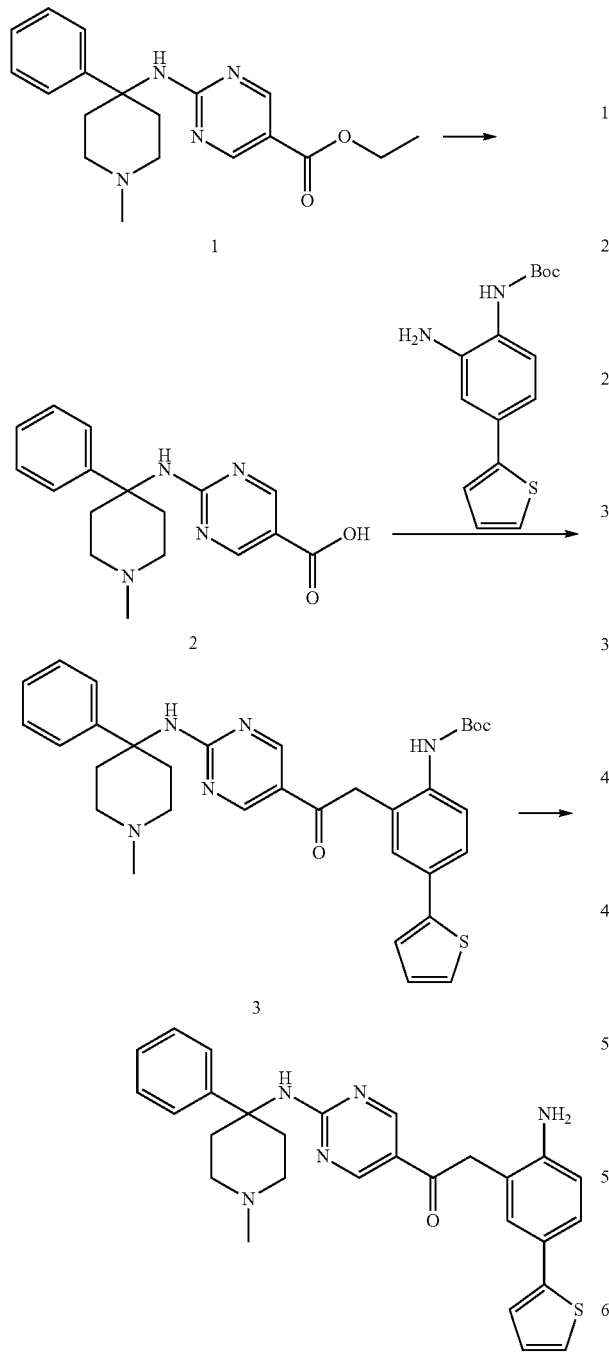

Step 1: To a mixture of compound 1 (300 mg, 0.88 mmol) in THF (5 ml) and EtOH (5 ml) was added 2M NaOH (over 5 m), and the resulting reaction mixture was stirred at 60° C. for 5 h. The mixture was concentrated to afford a residue, which was purified by flash column to yield compound 2 (180 mg, yield: 65%) as a yellow solid.

Step 2: A mixture of compound 2 (150 mg, 0.48 mmol), compound Boc-amine (139 mg, 0.48 mmol), HOAT (131 mg, 096 mmol), and EDCI (183 mg, 0.96 mmol) in DMF (4 ml) was stirred at 60° C. overnight. To the mixture was added EA (30 ml) and aqueous saturated NaCl (100 ml), and the resulting reaction mixture was stirred for 30 min. The organic layer was separated, washed with aqueous saturated NaCl (50 ml*2), dried and concentrated to afford a residue, which was purified by Prep-TLC to yield compound 3 (100 mg, 35%) as a yellow solid.

Step 3: To a solution of compound 3 (100 mg, 0.17 mmol) in DCM (3 ml) was added TFA (3 ml), and the resulting reaction mixture was stirred at room temperature for 2 h. The mixture was concentrated to get a residue, which was purified by Prep-HPLC to afford Compound 026 (20 mg, 24%) as a white solid. $^1$H NMR (400 MHz, DMSO) δ 9.53 (s, 1H), 8.76 (d, J=86.5 Hz, 2H), 8.41 (d, J=13.8 Hz, 1H), 7.43-7.38 (m, 3H), 7.37-7.31 (m, 3H), 7.29 (dd, J=8.3, 2.2 Hz, 1H), 7.22 (dd, J=7.7, 4.2 Hz, 2H), 7.04 (dd, J=5.1, 3.6 Hz, 1H), 6.79 (d, J=8.4 Hz, 1H), 3.46 (d, J=11.2 Hz, 2H), 3.34-3.20 (m, 2H), 2.96-2.90 (m, 2H), 2.86 (d, J=4.5 Hz, 3H), 2.26-2.08 (m, 2H). LCMS: m/z=485 (M+H)+.

Example 27

Synthesis of Compound 027

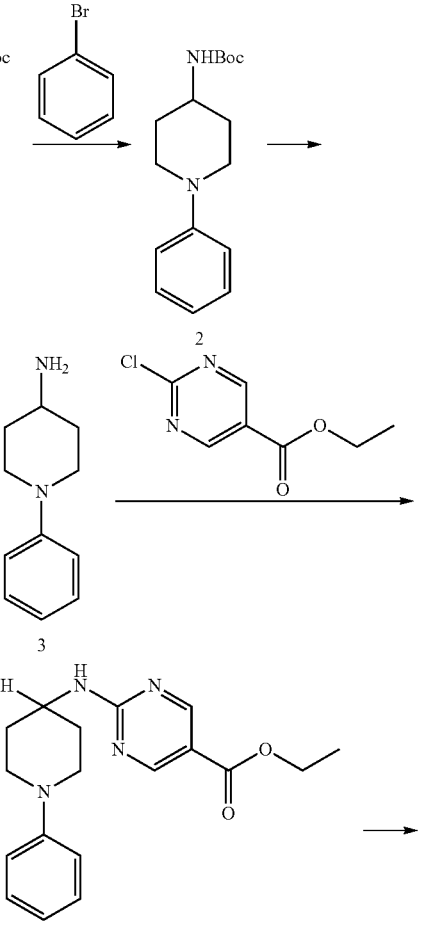

-continued

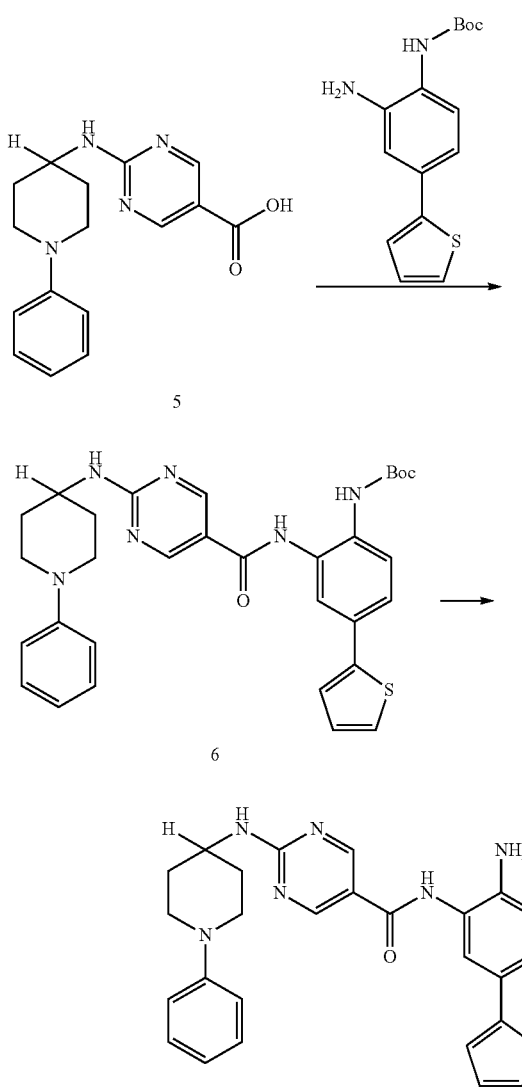

Step 1: A mixture of compound 1 (3.0 g, 15 mmol), bromobenzene (7.0 g, 45 mmol), Pd2(dba)3 (1.4 g, 1.5 mmol), Ruphos (700 mg, 1.5 mmol) and Cs2CO3 (14.6 g, 45 mmol) in toluene (100 ml) was stirred at 95° C. under a nitrogen atmosphere overnight. The mixture was filtered and concentrated followed by washing with PE (30 ml) to afford compound 2 (3.5 g, yield: 85%) as a light yellow solid.

Step 2: To a solution of compound 2 (3.5 g, 12.6 mmol) in 1,4-dioxane (50 ml) was added HCl in 1,4-dioxane (9.45 ml, 37.8 mmol) at room temperature, and the mixture was stirred overnight. The mixture was filtered to afford compound 3 (2.0 g, 90%) as a white solid.

Step 3: A mixture of compound 3 (500 mg, 2.8 mmol), ethyl 2-chloropyrimidine-5-carboxylate (352 mg, 1.9 mmol), and NEt3 (576 mg, 5.7 mmol) in 1,4-dioxane (15 ml) was stirred at 60° C. overnight. To the mixture was added EA (100 ml) and aqueous saturated citric acid (30 ml), and the resulting reaction mixture was stirred for 30 min. The organic layer was separated, washed by aqueous saturated NaCl (50 ml*2), dried and concentrated, and washed by PE (30 ml) to yield compound 4 (500 mg, 81%) as a yellow solid.

Step 4: To a solution of compound 4 (500 mg, 1.5 mmol) in EtOH (15 ml) and THF (15 ml) was added aqueous NaOH (2M, 15 ml), and the resulting reaction mixture was stirred at 60° C. for 5 h. To the mixture was added aqueous saturated citric acid to adjust to pH<7 followed by filtration to yield compound 5 (400 mg, 87%) as a white solid.

Step 5: A mixture of compound 5 (150 mg, 0.5 mmol), compound Boc-amine (145 mg, 0.5 mmol), HOAT (136 mg, 1 mmol), EDCI (191 mg, 1 mmol) and NEt3 (202 mg, 2 mmol) in DMF (5 ml) was stirred at 60° C. overnight. To the mixture was added EA (100 ml) and aqueous saturated NaCl (100 ml), and the resulting reaction mixture was stirred for 30 min. The organic layer was separated, washed by aqueous saturated NaCl (50 ml*2), dried and concentrated, and washed by CH3CN (10-20 mL) to afford compound 6 (140 mg, 49%) as a yellow solid.

Step 6: To a solution of compound 6 (140 mg, 0.25 mmol) in DCM (5 ml) was added TFA (3 ml) at room temperature, and the resulting reaction mixture was stirred for 2 h. The mixture was concentrated and purified by Prep-HPLC to afford Compound 027 (110 mg, 95%) as a white solid. $^1$H NMR (500 MHz, DMSO) δ 9.52 (s, 1H), 8.86 (s, 2H), 7.87 (d, J=7.8 Hz, 1H), 7.45 (s, 1H), 7.35 (d, J=4.9 Hz, 1H), 7.29 (d, J=8.3 Hz, 1H), 7.25-7.18 (m, 3H), 7.07-7.02 (m, 1H), 6.96 (d, J=8.2 Hz, 2H), 6.83-6.73 (m, 2H), 5.20 (s, 2H), 3.72 (d, J=12.2 Hz, 2H), 2.82 (t, J=11.7 Hz, 2H), 1.99 (s, 1H), 1.96 (d, J=10.5 Hz, 2H), 1.69-1.58 (m, 2H). LCMS: m/z=471 (M+H)$^+$.

Example 28

Synthesis of Compound 028

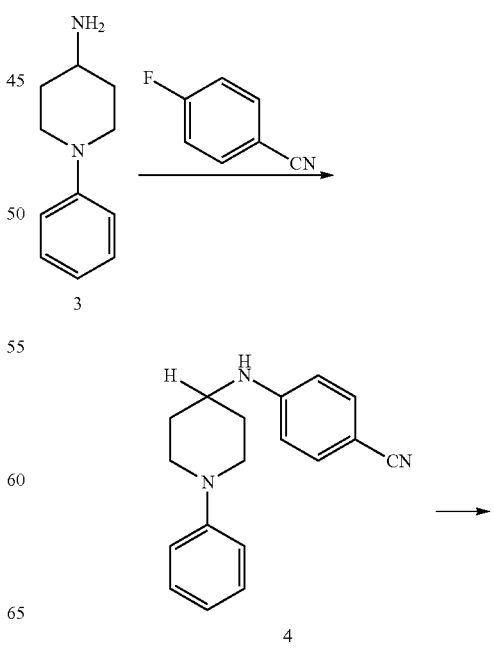

-continued

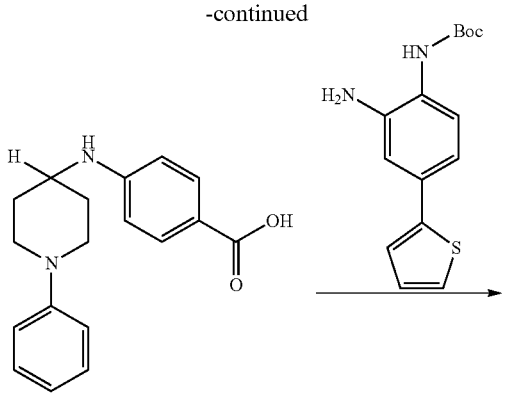

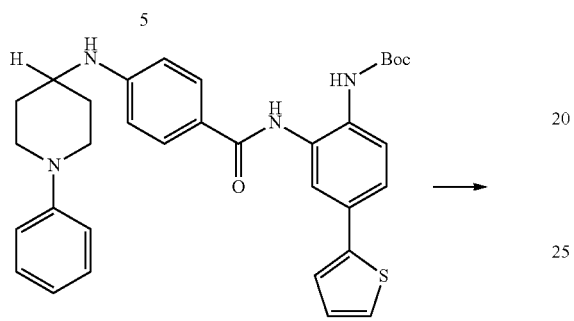

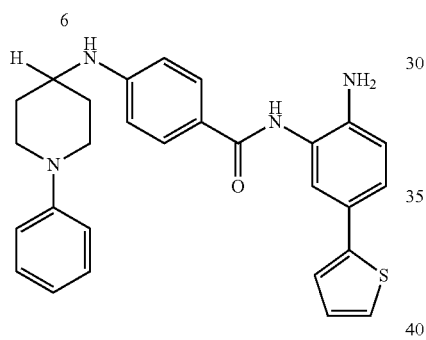

Steps 1-2: Refer to steps 1-2 of Example 27 to obtain compound 3.

Step 3: A mixture of compound 3 (300 mg, 1.7 mmol), 4-fluorobenzonitrile (181 mg, 1.5 mmol), and K2CO3 (414 mg, 3 mmol) in DMSO (10 ml) was stirred at 100° C. overnight. To the mixture was added EA (100 ml) and aqueous saturated citric acid (30 ml), and the resulting reaction mixture was stirred for 30 min. The organic layer was separated, washed by aqueous saturated NaCl (50 ml*2), dried and concentrated, and purified by silica gel column to yield compound 4 (300 mg, 72%) as a yellow solid.

Step 4: A solution of compound 4 (300 mg, 1.1 mmol) in 6M HCl (20 ml) was stirred at 80° C. for 3 days. The mixture was filtered to afford compound 5 (250 mg, 78%) as a white solid.

Step 5: A mixture of compound 5 (150 mg, 0.5 mmol), compound Boc-amine (145 mg, 0.5 mmol), HOAT (136 mg, 1 mmol), EDCI (191 mg, 1 mmol) and NEt3 (202 mg, 2 mmol) in DMF (5 ml) was stirred at 60° C. overnight. To the mixture was added EA (80 ml) and aqueous saturated NaCl (80 ml), and the resulting reaction mixture was stirred for 30 min. The organic layer was separated, washed by aqueous saturated NaCl (30 ml*2), dried and concentrated, and purified by Prep-TLC to afford compound 6 (50 mg, 18%) as a yellow solid.

Step 6: To a solution of compound 6 (50 mg, 0.09 mmol) in DCM (5 ml) was added TFA (3 ml) at room temperature, and the resulting reaction mixture was stirred for 2 h. The mixture was concentrated and purified by Prep-HPLC to afford Compound 028 (5 mg, 12%) as a white solid. $^1$H NMR (500 MHz, DMSO) δ 9.36 (s, 1H), 7.79 (d, J=8.6 Hz, 2H), 7.46 (d, J=1.9 Hz, 1H), 7.35 (d, J=5.0 Hz, 1H), 7.27 (dd, J=8.3, 2.0 Hz, 1H), 7.25-7.18 (m, 3H), 7.08-7.03 (m, 1H), 6.96 (d, J=8.2 Hz, 2H), 6.80 (d, J=8.3 Hz, 1H), 6.75 (t, J=7.2 Hz, 1H), 6.67 (d, J=8.7 Hz, 2H), 6.22 (d, J=8.0 Hz, 1H), 5.07 (s, 2H), 3.70 (d, J=12.8 Hz, 2H), 3.53 (s, 1H), 2.89 (t, J=11.0 Hz, 2H), 2.01 (d, J=10.8 Hz, 2H), 1.51 (dd, J=20.6, 10.5 Hz, 2H). LCMS: m/z=469 (M+H)$^+$.

Example 29

Synthesis of Compound 029

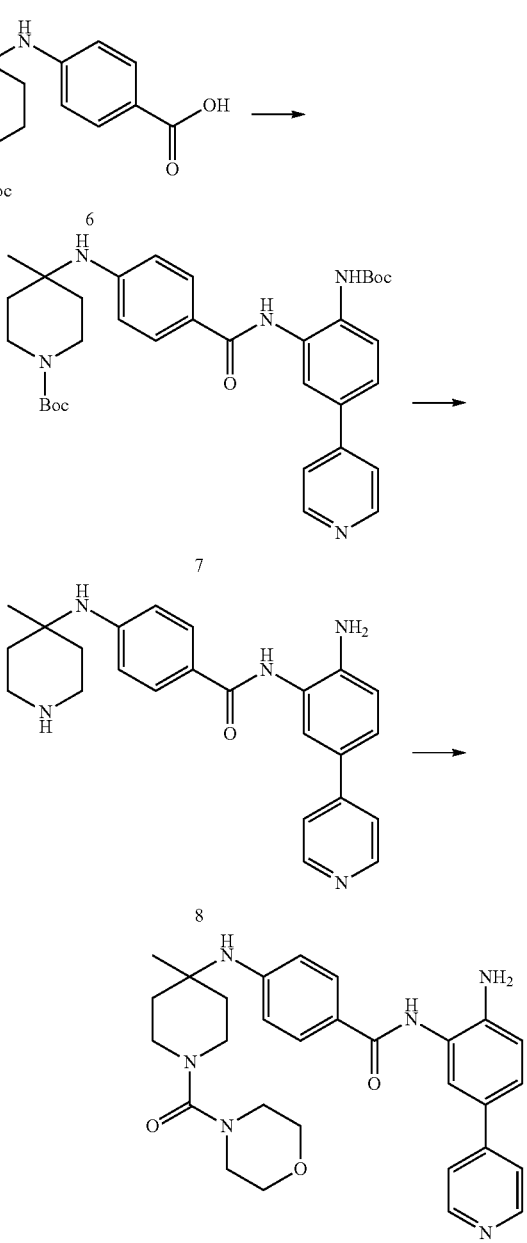

Steps 1-2: Refer to steps 1-2 of Example 13 to obtain compound 6.

Step 3: A mixture of compound 6 (630 mg, 1.89 mmol), compound Boc-amine (484 mg, 1.7 mmol), HOAT (510 mg, 3.78 mmol), EDCI (721 mg, 3.78 mmol) DIPEA (487 mg, 3.78 mmol) and DMAP (461 mg, 3.78 mmol) in DMF (25 ml) was stirred at 67° C. for 3 days. To the mixture was added EA (100 ml) and aqueous saturated NaCl (100 ml), and the resulting reaction mixture was stirred for 30 min. The organic layer was separated, washed by aqueous saturated NaCl (50 ml*2), dried and concentrated, and purified by silica gel column to afford compound 7 (473 mg, 46%) as a yellow solid.

Step 4: To a solution of compound 7 (250 mg, 0.42 mmol) in DCM (10 ml) was added TFA (3 ml) at room temperature, and the resulting reaction mixture was stirred for 2 h. The mixture was concentrated to afford compound 8 (300 mg, crude) and was used in the next step without further purification.

Step 5: To a solution of the compound 8 (150 mg, crude) and Et3N (50 mg, 0.5 mmol) in THF (5 ml) was added compound morpholine-4-carbonyl chloride (37 mg, 0.25 mmol) at 0° C., and the resulting reaction mixture was stirred for 2 h. To the mixture was added EA (10 ml) and aqueous saturated NaCl (10 ml), and the resulting reaction mixture was stirred for 30 min. The organic layer was separated, washed by aqueous saturated NaCl (10 ml*2), dried and concentrated, and purified by Prep-HPLC to afford Compound 029 (44 mg, 35%) as a white solid. $^1$H NMR (400 MHz, DMSO) δ 9.36 (s, 1H), 8.51 (dd, J=4.7, 1.5 Hz, 2H), 7.76 (d, J=8.8 Hz, 2H), 7.66 (d, J=2.1 Hz, 1H), 7.57 (dd, J=4.7, 1.6 Hz, 2H), 7.47 (dd, J=8.4, 2.2 Hz, 1H), 6.88 (d, J=8.4 Hz, 1H), 6.79 (d, J=8.8 Hz, 2H), 5.87 (s, 1H), 5.29 (s, 2H), 3.60-3.51 (m, 4H), 3.32-3.24 (m, 2H), 3.17-3.08 (m, 6H), 1.98 (d, J=13.8 Hz, 2H), 1.64-1.55 (m, 2H), 1.36 (s, 3H). LCMS: m/z=515 (M+H)$^+$.

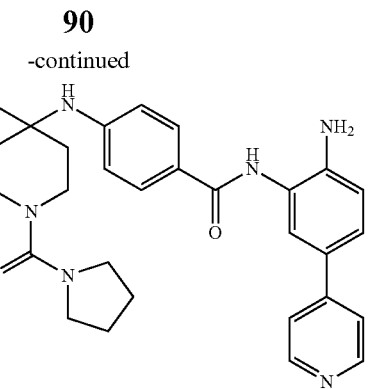

Steps 1-3: Refer to steps 1-3 of Example 29 to obtain compound 8.

Step 3: To a solution of the compound 8 (150 mg, crude) and Et3N (50 mg, 0.5 mmol) in THF (5 ml) was added compound pyrrolidine-1-carbonyl chloride (33 mg, 0.25 mmol) at 0° C., and the resulting reaction mixture was stirred for 2 h. To the mixture was added EA (10 ml) and aqueous saturated NaCl (10 ml), and the resulting reaction mixture was stirred for 30 min. The organic layer was separated, washed by aqueous saturated NaCl (10 ml*2), dried and concentrated, and purified by Prep-HPLC to afford Compound 030 (17 mg, 14%) as a white solid. $^1$H NMR (400 MHz, DMSO) δ 9.34 (d, J=10.2 Hz, 1H), 8.51 (d, J=5.5 Hz, 2H), 7.76 (d, J=8.6 Hz, 2H), 7.67 (d, J=1.8 Hz, 1H), 7.58 (d, J=5.9 Hz, 2H), 7.48 (dd, J=8.3, 1.9 Hz, 1H), 6.88 (d, J=8.4 Hz, 1H), 6.79 (d, J=8.6 Hz, 2H), 5.87 (s, 1H), 5.31 (s, 2H), 3.31-3.20 (m, 6H), 3.10 (t, J=10.5 Hz, 2H), 1.98 (d, J=13.5 Hz, 2H), 1.74 (s, 4H), 1.59 (t, J=10.1 Hz, 2H), 1.37 (s, 3H). LCMS: m/z=499 (M+H)$^+$.

Example 31

Synthesis of Compound 031

Example 30

Synthesis of Compound 030

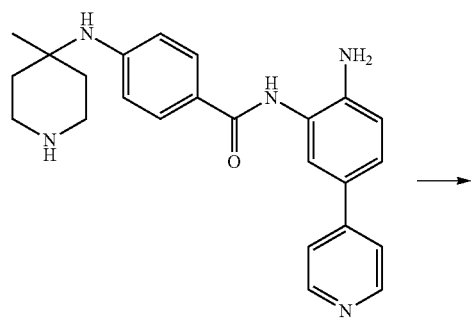

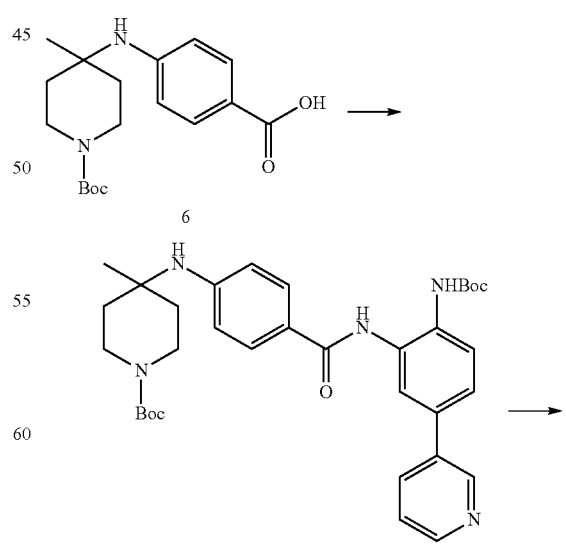

91

-continued

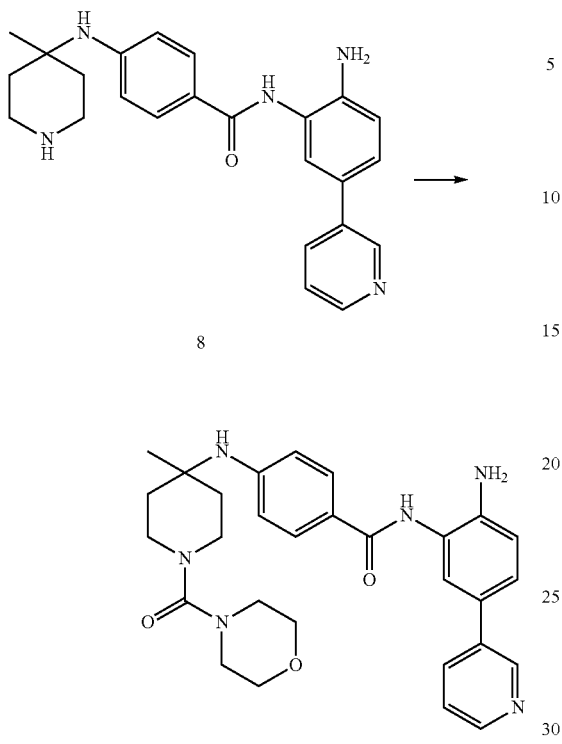

8

Step 1: A mixture of compound 6 (270 mg, 0.8 mmol), compound Boc-amine (205 mg, 0.72 mmol), HOAT (216 mg, 1.6 mmol), EDCI (305 mg, 1.6 mmol) DIPEA (206 mg, 1.6 mmol) and DMAP (195 mg, 1.6 mmol) in DMF (25 ml) was stirred at 67° C. for 3 days. To the mixture was added EA (60 ml) and aqueous saturated NaCl (60 ml), and the resulting reaction mixture was stirred for 30 min. The organic layer was separated, washed by aqueous saturated NaCl (20 ml*2), dried and concentrated, and purified by silica gel column to afford compound 7 (400 mg, 83%) as a yellow solid.

Step 2: To a solution of compound 7 (200 mg, 0.33 mmol) in DCM (10 ml) was added TFA (3 ml), and the resulting reaction mixture was stirred at room temperature for 2 h. The mixture was concentrated to afford compound 8 (250 mg, crude) and was used in the next step without further purification.

Step 3: To a solution of the compound 8 (150 mg, crude) and Et3N (50 mg, 0.5 mmol) in THF (5 ml) was added compound morpholine-4-carbonyl chloride (37 mg, 0.25 mmol) at 0° C., and the resulting reaction mixture was stirred for 2 h. To the mixture was added EA (10 ml) and aqueous saturated NaCl (10 ml), and the resulting reaction mixture was stirred for 30 min. The organic layer was separated, washed by aqueous saturated NaCl (10 ml*2), dried and concentrated, and purified by Prep-HPLC to afford Compound 031 (55 mg, 60%) as a white solid. $^1$H NMR (400 MHz, DMSO) δ 9.57 (s, 1H), 9.09 (s, 1H), 8.76-8.58 (m, 2H), 8.01-7.69 (m, 4H), 7.56 (d, J=7.2 Hz, 1H), 7.05-6.87 (m, 3H), 3.56 (s, 4H), 3.17 (d, J=39.8 Hz, 8H), 1.96 (s, 2H), 1.61 (s, 2H), 1.37 (s, 3H). LCMS: m/z=515 (M+H)$^+$.

92

Example 32

Synthesis of Compound 032

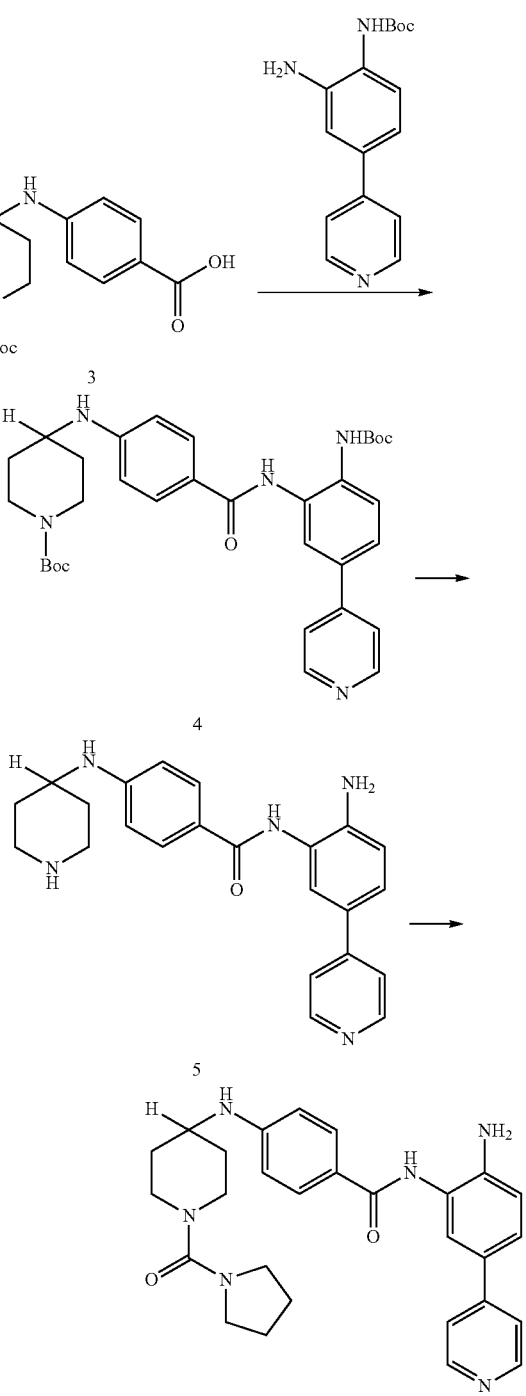

Steps 1-2: Refer to steps 1-2 of Example 19 to obtain compound 3.

Step 3: A mixture of compound 3 (150 mg, 0.45 mmol), compound Boc-amine (130 mg, 0.45 mmol), HOAT (103 mg, 0.76 mmol), EDCI (145 mg, 0.76 mmol) and NEt3 (154 mg, 1.52 mmol) in CH3CN (5 ml) was stirred at 60° C. overnight. To the mixture was added EA (10 ml) and aqueous saturated NaCl (10 ml), and the resulting reaction mixture was stirred for 30 min. The organic layer was separated, washed by aqueous saturated NaCl (10 ml*2), dried and concentrated, and purified by silica gel column to afford compound 4 (90 mg, 30%) as a yellow solid.

Step 4: To a solution of compound 4 (90 mg, 0.15 mmol) in DCM (5 ml) was added TFA (3 ml) at room temperature, and the resulting reaction mixture was stirred for 2 h. The mixture was concentrated to afford compound 5 (58 mg, crude) and was used in the next step without further purification.

Step 5: To a solution of the compound 5 (58 mg, 0.15 mmol) and Et3N (33 mg, 0.33 mmol) in THF (5 ml) was added compound pyrrolidine-1-carbonyl chloride (20 mg, 015 mmol) at 0° C., and the resulting reaction mixture was stirred for 2 h. The mixture was purified by Prep-HPLC to afford Compound 032 (12 mg, 17%) as a white solid. $^1$H NMR (400 MHz, DMSO) δ 9.37 (s, 1H), 8.58 (d, J=5.1 Hz, 2H), 7.79 (d, J=8.8 Hz, 4H), 7.76 (d, J=2.1 Hz, 1H), 7.59 (dd, J=8.5, 2.2 Hz, 1H), 6.89 (d, J=8.5 Hz, 1H), 6.66 (d, J=8.8 Hz, 2H), 6.22 (d, J=7.4 Hz, 1H), 3.63 (d, J=13.2 Hz, 2H), 3.26 (t, J=6.4 Hz, 4H), 2.87 (t, J=11.3 Hz, 2H), 1.91 (d, J=10.0 Hz, 2H), 1.75 (t, J=6.5 Hz, 4H), 1.34 (dd, J=20.2, 10.4 Hz, 2H). LCMS: m/z=485 (M+H)$^+$.

Example 33

Synthesis of Compound 033

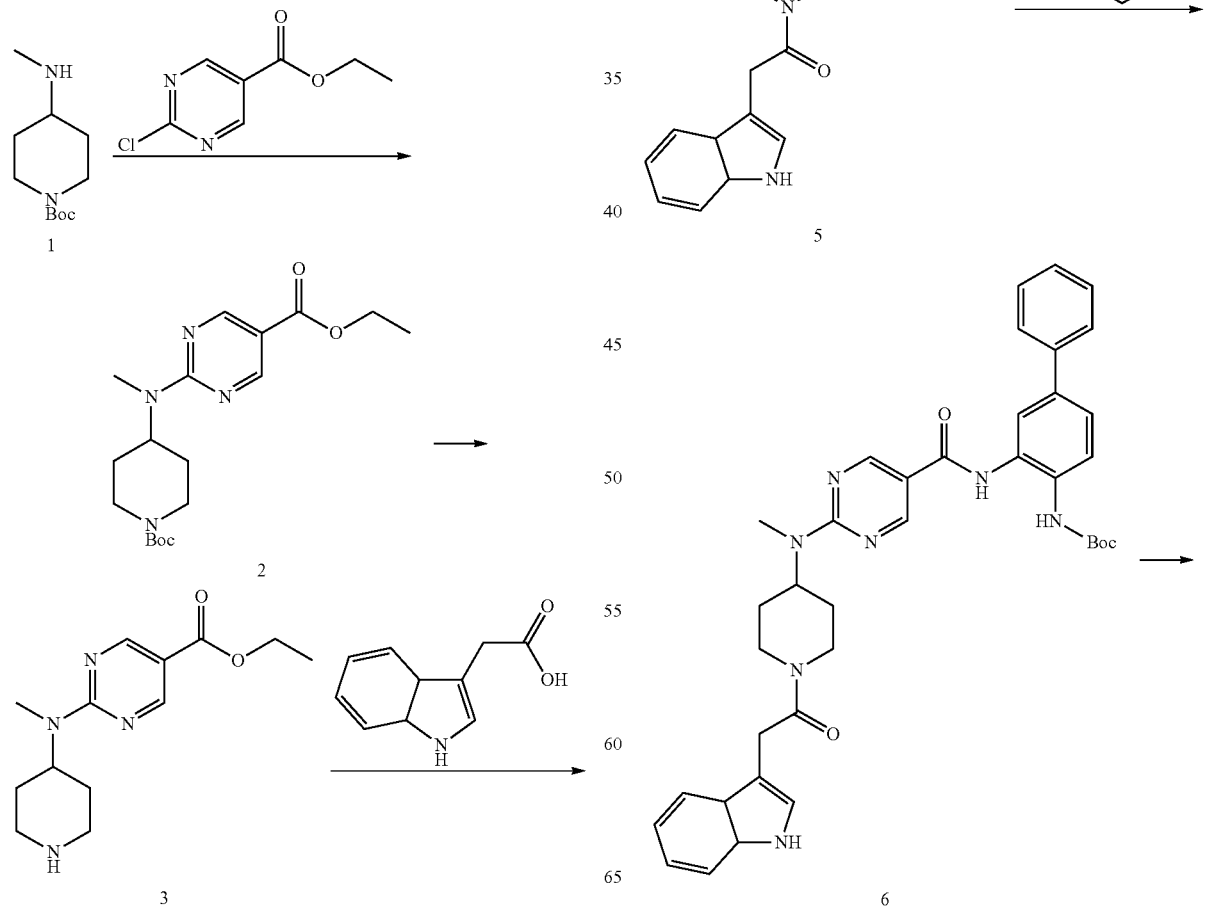

-continued

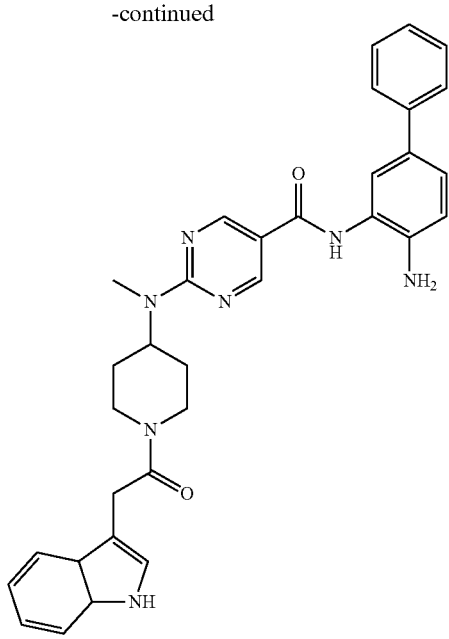

Step 1: A mixture of compound 1 (2.1 g, 9.6 mmol), ethyl 2-chloropyrimidine-5-carboxylate (600 mg, 3.2 mmol) and NEt3 (970 mg, 9.6 mmol) in 1,4-dioxane (20 ml) was stirred at 95° C. overnight. The mixture was concentrated followed by addition of EA (60 ml) and aqueous citric acid (60 ml), and the resulting reaction mixture was stirred for 30 min. The organic layer was separated, dried and concentrated to afford compound 2 (880 mg, yield: 75%) as a light yellow solid.

Step 2: To a solution of compound 2 (880 mg, 2.4 mmol) in DCM (10 ml) was added TFA (5 ml) at room temperature, and the resulting reaction mixture was stirred for 2 h. The mixture was concentrated to afford compound 3 (630 mg, 99%) as a yellow solid.

Step 3: A mixture of compound 3 (630 mg, 2.4 mmol), 2-indoleacetic acid (531 mg, 3 mmol), HOAT (816 mg, 6 mmol), EDCI (1.1 g, 6 mmol) and NEt3 (1.2 g, 12 mmol) in DMF (15 ml) was stirred at 60° C. overnight. To the mixture was added EA (100 ml) and aqueous saturated NaCl (100 ml), and the resulting reaction mixture was stirred for 30 min. The organic layer was separated, washed by aqueous saturated NaCl (50 ml*2), dried and concentrated to get a residue, which was purified by Prep-TLC to yield compound 4 (600 mg, 60%) as a yellow solid.

Step 4: To a solution of compound 4 (600 mg, 1.4 mmol) in EtOH (15 ml) and THF (15 ml) was added aqueous NaOH (2M, 15 ml), and the resulting reaction mixture was stirred at 60° C. for 5 h. The mixture was concentrated to yield a residue. To the mixture was added water (100 ml) and aqueous citric acid to adjust to pH<7 at 0° C., followed by filtration to yield compound 5 (400 mg, 72%) as a white solid.

Step 5: A mixture of compound 5 (150 mg, 0.38 mmol), compound Boc-amine (108 mg, 0.38 mmol), HOAT (103 mg, 0.76 mmol), EDCI (145 mg, 0.76 mmol) and NEt3 (154 mg, 1.52 mmol) in DMF (5 ml) was stirred at 60° C. overnight. To the mixture was added EA (20 ml) and aqueous saturated NaCl (20 mL), and the resulting reaction mixture was stirred for 30 min. The organic layer was separated, washed by aqueous saturated NaCl (20 ml*2), dried and concentrated, and purified by Prep-TLC to afford compound 6 (150 mg, 59%) as a yellow solid.

Step 6: To a solution of compound 6 (150 mg, 0.23 mmol) in DCM (5 ml) was added TFA (3 ml) at room temperature, and the resulting reaction mixture was stirred for 2 h. The mixture was concentrated and purified by Prep-HPLC to afford Compound 033 (28 mg, 22%) as a white solid. $^1$H NMR (500 MHz, DMSO) δ 10.94 (s, 1H), 9.75 (s, 1H), 8.91 (s, 2H), 7.58 (dd, J=15.8, 7.9 Hz, 5H), 7.41 (t, J=7.6 Hz, 4H), 7.36 (d, J=8.1 Hz, 1H), 7.31-7.24 (m, 3H), 7.08 (t, J=7.5 Hz, 1H), 7.01-6.97 (m, 2H), 4.84 (d, J=11.4 Hz, 2H), 4.58 (d, J=14.0 Hz, 2H), 4.14 (d, J=11.9 Hz, 1H), 3.82 (q, J=15.1 Hz, 3H), 3.09 (t, J=12.1 Hz, 1H), 2.82 (s, 3H), 2.63 (t, J=12.0 Hz, 1H), 1.63-1.44 (m, 5H), 1.31 (d, J=8.2 Hz, 2H). LCMS: m/z=562 (M+H)$^+$.

Example 34

Synthesis of Compound 034

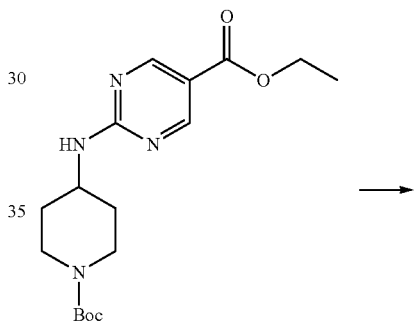

2

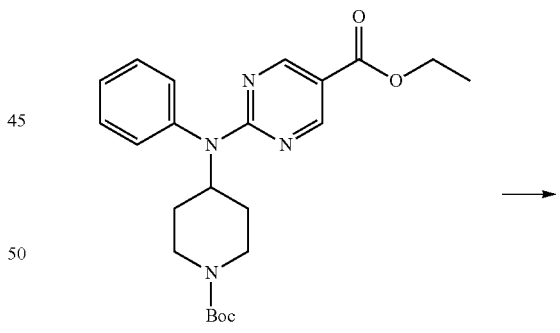

3

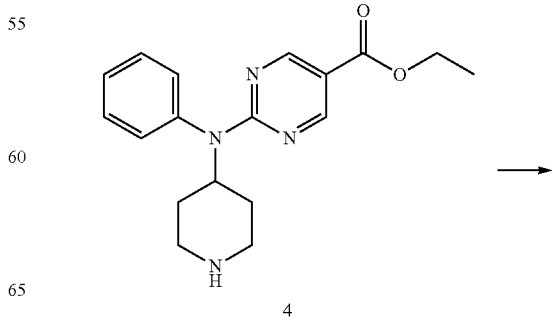

4

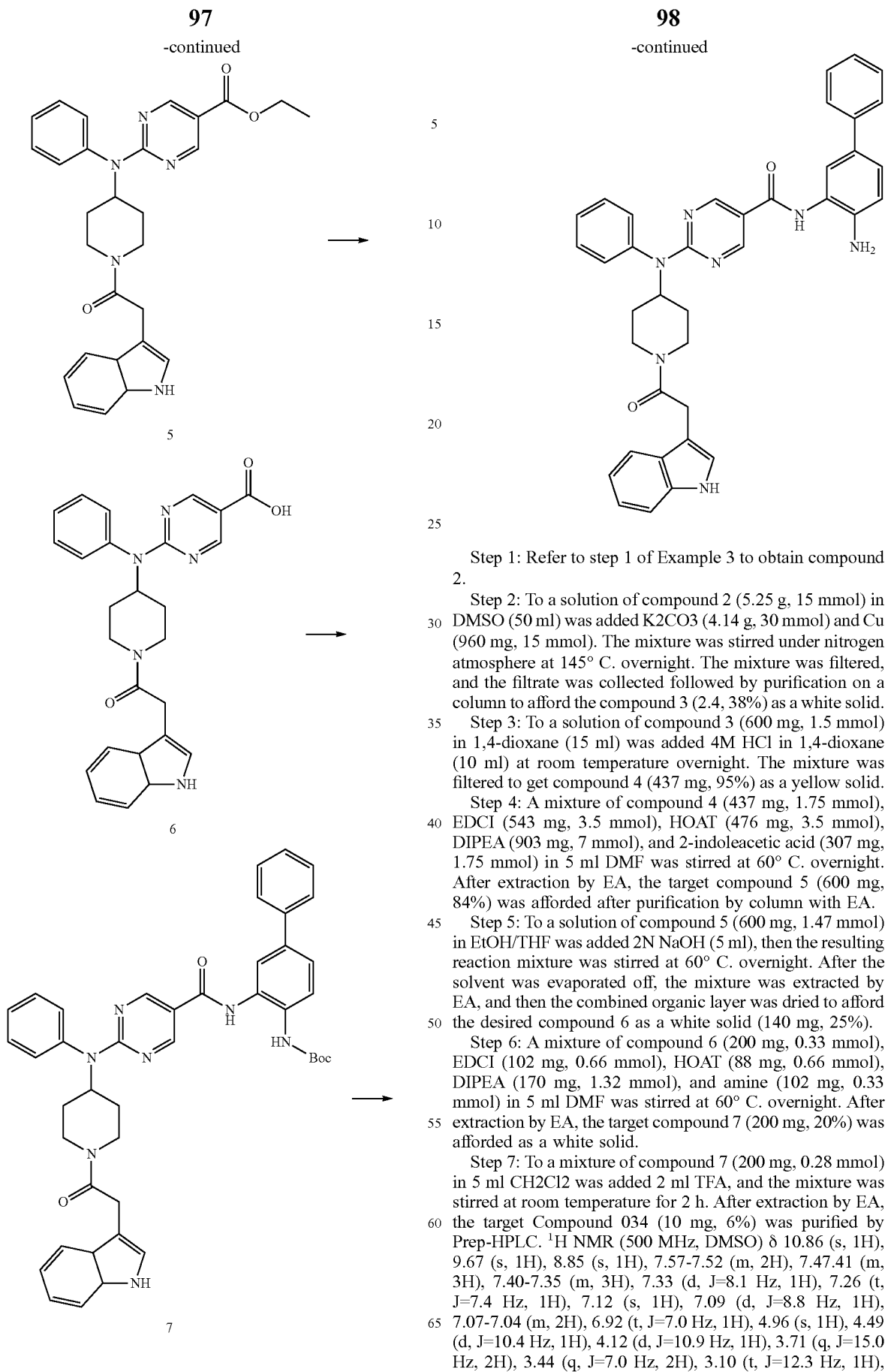

Step 1: Refer to step 1 of Example 3 to obtain compound 2.

Step 2: To a solution of compound 2 (5.25 g, 15 mmol) in DMSO (50 ml) was added K2CO3 (4.14 g, 30 mmol) and Cu (960 mg, 15 mmol). The mixture was stirred under nitrogen atmosphere at 145° C. overnight. The mixture was filtered, and the filtrate was collected followed by purification on a column to afford the compound 3 (2.4, 38%) as a white solid.

Step 3: To a solution of compound 3 (600 mg, 1.5 mmol) in 1,4-dioxane (15 ml) was added 4M HCl in 1,4-dioxane (10 ml) at room temperature overnight. The mixture was filtered to get compound 4 (437 mg, 95%) as a yellow solid.

Step 4: A mixture of compound 4 (437 mg, 1.75 mmol), EDCI (543 mg, 3.5 mmol), HOAT (476 mg, 3.5 mmol), DIPEA (903 mg, 7 mmol), and 2-indoleacetic acid (307 mg, 1.75 mmol) in 5 ml DMF was stirred at 60° C. overnight. After extraction by EA, the target compound 5 (600 mg, 84%) was afforded after purification by column with EA.

Step 5: To a solution of compound 5 (600 mg, 1.47 mmol) in EtOH/THF was added 2N NaOH (5 ml), then the resulting reaction mixture was stirred at 60° C. overnight. After the solvent was evaporated off, the mixture was extracted by EA, and then the combined organic layer was dried to afford the desired compound 6 as a white solid (140 mg, 25%).

Step 6: A mixture of compound 6 (200 mg, 0.33 mmol), EDCI (102 mg, 0.66 mmol), HOAT (88 mg, 0.66 mmol), DIPEA (170 mg, 1.32 mmol), and amine (102 mg, 0.33 mmol) in 5 ml DMF was stirred at 60° C. overnight. After extraction by EA, the target compound 7 (200 mg, 20%) was afforded as a white solid.

Step 7: To a mixture of compound 7 (200 mg, 0.28 mmol) in 5 ml CH2Cl2 was added 2 ml TFA, and the mixture was stirred at room temperature for 2 h. After extraction by EA, the target Compound 034 (10 mg, 6%) was purified by Prep-HPLC. $^1$H NMR (500 MHz, DMSO) δ 10.86 (s, 1H), 9.67 (s, 1H), 8.85 (s, 1H), 7.57-7.52 (m, 2H), 7.47.41 (m, 3H), 7.40-7.35 (m, 3H), 7.33 (d, J=8.1 Hz, 1H), 7.26 (t, J=7.4 Hz, 1H), 7.12 (s, 1H), 7.09 (d, J=8.8 Hz, 1H), 7.07-7.04 (m, 2H), 6.92 (t, J=7.0 Hz, 1H), 4.96 (s, 1H), 4.49 (d, J=10.4 Hz, 1H), 4.12 (d, J=10.9 Hz, 1H), 3.71 (q, J=15.0 Hz, 2H), 3.44 (q, J=7.0 Hz, 2H), 3.10 (t, J=12.3 Hz, 1H), 2.64 (t, J=12.2 Hz, 1H), 2.09 (s, 2H), 1.87 (dd, J=26.7, 12.8 Hz, 2H), 1.16-1.08 (m, 1H), 1.05 (t, J=7.0 Hz, 3H). LCMS: m/z=622 (M+H)⁺.
Example 35
Synthesis of Compound 035
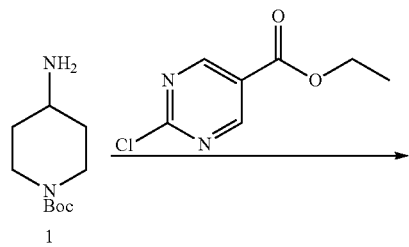
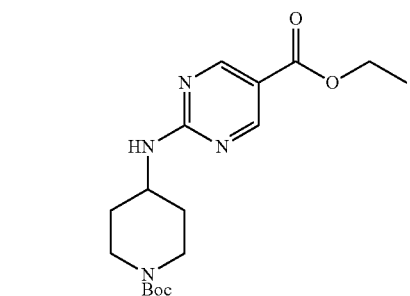
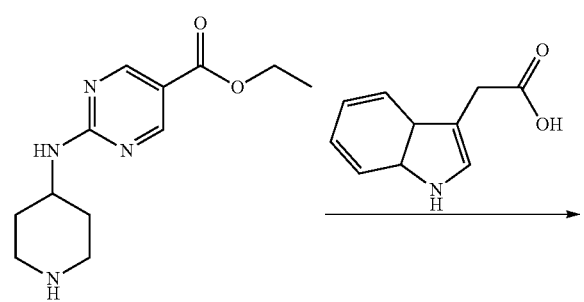
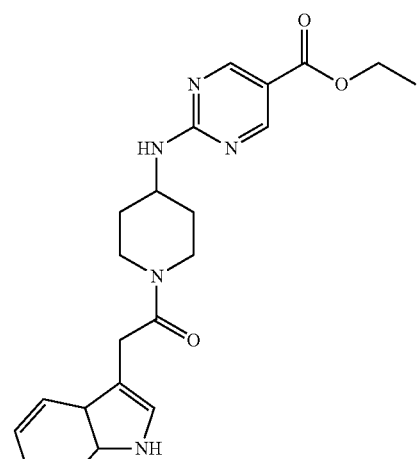
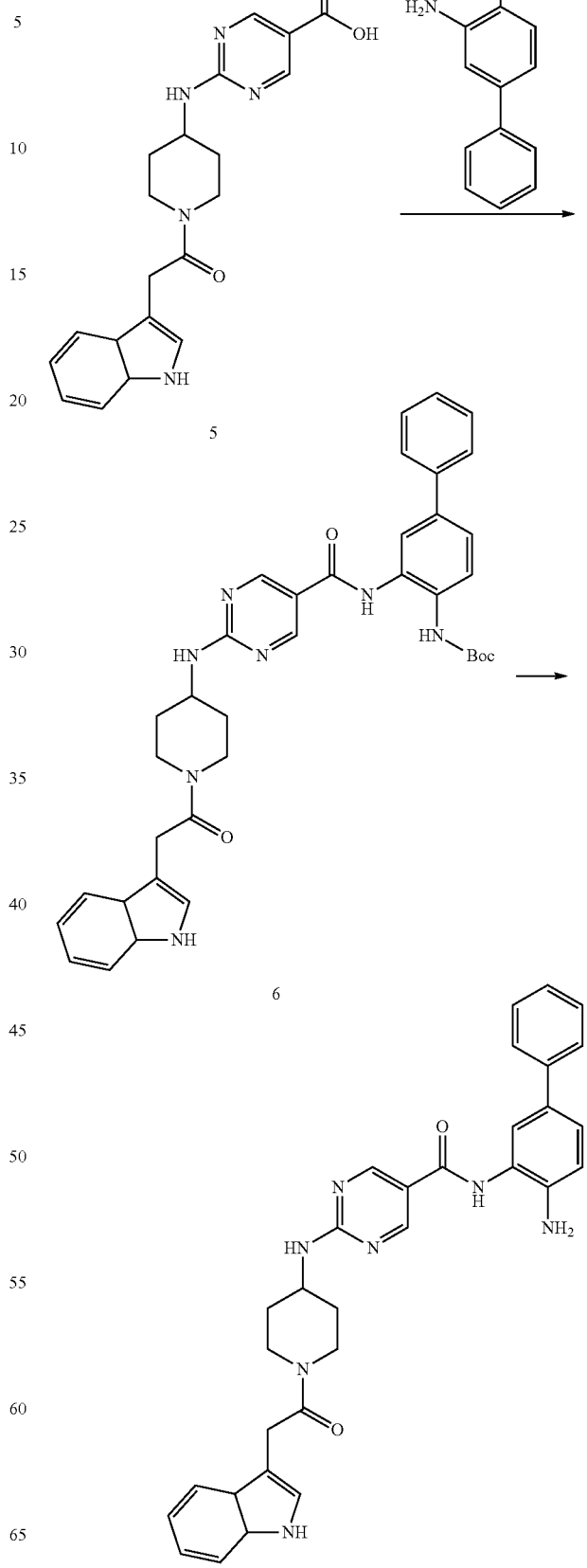

Step 1: A mixture of ethyl 2-chloropyrimidine-5-carboxylate (1.86 g, 10 mmol), compound 1 (3.00, 15 mmol), and NEt3 (3.0 g, 30 mmol) in 1,4-dioxane (20 ml) was stirred at 95° C. overnight. The mixture was concentrated, and EA (60 ml) and aqueous citric acid (60 ml) were added. The resulting reaction mixture was stirred for 30 min. The organic layer was separated, dried and concentrated to afford compound 2 (3.4 g, yield: 97%) as a light yellow solid.

Step 2: To a solution of compound 2 (600 mg, 1.7 mmol) in 1,4-dioxane (15 ml) was added 4M HCl in 1,4-dioxane (10 ml) at room temperature, and the resulting reaction mixture was stirred overnight. The mixture was filtered to yield compound 3 (427 mg, 100%) as a yellow solid.

Step 3: A mixture of compound 3 (427 mg, 1.7 mmol), compound 2-indoleacetic acid (301 mg, 1.7 mmol), HOAT (462 mg, 3.4 mmol), EDCI (649 mg, 3.4 mmol) and NEt3 (687 mg, 6.8 mmol) in DMF (15 ml) was stirred at 60° C. overnight. To the mixture was added EA (100 ml) and aqueous saturated NaCl (100 ml), and the resulting reaction mixture was stirred for 30 min. The organic layer was separated, washed by aqueous saturated NaCl (50 ml*2), dried and concentrated to yield a residue, which was purified by Prep-TLC to afford compound 4 (584 mg, 84%) as a yellow solid.

Step 4: To a solution of compound 4 (500 mg, 1.2 mmol) in EtOH (15 ml) and THF (15 ml) was added aqueous NaOH (2M, 15 mL), and the resulting reaction mixture was stirred at 60° C. for 2 h. The mixture was concentrated to afford a residue. To the mixture was added water (100 mL) and aqueous citric acid to adjust to pH<7 at 0° C. followed by filtration to yield compound 5 (342 mg, 75%) as a white solid.

Step 5: A mixture of compound 5 (150 mg, 0.39 mmol), compound Boc-amine (113 mg, 0.39 mmol), HOAT (103 mg, 0.76 mmol), EDCI (145 mg, 0.76 mmol) and NEt3 (154 mg, 1.52 mmol) in DMF (5 ml) was stirred at 60° C. overnight. To the mixture was added EA (100 ml) and aqueous saturated NaCl (100 ml), and the resulting reaction mixture was stirred for 30 min. The organic layer was separated, washed by aqueous saturated NaCl (50 ml*2), dried and concentrated to yield a residue, which was purified by Prep-TLC to afford compound 6 (150 mg, 59%) as a yellow solid.

Step 6: To a solution of compound 6 (150 mg, 0.23 mmol) in DCM (5 ml) was added TFA (3 ml) at room temperature, and the resulting reaction mixture was stirred for 2 h. The mixture was concentrated and purified by Prep-HPLC to afford Compound 035 (2 mg, 1.5%) as a white solid. $^1$H NMR (400 MHz, DMSO) δ 10.92 (s, 1H), 9.57 (s, 1H), 8.86 (s, 2H), 7.84 (d, J=7.8 Hz, 1H), 7.56 (dd, J=12.6, 7.9 Hz, 4H), 7.49 (s, 1H), 7.36 (dt, J=17.7, 8.5 Hz, 5H), 7.27-7.19 (m, 3H), 7.07 (t, J=7.4 Hz, 1H), 6.97 (t, J=7.3 Hz, 1H), 6.84 (d, J=8.3 Hz, 1H), 5.15 (s, 2H), 4.33 (d, J=14.0 Hz, 1H), 3.78 (d, J=2.4 Hz, 2H), 3.15 (t, J=12.5 Hz, 1H), 2.77 (t, J=11.7 Hz, 1H), 1.84 (s, 2H), 1.32 (d, J=10.9 Hz, 2H). LCMS: m/z=548 (M+H)$^+$.

Example 36

Synthesis of Compound 036

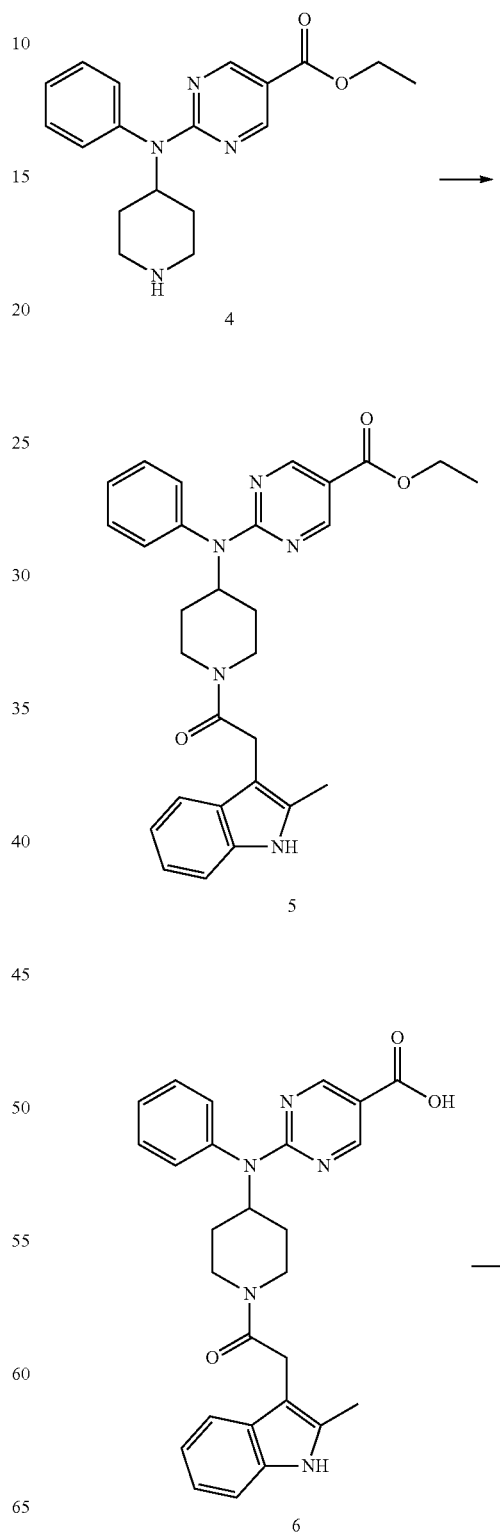

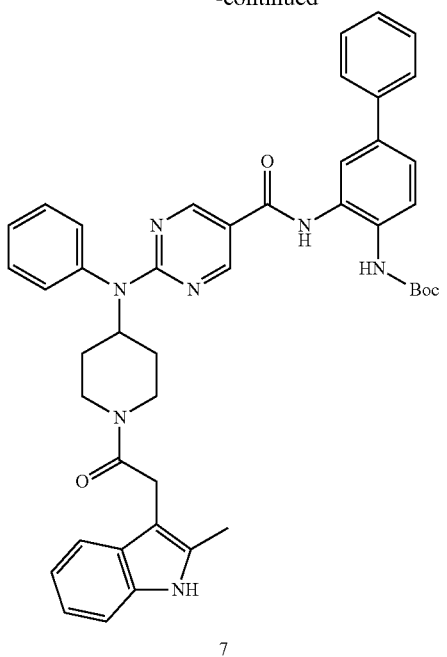

DIPEA (108 mg, 0.84 mmol), and amine (120 mg, 0.42 mmol) in 5 ml DMF was stirred at 60° C. overnight. After extraction by EA, the target compound 7 (200 mg, crude) was afforded as an oil.

Step 7: To a mixture of compound 7 (200 mg, crude) in 5 ml CH2Cl2 was added 2 ml TFA, and the mixture was stirred at room temperature for 2 h. After extraction by EA, the target Compound 036 (94 mg, 46%) was purified by Prep-HPLC. $^1$H NMR (500 MHz, DMSO) δ 10.74 (s, 1H), 9.78 (s, 1H), 8.84 (s, 2H), 7.61-7.54 (m, 3H), 7.48-7.36 (m, 6H), 7.34-7.25 (m, 2H), 7.22 (d, J=8.0 Hz, 1H), 7.04-6.94 (m, 4H), 6.86 (t, J=7.4 Hz, 1H), 4.93 (t, J=11.9 Hz, 1H), 4.48 (d, J=13.2 Hz, 1H), 3.98 (d, J=12.1 Hz, 1H), 3.64 (dd, J=45.6, 15.4 Hz, 2H), 3.07 (t, J=12.4 Hz, 1H), 2.62 (t, J=12.2 Hz, 1H), 2.22 (s, 3H), 1.85 (d, J=11.3 Hz, 1H), 1.75 (d, J=10.8 Hz, 1H), 1.08 (d, J=8.4 Hz, 1H), 0.94 (d, J=8.5 Hz, 1H). LCMS: m/z=636 (M+H)$^+$.

Example 37

Synthesis of Compound 037

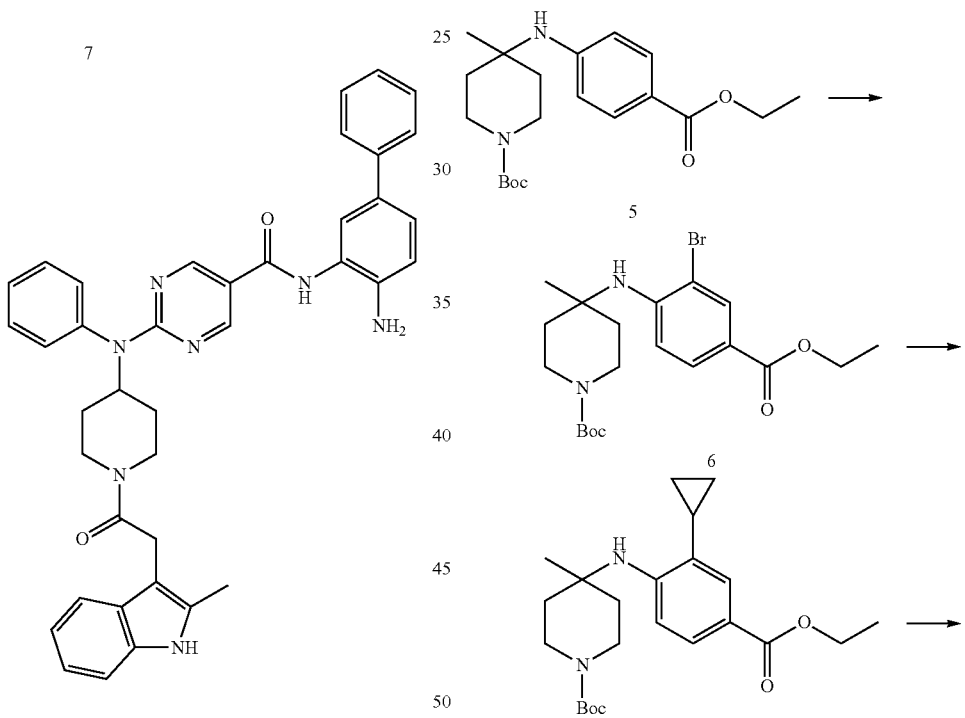

Steps 1-3: Refer to steps 1-3 of Example 34 to obtain compound 4.

Step 4: A mixture of compound 4 (500 mg, 1.53 mmol), EDCI (573 mg, 3 mmol), HOAT (405 mg, 3 mmol), DIPEA (390 mg, 3 mmol), and 2-methyl-3-indoleacetic acid (289 mg, 1.53 mmol) in 10 ml DMF was stirred at 60° C. overnight. After quenching with ice water, the target compound 5 (508 mg, 69%) was precipitated and was collected as a white solid.

Step 5: To a solution of compound 5 (508 mg, 1 mmol) in EtOH/THF (10 ml) was added 2N NaOH (5 ml), then the resulting reaction mixture was stirred at 60° C. overnight. After the solvent was evaporated off, the pH of the mixture was adjusted to 4-5. The precipitate was collected to afford the desired compound 6 as a white solid (460 mg, 96%).

Step 6: A mixture of compound 6 (200 mg, 0.42 mmol), EDCI (160 mg, 0.84 mmol), HOAT (113 mg, 0.84 mmol),

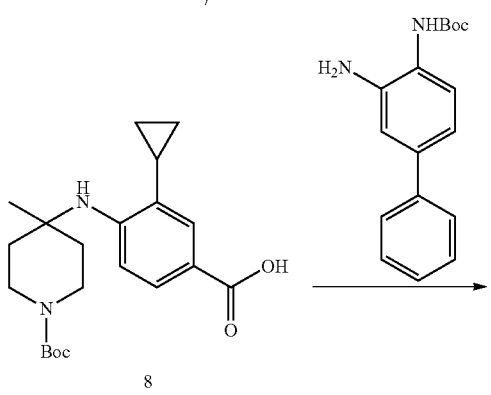

-continued

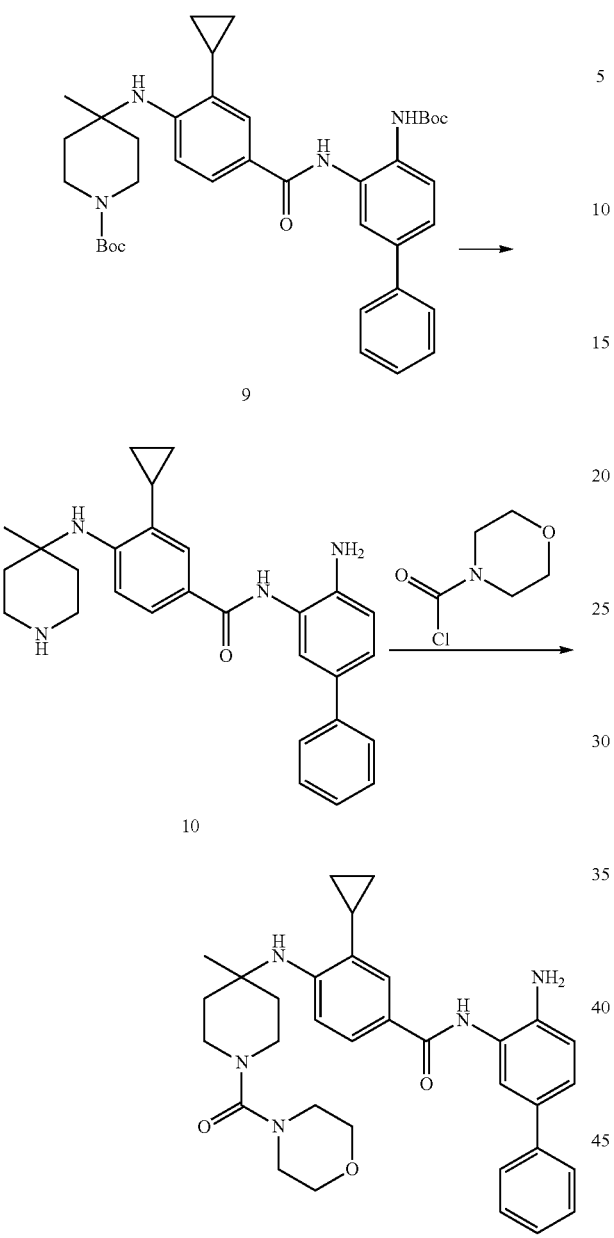

9

10

Step 1: Refer to step 1 of Example 13 to obtain compound 5.

Step 2: A mixture of compound 5 (250 mg, 0.69 mmol) and NBS (123 mg, 069 mmol in DCM (10 ml) was stirred at 0° C. for 30 min. To the mixture was added EA (20 ml) and aqueous saturated Na2SO3 (20 ml), and the resulting reaction mixture was stirred for 30 min. The organic layer was separated, washed by aqueous saturated NaCl (20 ml×2), dried and concentrated, and purified by Prep-TLC to yield compound 6 (258 mg, 85%) as a yellow solid.

Step 3: A mixture of compound 6 (240 mg, 0.55 mmol), cyclopropylboronic acid (232 mg, 2.7 mmol), Pd(OAc)2 (11 mg, 0.05 mmol), tricyclohexylphosphine (14 mg, 0.05 mmol) and K3PO4 (360 mg, 1.7 mmol) in toluene (30 ml) and H2O (5 ml) was stirred at 95° C. under nitrogen atmosphere overnight. The mixture was cooled, and to the mixture was added EA (100 ml). Filtration, concentration, and purification by silica gel column yielded compound 7 (200 mg, 90%) as a light yellow solid.

Step 4: To a solution of compound 7 (200 mg, 0.5 mmol) in EtOH (15 mL) and THF (15 ml) was added aqueous NaOH (2M, 15 mL), and the resulting reaction mixture was stirred at 60° C. for 2 h. The mixture was concentrated, and then, to the mixture, was added water (20 ml) and aqueous citric acid to adjust to pH<7 at 0° C. followed by filtration to yield compound 8 (168 mg, 90%) as a white solid.

Step 5: A mixture of compound 8 (150 mg, 0.40 mmol), compound Boc-amine (114 mg, 0.40 mmol), HOAT (103 mg, 0.76 mmol), EDCI (145 mg, 0.76 mmol) and NEt3 (154 mg, 1.52 mmol) in DMF (5 ml) was stirred at 60° C. overnight. The mixture was extracted with EA (10 ml*2), dried and concentrated, and purified by Prep-TLC to afford compound 9 (120 mg, 50%) as a yellow solid.

Step 6: To a solution of compound 9 (120 mg, 0.20 mmol) in DCM (5 ml) was added TFA (3 ml) at room temperature, and the resulting reaction mixture was stirred for 2 h. The mixture was concentrated to afford compound 10 (80 mg, 100%) and was used in the next step without further purification.

Step 7: To a solution of the compound 10 (80 mg, 0.20 mmol) and Et3N (106 mg, 1.05 mmol) in THF (5 ml) was added morpholine-4-carbonyl chloride (45 mg, 0.30 mmol) at 0° C., and the resulting reaction mixture was stirred for 2 h. To the mixture was added EA (10 ml) and aqueous saturated NaCl (10 ml), and the resulting reaction mixture was stirred for 30 min. The organic layer was separated, concentrated, and purified by Prep-HPLC to afford Compound 037 (3 mg, 3%) as a yellow solid. $^1$H NMR (400 MHz, MeOD) δ 7.78 (d, J=7.1 Hz, 2H), 7.58 (d, J=7.6 Hz, 2H), 7.48 (s, 1H), 7.39 (t, J=7.9 Hz, 3H), 7.26 (t, J=7.4 Hz, 1H), 6.99 (d, J=8.3 Hz, 1H), 6.93 (d, J=9.2 Hz, 1H), 3.71-3.66 (m, 4H), 3.50 (d, J=13.6 Hz, 2H), 3.30-3.20 (m, 6H), 2.19 (d, J=13.9 Hz, 2H), 2.05 (s, 1H), 1.84-1.67 (m, 3H), 1.53 (s, 3H), 1.33 (d, J=17.9 Hz, 1H), 1.06-0.99 (m, 2H), 0.67 (d, J=4.4 Hz, 2H). LCMS: m/z=554 (M+H)$^+$.

Example 38

Synthesis of Compound 038

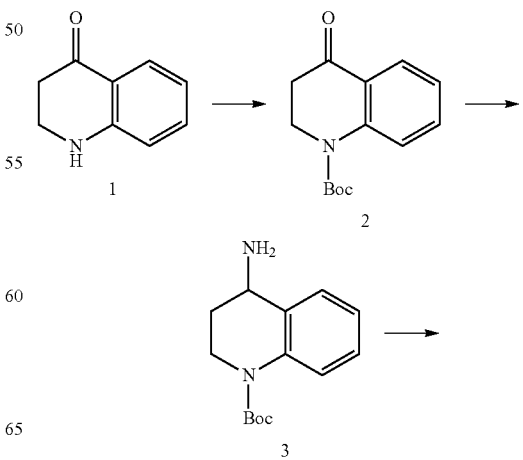

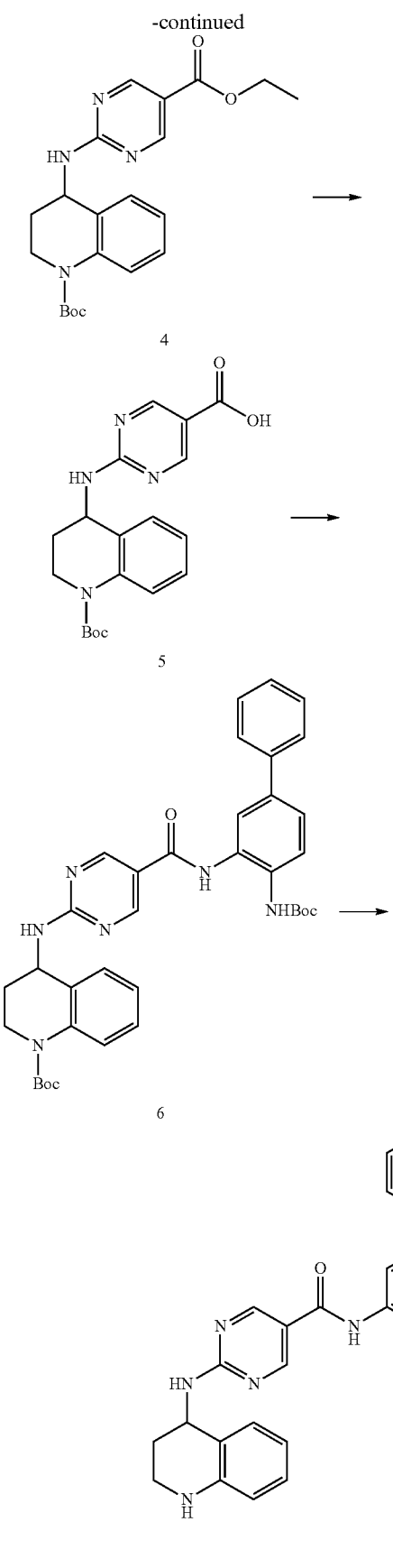

in CH2Cl2 (50 ml) was stirred at room temperature overnight. Concentration and purification by silica gel column with EA:PE=1:5 afforded compound 2 (1.5 g, 60%) as a yellow solid.

Step 2: The mixture of the compound 2 (1.4 g, 5.7 mmol), NaBH3CN (539 mg, 8.6 mmol) and ammonium acetate (3.1 g, 40.0 mmol) in MeOH (20 ml) was stirred at 70° C. for 2 hours. Concentration and purification by silica gel column with EA:PE=1:1 afforded compound 3 (1.2 g, 85%) as a yellow solid.

Step 3: S solution of the compound 3 (800 mg, 3.2 mmol), ethyl 2-chloropyrimidine-5-carboxylate (603 mg, 3.2 mmol) and DIPEA (826 mg, 6.4 mmol) in 1,4-dioxane (25 ml) was formed. The mixture was heated to 95° C. and was stirred overnight. Concentration and purification by silica gel column with EA:PE=1:10 afforded compound 4 (1.0 g, 79%) as a light yellow solid.

Step 4: A solution of the compound 4 (1.0 g, 2.5 mmol) and 2N NaOH (10 ml, 20 mmol) in THF (10 ml) and EtOH (10 ml) was formed. The mixture was heated to 60° C. and was stirred for 6 hours. Concentration and adjustment of the pH of the water phase to 5-6 was followed by extraction with EA. The organic layers were washed with water and brine then dried over sodium sulfate, filtered and concentrated to yield target compound 5 (600 mg, 65%) as a white solid.

Step 5: A mixture of the compound 5 (100 mg, 0.27 mmol), tert-butyl 3-aminobiphenyl-4-ylcarbamate (77 mg, 0.27 mmol), EDCI (53.0 mg, 0.41 mmol), HOAT (55.0 mg, 0.41 mmol) and DIEA (70 mg, 0.54 mmol) in DMF (10 ml) was formed. The mixture was heated to 65° C. and was stirred overnight. Then the mixture was dissolved in water and extracted with EA. The organic layers were washed with water and brine then dried over sodium sulfate, filtered and concentrated. Purification by silica gel column with EA:PE=1:1 yielded compound 6 (130 mg, 76%) as a purple solid.

Step 6: To a stirred solution of compound 6 (130 mg, 0.2 mmol) in CH2Cl2 (10 ml) was added HCl/1,4-dioxane (2 ml, 8.0 mmol), and the resulting reaction mixture was stirred at room temperature overnight. Concentration and washing with PE afforded the target Compound 038 (55 mg, 62%) as a white solid. $^1$H NMR (400 MHz, DMSO) δ 9.58 (s, 1H), 8.92 (s, 2H), 8.10 (d, J=8.8 Hz, 1H), 7.6-7.47 (m, 3H), 7.45-7.29 (m, 3H), 7.24 (t, J=7.3 Hz, 1H), 6.98-6.81 (m, 3H), 6.54-6.40 (m, 2H), 5.85 (s, 1H), 5.29 (s, 1H), 3.13-3.04 (m, 1H), 1.94 (d, J=5.1 Hz, 2H), 1.18 (t, J=7.2 Hz, 2H), 0.85 (s, 1H). LCMS: m/z=437 (M+H)$^+$.

Example 39

Synthesis of Compound 039

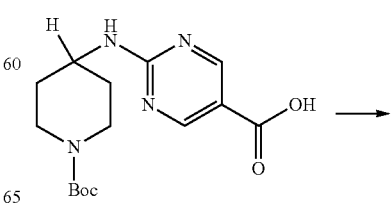

Step 1: A mixture of the compound 1 (1.5 g, 10.2 mmol), (Boc)2O (2.2 g, 10.2 mmol) and TEA (2.06 g, 20.4 mmol)

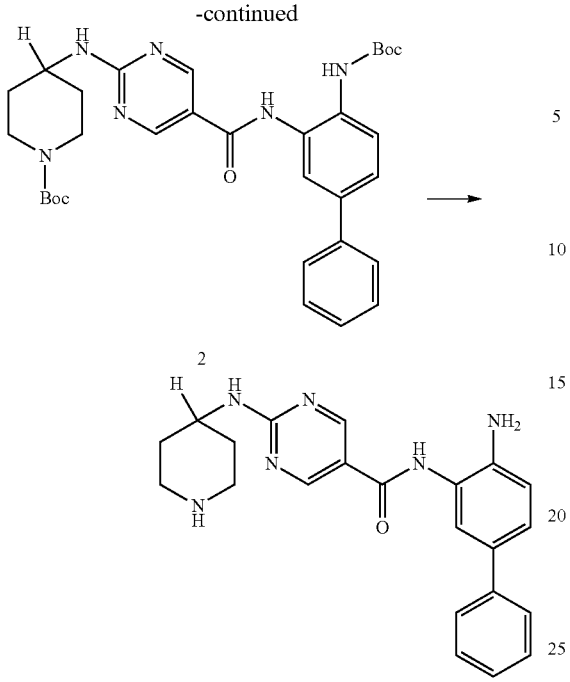

Step 1: A mixture of compound 1 (200 mg, 0.62 mmol), EDCI (192 mg, 1.24 mmol), HOAT (170 mg, 1.24 mmol), DIPEA (400 mg, 2.5 mmol), and amine (177 mg, 0.62 mmol) in 5 ml DMF was stirred at 60° C. overnight. After extraction by EA, the target compound 2 (220 mg, 59%) was afforded as a crude oil.

Step 2: To a mixture of compound 2 (220 mg, 0.4 mmol) in 5 ml CH2Cl2 was added 1 ml TFA. The mixture was stirred at room temperature for 2 h. After extraction by EA (10 ml) and water (10 ml*2), the target Compound 039 (120 mg, 67%) was purified by Prep-HPLC. $^1$H NMR (400 MHz, DMSO) δ 9.65 (s, 1H), 8.89 (s, 2H), 8.58 (s, 1H), 8.32 (s, 1H), 8.07 (d, J=7.3 Hz, 1H), 7.62-7.49 (m, 3H), 7.39 (dd, J=17.1, 9.2 Hz, 3H), 7.26 (t, J=7.4 Hz, 1H), 6.92 (s, 1H), 4.13 (s, 1H), 3.33 (d, J=12.8 Hz, 2H), 3.05 (d, J=9.9 Hz, 2H), 2.05 (d, J=11.4 Hz, 2H), 1.77-1.63 (m, 2H). LCMS: m/z=389 (M+H)$^+$.

Example 40

Synthesis of Compound 040

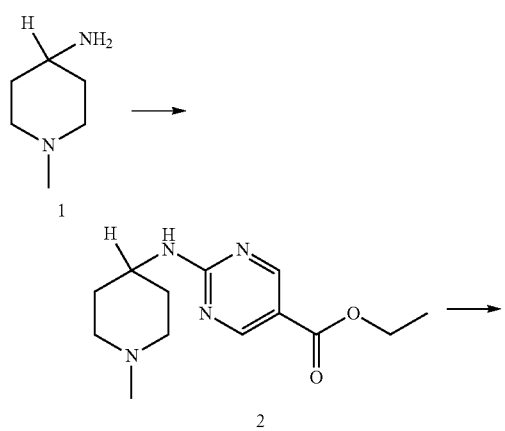

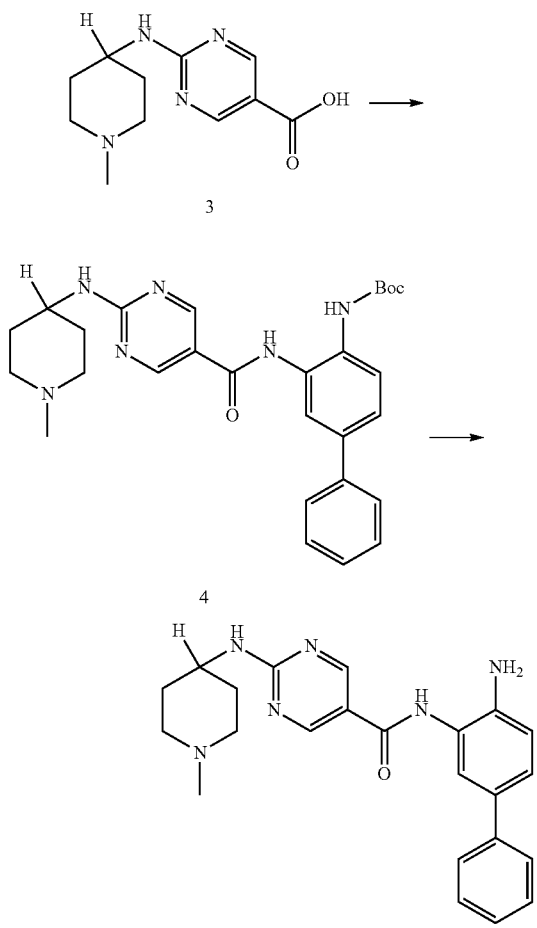

Step 1: A mixture of compound 1 (2.0 g, 17.5 mmol), ethyl 2-chloropyrimidine-5-carboxylate (3.2 g, 17.5 mmol), and DIPEA (4.5 mg, 35.0 mmol) in 5 ml CH2Cl2 was stirred at room temperature for 2 h. After extraction by EA (2*50 ml), the combined organic layer was dried to afford the target compound 2 (2.0 g, 43%) as a white solid.

Step 2: A solution of compound 2 (400 mg, 1.5 mmol) in 6M HCl was stirred at 100° C. overnight, and the desired compound 3 was dried by freeze dryer (300 mg, 85%).

Step 3: A mixture of compound 3 (150 mg, 0.63 mmol), EDCI (197 mg, 1.26 mmol), HOAT (171 mg, 1.26 mmol), DIPEA (325 mg, 2.5 mmol), and amine (179 mg, 0.63 mmol) in 5 ml DMF was stirred at 60° C. overnight. After extraction by EA, the target compound (200 mg, 63%) was purified by column with CH2Cl2:CH3OH (10:1).

Step 4: To a mixture of compound 4 (100 mg, 0.2 mmol) in 5 ml CH2Cl2 was added TFA (1 ml). The mixture was stirred at room temperature for 2 h. After extraction by EA (10 ml) and water (10 ml*2), the target Compound 040 (20 mg, 25%) was purified by Prep-HPLC. $^1$H NMR (400 MHz, DMSO) δ 9.52 (s, 1H), 8.84 (s, 2H), 7.78 (d, J=7.5 Hz, 1H), 7.59-7.46 (m, 3H), 7.39 (t, J=7.5 Hz, 2H), 7.32 (d, J=7.5 Hz, 1H), 7.24 (t, J=7.0 Hz, 1H), 6.85 (d, J=8.3 Hz, 1H), 5.14 (s, 2H), 3.77 (s, 1H), 2.75 (d, J=11.5 Hz, 2H), 2.16 (s, 3H), 1.95 (t, J=10.9 Hz, 2H), 1.83 (d, J=10.4 Hz, 2H), 1.55 (d, J=9.5 Hz, 2H). LCMS: m/z=403 (M+H)$^+$.

111
Example 41
Synthesis of Compound 041

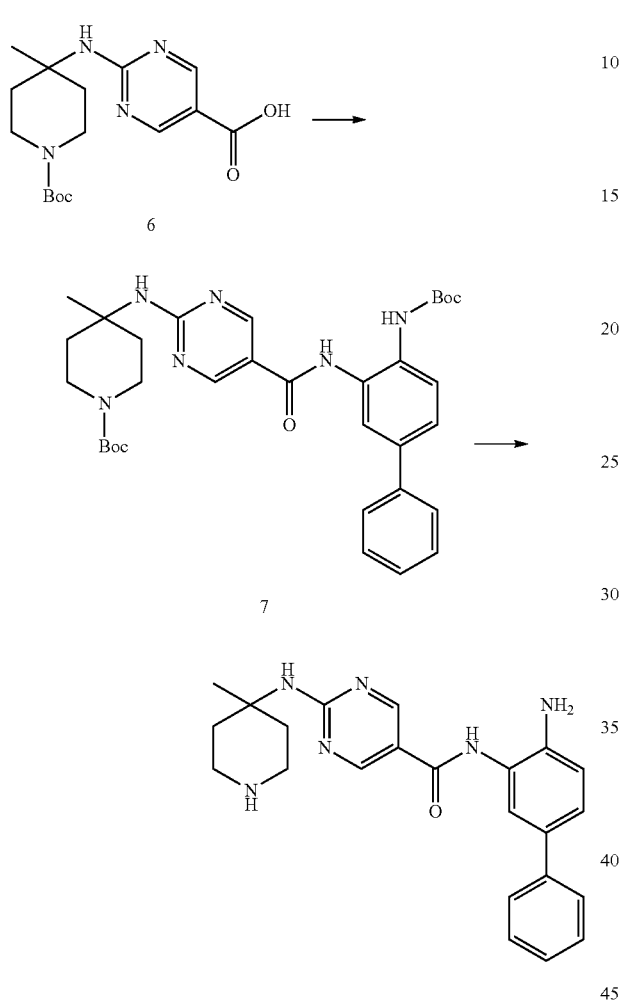

Steps 1-5: Refer to steps 1-5 of Example 7 to obtain compound 6.

Step 6: A mixture of compound 6 (200 mg, 0.62 mmol), EDCI (192 mg, 1.24 mmol), HOAT (170 mg, 1.24 mmol), DIPEA (400 mg, 2.5 mmol), and amine (177 mg, 0.62 mmol) in 5 ml DMF was stirred at 60° C. overnight. After extracted by EA, the target compound 7 (187 mg, 50%) was afforded as a crude oil.

Step 7: To a mixture of compound 7 (186 mg, 0.31 mmol) in 5 ml CH2Cl2 was added 1 ml TFA. The mixture was stirred at room temperature for 2 h. After extraction by EA (10 ml) and water (10 ml*2), the target Compound 041 (90 mg, 70%) was purified by Prep-HPLC. $^1$H NMR (400 MHz, DMSO) δ 9.57 (s, 1H), 8.88 (s, 2H), 7.63 (s, 1H), 7.54 (d, J=7.4 Hz, 2H), 7.49 (s, 1H), 7.39 (t, J=7.7 Hz, 2H), 7.35-7.29 (m, 1H), 7.24 (t, J=7.3 Hz, 1H), 6.85 (d, J=8.4 Hz, 1H), 5.16 (s, 2H), 3.04 (d, J=13.0 Hz, 2H), 2.96 (t, J=10.8 Hz, 2H), 2.43 (s, 2H), 1.68 (t, J=10.7 Hz, 2H), 1.44 (s, 3H). LCMS: m/z=402 (M+H)$^+$.

112
Example 42
Synthesis of Compound 042

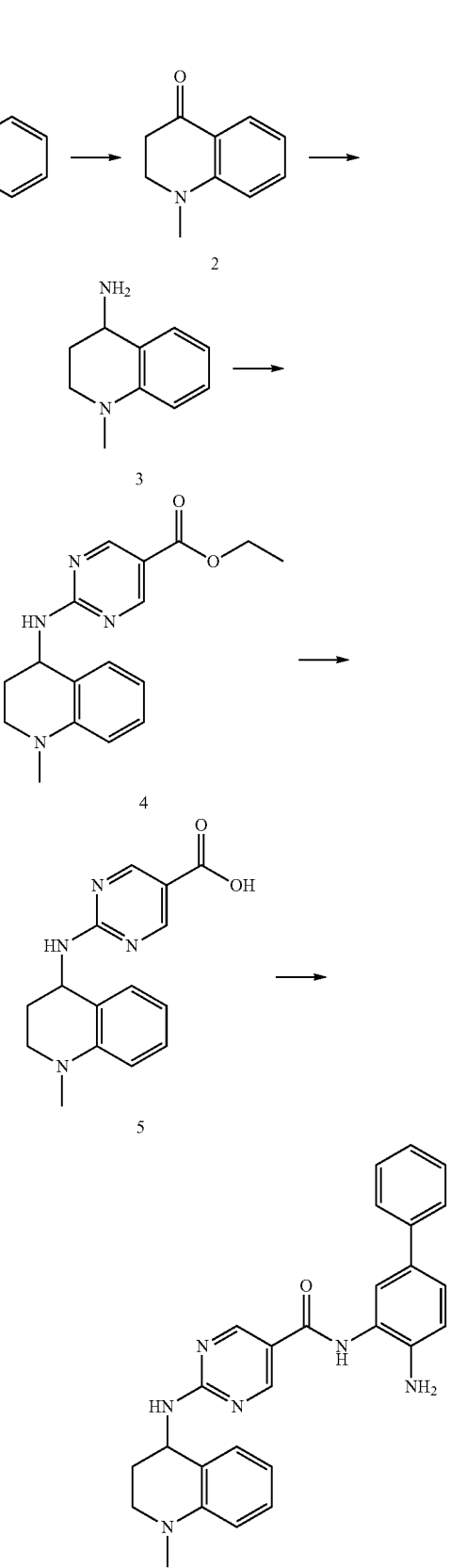

Step 1: A mixture of compound 1 (2.0 g, 13.6 mmol), iodomethane (5.8 g, 40.8 mmol), and K2CO3 (5.5 g, 40.8 mmol) in DMF (30 ml) was stirred at 80° C. overnight. To the mixture was added EA (100 ml) and aqueous saturated NaCl (100 ml), and the resulting reaction mixture was stirred for 30 min. The organic layer was separated, washed by aqueous saturated NaCl (50 ml*2), dried and concentrated, purified by silica gel column to afford compound 2 (1.5 g, 68%) as a yellow solid.

Step 2: A mixture of compound 2 (1.5 g, 9.3 mmol), NaBH3CN (1.8 g, 27.9 mmol), and AcONH4 (3.6 g, 46.5 mmol) in MeOH (30 ml) was stirred at 70° C. for 5 h. To the mixture was added EA (100 ml) and aqueous saturated NaCl (100 ml), and the resulting reaction mixture was stirred for 30 min. The organic layer was separated, washed by aqueous saturated NaCl (50 ml*2), dried and concentrated to afford compound 3 (1.4 g, 80%) as a white solid.

Step 3: A mixture of compound 3 (1.6 g, 10 mmol), ethyl 2-chloropyrimidine-5-carboxylate (1.7 g, 9 mmol), and DIPEA (3.9 g, 30 mmol) in DCM (30 ml) was stirred at room temperature overnight. The mixture was purified by silica gel column to afford compound 4 (800 mg, 29%) as a yellow solid.

Step 4: To a solution of compound 4 (800 mg, 2.6 mmol) in EtOH (20 ml) and THF (20 ml) was added aqueous NaOH (2M, 20 ml). The mixture was stirred at 60° C. for 2 h. The mixture was concentrated to yield a residue, and, to the mixture, was added water (100 ml) and aqueous citric acid to adjust to pH<7 at 0° C. followed by filtration to afford compound 5 (600 mg, 80%) as a white solid.

Step 5: A mixture of compound 5 (150 mg, 0.53 mmol), compound Boc-amine (152 mg, 0.53 mmol), HOAT (103 mg, 0.76 mmol), EDCI (145 mg, 0.76 mmol) and NEt3 (154 mg, 1.52 mmol) in DMF (5 mL) was stirred at 60° C. overnight. The mixture was extracted by EA (10 ml) and water (10 ml*2). The organic layer was separated, washed by aqueous saturated NaCl (20 ml*2), dried and concentrated, and purified by Prep-TLC to afford compound 6 (45 mg, 15%) as a yellow solid.

Step 6: To a solution of compound 6 (45 mg, 0.08 mmol) in 1,4-dioxane (5 ml) was added HCl in 1,4-dioxane (0.5 ml) at room temperature, and the resulting reaction mixture was stirred overnight. The mixture was filtered to afford Compound 042 (15 mg, 41%). $^1$H NMR (500 MHz, DMSO) δ 10.43 (s, 1H), 9.00 (d, J=29.0 Hz, 2H), 8.30 (d, J=8.6 Hz, 1H), 7.80 (d, J=1.9 Hz, 1H), 7.67 (d, J=7.4 Hz, 2H), 7.61 (dd, J=8.3, 1.9 Hz, 1H), 7.49 (t, J=7.7 Hz, 2H), 7.45-7.37 (m, 2H), 7.12 (t, J=7.8 Hz, 1H), 7.04 (d, J=7.3 Hz, 1H), 6.72 (d, J=8.2 Hz, 1H), 6.63 (t, J=7.3 Hz, 1H), 5.32 (d, J=6.8 Hz, 1H), 3.39 (s, 2H), 2.90 (s, 3H), 2.07 (dd, J=22.1, 4.2 Hz, 2H). LCMS: m/z=451 (M+H)$^+$.

Example 43

HDAC Enzyme Assays

Compounds for testing were diluted in DMSO to 50 fold the final concentration and a ten point three fold dilution series was made. The compounds were diluted in assay buffer (50 mM HEPES, pH 7.4, 100 mM KCl, 0.001% Tween-20, 0.05% BSA, 20 µM tris(2-carboxyethyl)phosphine) to 6 fold their final concentration. The HDAC enzymes (purchased from BPS Biosciences) were diluted to 1.5 fold their final concentration in assay buffer and pre-incubated with the compounds for 24 hours prior to addition of the substrate.

Figure 4:
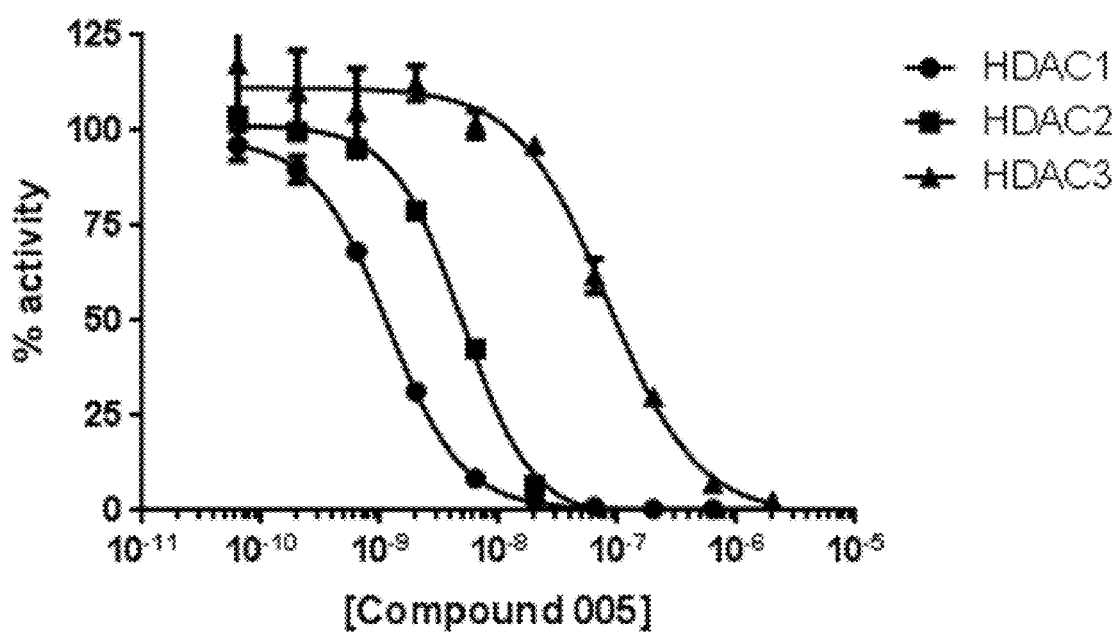
FIG. 4 is a graph showing the HDAC inhibition profile of Compound 005 with respect to HDAC1, HDAC2, and HDAC3 (See, Example 43).

The substrate tripeptide substrate 3 (synthesized in house) for each enzyme was equal to the Km as determined by a substrate titration curve. The enzyme and substrate concentrations used are given in Table 2. The substrates were diluted in assay buffer at 6× their final concentration with 0.3 µM sequencing grade trypsin (Sigma). The substrate/trypsin mix was added to the enzyme/compound mix, the plate was shaken for 60 seconds and placed into a Spectramax M5 microtiter plate reader. The development of fluorescence was monitored for 30 min and the linear rate of the reaction was calculated. The $IC_{50}$ was determined using Graph Pad Prism by a four parameter curve fit. The $IC_{50}$ values obtained for the compounds of this invention are found in Table 1. Examples of the curves are found in FIGS. 1 and 4.

TABLE 2

| | Enzyme concentration | Substrate concentration |
|---|---|---|
| HDAC1 | 3.5 ng/µl | 3.8 µM |
| HDAC2 | 0.2 ng/µl | 2.3 µM |
| HDAC3 | 0.08 ng/µl | 3.9 µM |

Example 44

Pharmacokinetics

Male SD rats were fasted overnight. Compounds of the invention were dissolved in dimethyl acetamide at 10 times the final concentration, then Solutol HS 15 (BASF) was added to a final concentration of 10%. Finally 80% saline was added and vortexed to achieve a clear solution. For the IV dosing three animals were injected via the foot dorsal vein with 1 mg/kg compound. For the PO dosing 5 mg/kg of compound was delivered by oral gavage. Blood was collected via the tail vein into K2EDTA tubes at 5 minutes, 15 minutes, 30 minutes, 1 hour, 2 hours, 4 hours, 8 hours and 24 hours after dosing. The blood was centrifuged at 2000 g for 5 minutes at 4° C. to obtain plasma. The plasma was extracted with acetonitrile and the level of compound was analyzed by LC/MS/MS. The level of compound in plasma was calculated from a standard curve in rat plasma. The IV clearance and area under the curve were calculated using WinNonLin software. The dose adjusted area under the curve for the IV and oral dosing were used to calculate the oral bioavailability.

Figure 2:
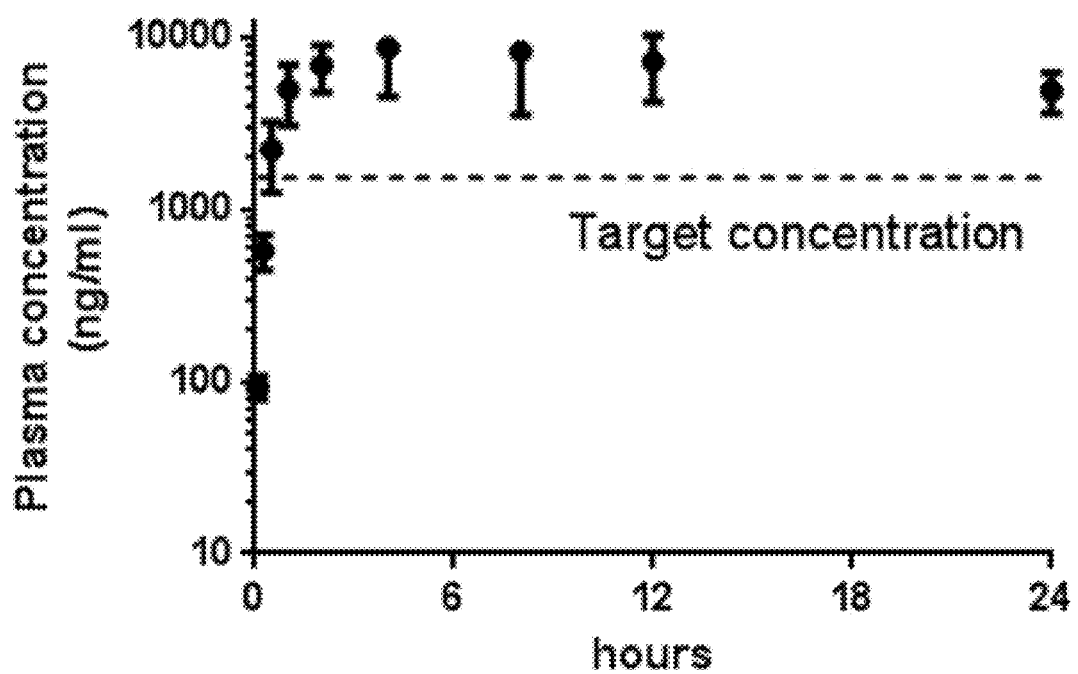
FIG. 2 shows the plasma concentration in a rat as a function of time upon oral administration of 40 mg/kg of Compound 003 (See Example 44).

A summary of results is presented in Table 3 and Table 4, as well as FIG. 2.

Figure 5:
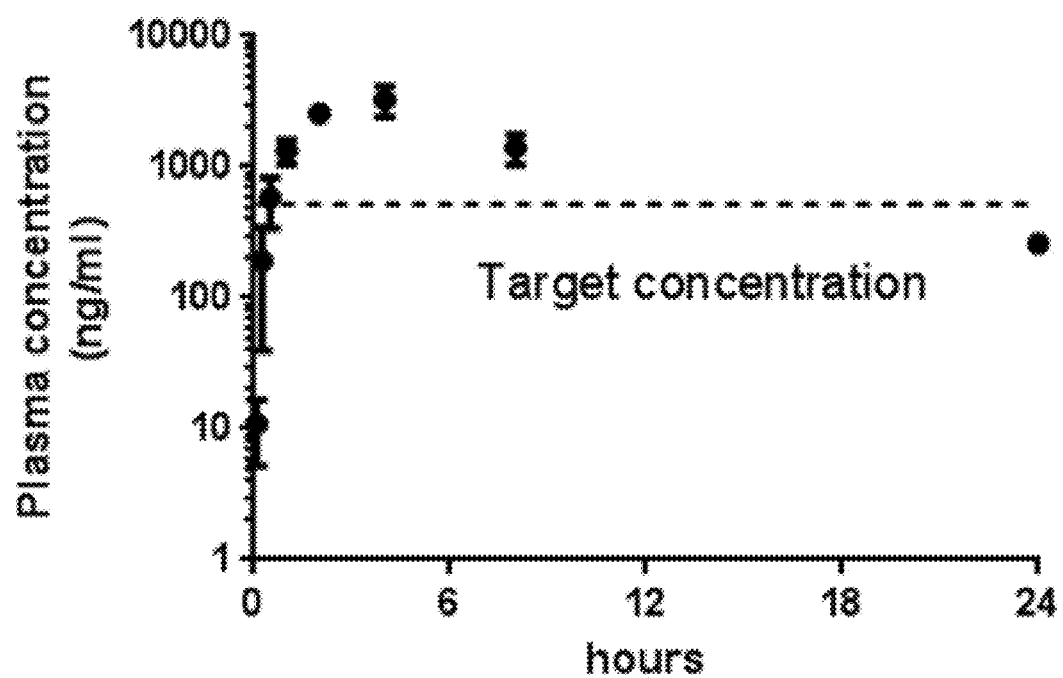
FIG. 5 shows the plasma concentration in a rat as a function of time upon oral administration of 20 mg/kg of Compound 005 (See Example 44).

Cynomolgus monkey pharmacokinetics was determined for Compound 005. Compound 005 was dissolved in 0.5% hydroxypropyl methyl cellulose and given to fed cynomolgus monkeys at 20 mg/kg body weight. Plasma samples were collected over time and analyzed as described above. Plasma levels at each time point are shown in FIG. 5.

TABLE 3

| | Cell based | Cassette Rat PK (5 mg/kg PO) | | | | |
|---|---|---|---|---|---|---|
| Compound | assay potency | IV Clr. | PO $C_{max}$ | PO T½ | PO AUC | F % |
| Compound 003 | 3 µM | 0.12 | 2316 | 17 | 59876 | 118 |
| Compound 001 | 3 µM | 0.53 | 988 | 3.8 | 5959 | 63 |

TABLE 3-continued

| | Cell based | Cassette Rat PK (5 mg/kg PO) | | | | |
|---|---|---|---|---|---|---|
| Compound | assay potency | IV Clr. | PO $C_{max}$ | PO T½ | PO AUC | F % |
| Compound 002 | 3 µM | 1.2 | 1011 | 5.9 | 6091 | 142 |
| Compound 005 | 1 µM | 0.38 | 569 | >24 | 9162 | 79 |
| Compound 004 | ND | 0.57 | 1497 | 7.6 | 15941 | 209 |
| Compound 006 | ND | 0.15 | 1517 | 14.5 | 31640 | 76 |

Table 3: Compounds were tested in the fetal globin induction assay and the lowest concentration to achieve a 2 fold increase in fetal globin gene expression over baseline is presented in the "Cell based assay potency" column. Pharmacokinetic properties were assessed in a rat cassette dosing experiment. The IV clearance (IV Clr.) is in units of L/hr/kg. The oral maximum plasma concentration (PO Cmax) is in units of ng/ml. The oral plasma half life (PO T½) is in units of hours. The oral area under the curve (PO AUC) is in units of hours*ng/ml. The fraction absorbed by the oral route (F %) is a percentage of the oral area under the curve to the IV area under the curve, dose adjusted.

TABLE 4

| | In vitro tox | | | | In vitro ADME (Absorption, Distribution, Metabolism, and Excretion) | | | |
|---|---|---|---|---|---|---|---|---|
| Compound | hERG | Cyp | Ames | MN | Solubility | Plasma stability | Protein binding | Microsome stability |
| Comp. 003 | >30 µM | >10 µM | Neg | Neg | 54 µM | ND | ND | 4.7 min |
| Comp. 001 | >30 µM | 2C9 | ND | ND | 16.9 µM | ND | ND | 11 min |
| Comp. 002 | >30 µM | >10 µM | ND | ND | 42.7 µM | ND | ND | ND |
| Comp. 005 | 13.8 µM | >10 µM | Neg | Neg | 13.8 µM | ND | ND | ND |
| Comp. 004 | 12 µM | >10 µM | ND | ND | 12 µM | ND | ND | ND |
| Comp. 006 | >30 µM | >10 µM | ND | ND | ND | ND | ND | ND |

Example 45

Fetal Globin Induction

CD34+ cells isolated from human bone marrow were cultured in vitro using a method described by Bradner J E (*Proc Natl Acad Sci USA*. 2010 Jul. 13; 107(28):12617-22), which consists of a 7 day expansion phase in media that supports differentiation of cells towards the erythroid lineage followed by a differentiation phase for 3 days where erythroid cell development continues. At the end of the differentiation period these cells are primarily late erythroblasts. mRNA levels were determined by quantitative real time PCR using primer/probe sets designed to adult major β-globin (β), adult minor β-globin (δ), fetal β-like globin (HbG, γ), and embryonic β-like globin (ε). Protein levels were determined by flow cytometry using fluorescent antibodies against fetal hemoglobin (HbF) or adult hemoglobin (HbA).

Figure 3:
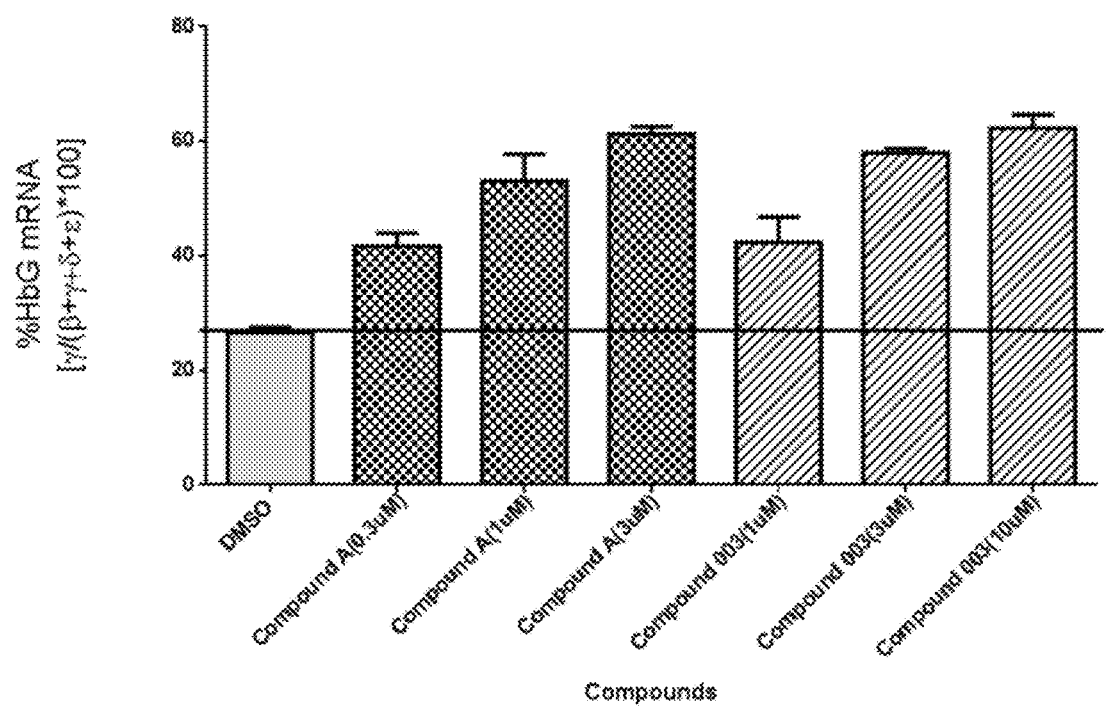
FIG. 3 shows the in vitro fetal globin induction of Compound 003 in comparison to another known HDAC1/2 inhibitor, Compound A (See Example 45).
Figure 6:
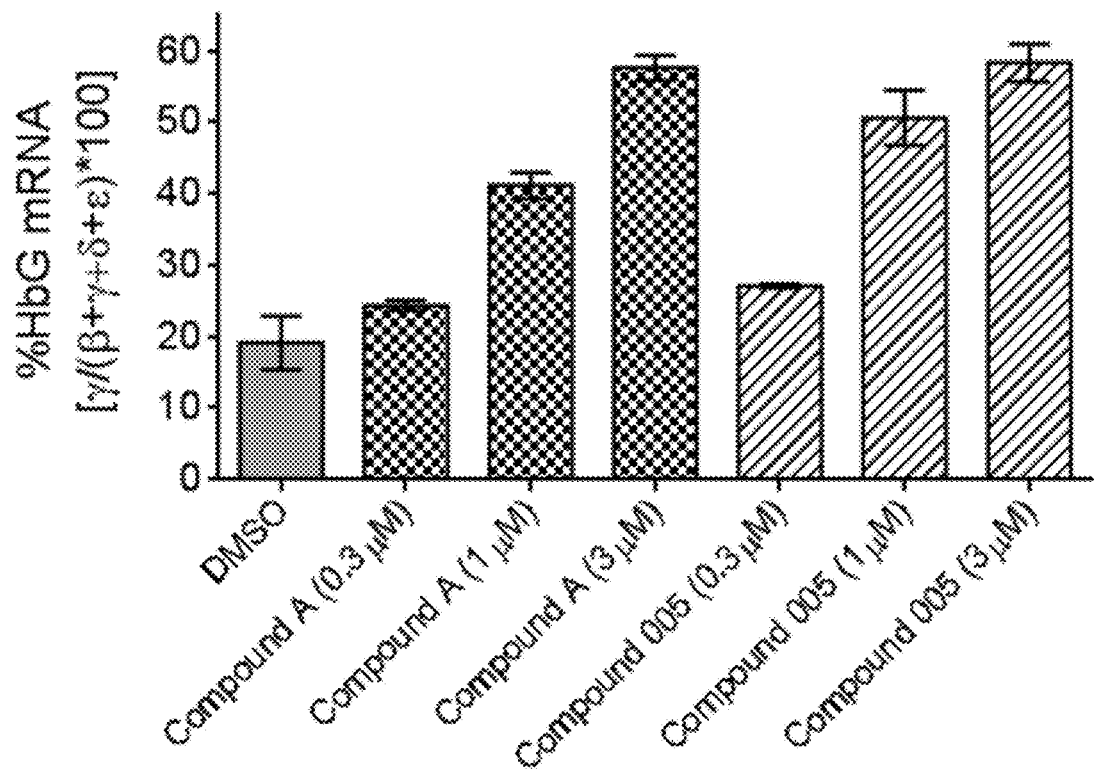
FIG. 6 shows the in vitro fetal globin induction of Compound 005 in comparison to another known HDAC1/2 inhibitor, Compound A (See Example 45).

In the experiment shown in FIG. 3, cells were differentiated in the presence of vehicle (DMSO) 0.3, 1 and 3 µM of Compound A, and of 0.3, 1, and 3 µM of Compound 003. In the experiment shown in FIG. 6, cells were differentiated in the presence of vehicle (DMSO) 0.3, 1 and 3 µM of Compound A, and of 0.3, 1, and 3 µM of Compound 005. Globin mRNA levels were determined at day 3 of differentiation.

Compound A is an HDAC1/2 inhibitor ($IC_{50}$ is about 4, 15, and 114 nM for HDAC1, HDAC2, and HDAC3, respectively) with the structure shown below. The characterization and synthesis of Compound A is found in U.S. Publication No. 2014-0128391.

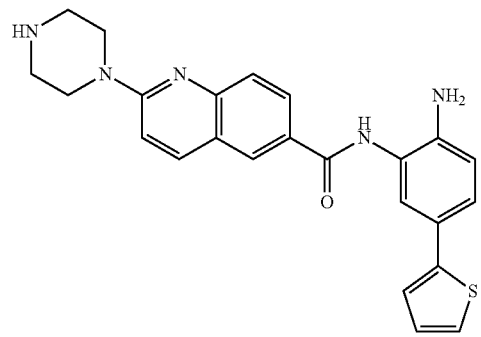

Compound A

Example 46

Additional Studies

Additional experiments were performed that show Compound 003 lacks hERG, CYP inhibition, and genotoxicity.

For hERG assays, a CHO cell line stably transfected with hERG cDNA and expressing hERG channels were seeded into a QPatch plate (Sophion) at a density of 3-8×10⁶ cells/ml. The cells were voltage clamped at a holding potential of −80 mV. The hERG current was activated by depolarizing at +20 mV for 5 sec, after which the current was taken back to −50 mV for 5 sec to remove the inactivation and observe the deactivating tail current. The maximum amount of tail current size was used to determine hERG current amplitude. Six doses (30, 10, 3, 1, 0.3 and 0.1 µM) of Compound 003 were chosen to obtain fitting curves and IC50. Data were analyzed using Assay Software provided by Sophion and Graphpad Prism. Compound 003 did not inhibit the activity of the hERG channel at the highest concentration of 30 µM.

For Cyp inhibition, human live microsomes from BD Gentest were incubated with Compound 003 (10, 3.33, 1.11, 0.37, 0.12, 0.04, 0.01 µM) and substrate (CYP1A2: Phenacetin at 30 µM; CYP2C9: Diclofenac at 10 µM; CYP2C19: S-Mephenytoin at 35 µM; CYP3A4: Midazolam at 5 µM and Testosterone at 80 µM; CYP2D6: Bufuralol at 10 µM) for the following incubation times: CYP1A2, 2C9, 2D6: 10 minutes, 37° C.; CYP2C19: 45 minutes, 37° C.; CYP3A4: 5 minutes, 37° C. Substrate conversion was measured by liquid chromatography/mass spectrometry/mass spectrometry (LC/MS/MS). Inhibition was calculated by curve fitting in Graph Pad Prism. Compound 003 did not inhibit activity of any Cyp up to 10 µM.

For genotoxicity, bacterial tester strains TA98, TA100, TA1535 and TA97a as described by Ames et al. (1975) and the *E. coli* tester strain WP2 uvrA as described by Green and Muriel (1976) were incubated with Compound 003 at 250, 75, 25, 7.5, 2.5, 0.75, 0.25, and 0.075 µg/well in 24 well plates either with or without liver homogenate (S9) purchased commercially (MolTox; Boone, N.C.) prepared from male Sprague Dawley rats that have been injected intraperitonealy with Aroclor 1254 (200 mg/mL in corn oil), at a dose of 500 mg/kg, 5 days before sacrifice. Mutagenicity is evaluated by counting the number of colonies that form on non-permissive media. Compound 003 did not increase the number of revertant colonies of any strain either with or without S9 activation.

Genotoxicity was further evaluated by micronucleus formation assay in human peripheral blood lymphocytes (HPBL). HPBL were obtained from healthy donors and exposed to Compound 003 at 3500, 2450, 1715, 1200, 840, 588, 412, 288, 202, 141, 98.8, 69.2, 48.4, and 33.9 m/ml for 4 hours with or without S9 activation. The cells were washed with PBS and incubated in complete medium with 6 µg/ml cytocholasin B for 24 hours. The cells were then lysed, fixed, and mounted on microscope slides. The number of mononucleated, binucleated, and micronucleated cells was counted under blinded conditions. Compound 003 did not increase the number of micronucleated cells at any concentration.

Example 47

Figure 7:
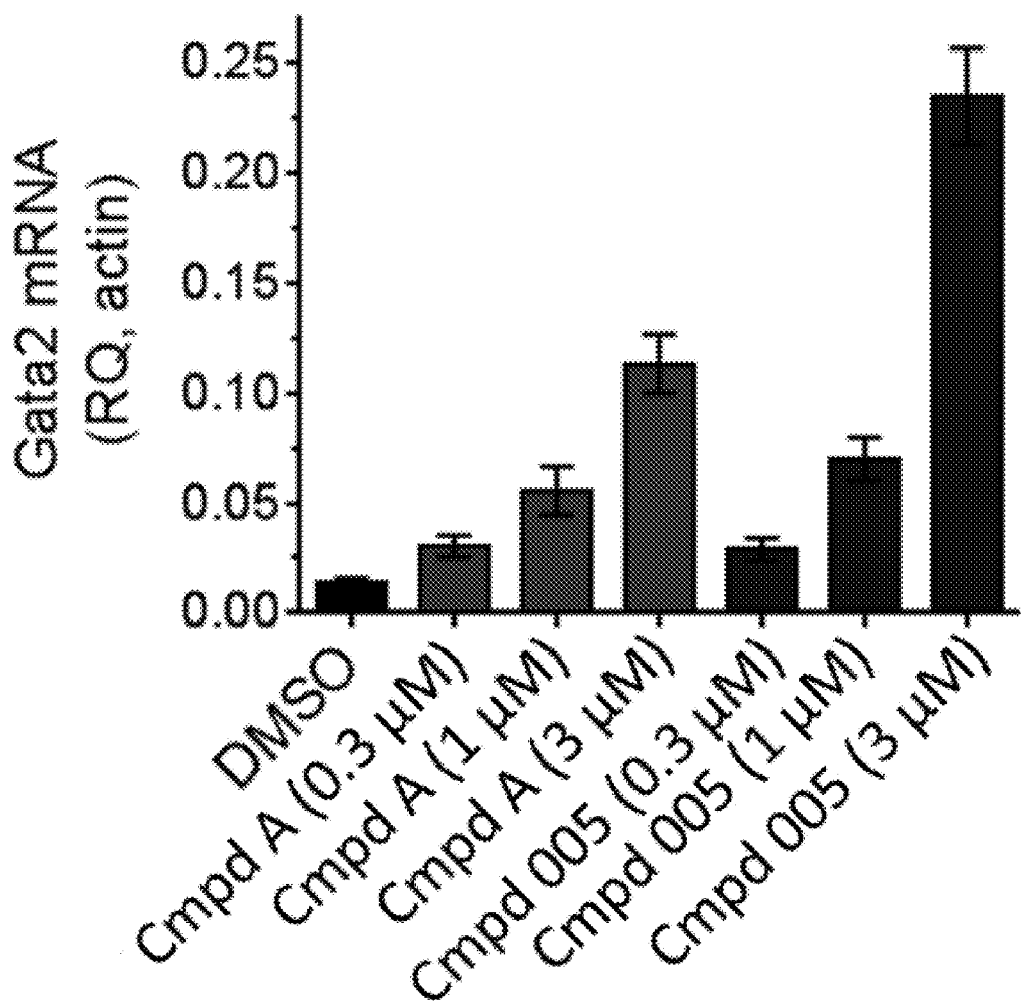
FIG. 7 shows that treatment of erythroid progenitors with various HDAC1/2 inhibitors (Compounds 005 and A) leads to induction of Gata2 mRNA.

Treatment of Erythroid Progenitors with Various HDAC1/2 Inhibitors Leads to Induction of Gata2 mRNA Human bone marrow derived CD34+ cells were expanded for 7 days as described by Sankaran et al., Science, vol. 322(5909), pp. 1839-42 (2008). Cells were then differentiated, in the presence of the indicated concentration of Compound 005, Compound A (another known HDAC1/2 inhibitor), or vehicle control (DMSO), for 3 days in media supporting erythropoiesis (Hu et al., "Isolation and functional characterization of human erythroblasts at distinct stages: implications for understanding of normal and disordered erythropoiesis in vivo", Blood, vol. 121(16), pp. 3246-53 (2005)). Gata2 mRNA was determined using quantitative real time PCR and expressed relative to the level beta-actin mRNA control. Compound 005 or Compound A treatment of primary erythroid progenitors results in an equivalent dose and time-dependent induction of % HbG (FIG. 6) and Gata2 mRNA (FIG. 7).

INCORPORATION BY REFERENCE

The contents of all references (including literature references, issued patents, published patent applications, and co-pending patent applications) cited throughout this application are hereby expressly incorporated herein in their entireties. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the invention described herein. Such equivalents are intended to be encompassed by the following claims.

We claim:
1. A compound having the structure of Formula IIIa:

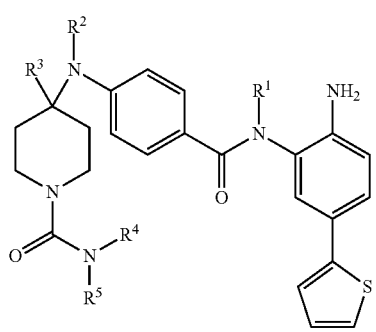

IIIa or a pharmaceutically acceptable salt thereof wherein,
$R^1$ is selected from the group consisting of H and $C_1$-$C_6$-alkyl;
$R^2$ is selected from the group consisting of H, $C_1$-$C_6$-alkyl, and $C_6$-aryl;
$R^3$ is selected from the group consisting of H, $C_1$-$C_6$-alkyl, and $C_6$-aryl;
or $R^2$ and $R^3$ together form a $C_2$-$C_6$-heterocyclyl;
$R^4$ and $R^5$ together form a heterocyclyl selected from the group consisting of morpholinyl, piperidinyl, piperazinyl, and pyrrolidinyl, wherein the morpholinyl, piperidinyl, piperazinyl, and pyrrolidinyl are optionally substituted by 1 or 2 of $C_1$-$C_6$-alkyl, halo, or hydroxy.

2. The compound of claim 1, wherein $R^1$ is H.
3. The compound of claim 1, wherein $R^2$ is H.
4. The compound of claim 1, wherein $R^3$ is H, methyl, ethyl, isopropyl, or phenyl.
5. The compound of claim 1 selected from:

| ID | Structure |
|---|---|
| 004 | 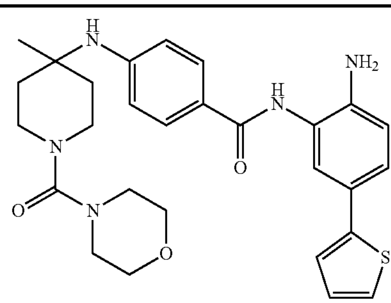 |
| 005 | 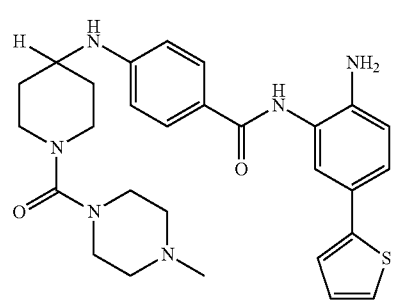 [SMILES: CN1CCN(C(=O)N2CCC(Nc3ccc(C(=O)Nc4cc(-c5cccs5)ccc4N)cc3)CC2)CC1] |

119
-continued
| ID | Structure |
|---|---|
| 006 | 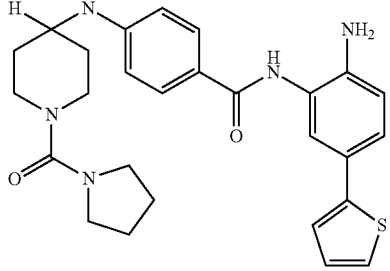 |
| 013 | 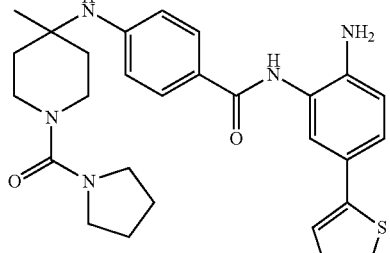 |
| 015 | 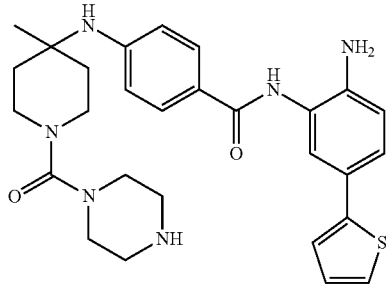 [SMILES: CC1(Nc2ccc(C(=O)Nc3cc(-c4cccs4)ccc3N)cc2)CCN(C(=O)N2CCNCC2)CC1] |
| 016 | 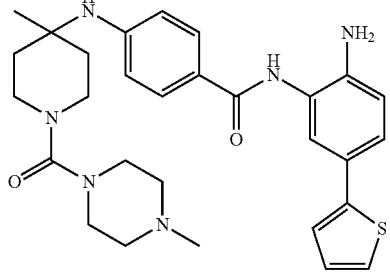 |
| 017 | 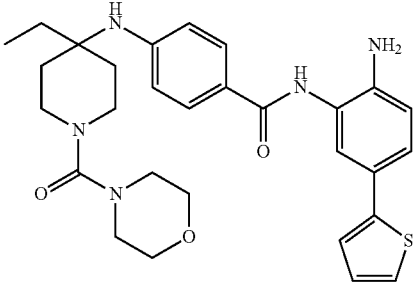 [SMILES: CCC1(Nc2ccc(C(=O)Nc3cc(-c4cccs4)ccc3N)cc2)CCN(C(=O)N2CCOCC2)CC1] |
120
-continued
| ID | Structure |
|---|---|
| 019 | 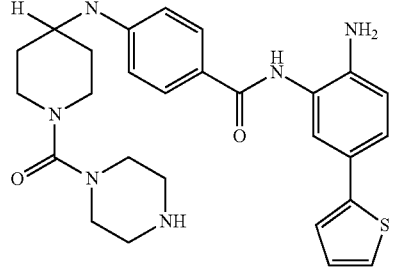 |
| 020 | 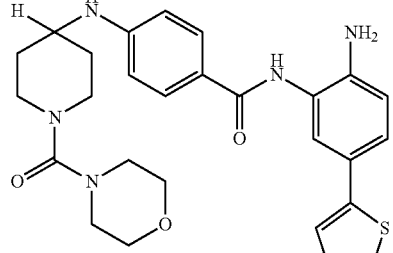 |
| 021 | 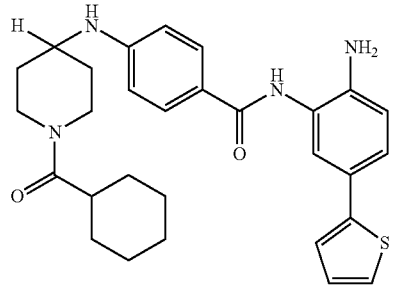 |
| 022 | 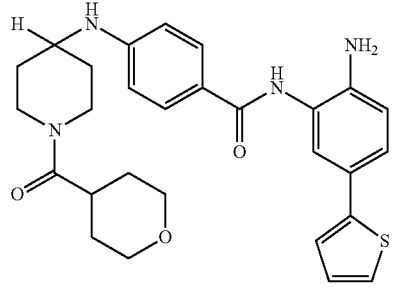 [SMILES: Nc1ccc(-c2cccs2)cc1NC(=O)c1ccc(NC2CCN(C(=O)C3CCOCC3)CC2)cc1] |
| 023 | 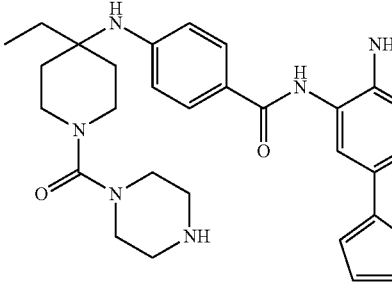 |

| ID | Structure |
|---|---|
| 024 | 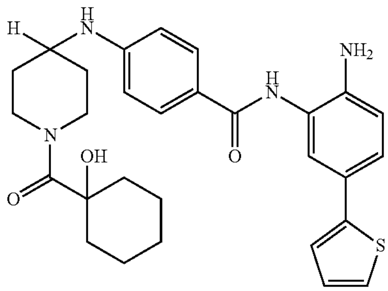 [SMILES: Nc1ccc(-c2cccs2)cc1NC(=O)c1ccc(NC2CCN(C(=O)C3(O)CCCCC3)CC2)cc1] |
| 025 | 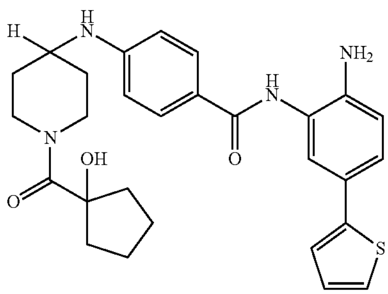 [SMILES: Nc1ccc(-c2cccs2)cc1NC(=O)c1ccc(NC2CCN(C(=O)C3(O)CCCC3)CC2)cc1] |
| 028 | 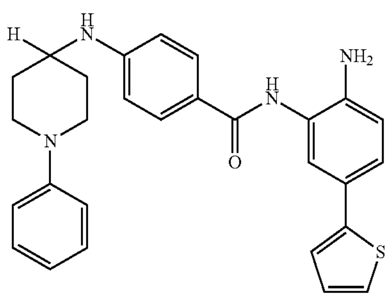 [SMILES: Nc1ccc(-c2cccs2)cc1NC(=O)c1ccc(NC2CCN(c3ccccc3)CC2)cc1] |
| 030 | 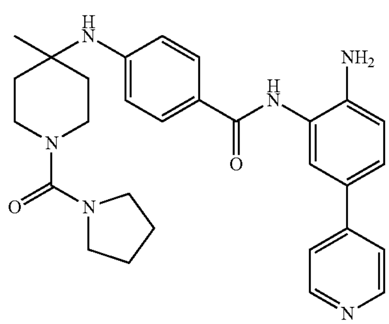 [SMILES: CC1(Nc2ccc(C(=O)Nc3cc(-c4ccncc4)ccc3N)cc2)CCN(C(=O)N2CCCC2)CC1] |
| 031 | |
| 032 | | and pharmaceutically acceptable salts thereof.

6. A pharmaceutical composition comprising a compound of claim 1 and a pharmaceutically acceptable carrier.

7. A method for treating a disease mediated by HDAC1 and/or HDAC2 in a subject comprising administering to the subject a compound of claim 1, or a pharmaceutically acceptable salt thereof, wherein the disease mediated by HDAC1 and/or HDAC2 in is selected from a group consisting of sickle-cell disease, beta-thalassemia, lung cancer, colon cancer, breast cancer, breast cancer, neuroblastoma, leukemia or lymphoma.

* * * * *